(12) United States Patent
Squitieri

(10) Patent No.: US 12,714,619 B2
(45) Date of Patent: Aug. 25, 2026

(54) CONTROLLERS FOR MANAGING PRESSURE-MITIGATION DEVICES AND PROMOTING COMPLIANCE WITH COMPLEMENTARY HEALTHCARE REGIMENS

(71) Applicant: TurnCare, Inc., Palo Alto, CA (US)

(72) Inventor: Rafael Paolo Squitieri, Wilton, CT (US)

(73) Assignee: TurnCare, Inc., Palo Alto, CA (US)

( * ) Notice: Subject to any disclaimer, the term of this patent is extended or adjusted under 35 U.S.C. 154(b) by 921 days.

(21) Appl. No.: 17/816,699

(22) Filed: Aug. 1, 2022

(65) Prior Publication Data

US 2023/0036940 A1 Feb. 2, 2023

Related U.S. Application Data

(60) Provisional application No. 63/227,779, filed on Jul. 30, 2021.

(51) Int. Cl.
*A61G 7/057* (2006.01)
*A61B 5/00* (2006.01)
(Continued)

(52) U.S. Cl.
CPC ........ *A61G 7/05776* (2013.01); *A61B 5/0205* (2013.01); *A61M 1/90* (2021.05); *G16H 20/13* (2018.01); *G16H 20/30* (2018.01); *G16H 40/60* (2018.01); *G16H 40/63* (2018.01); *G16H 40/67* (2018.01); *A61B 5/746* (2013.01); *A61G 2203/12* (2013.01); *A61J 7/0481* (2013.01); *A61M 2205/3576* (2013.01); *A61M 2205/502* (2013.01)

(58) Field of Classification Search
CPC ........ G16H 20/10; A61H 9/0078–0092; A61G 7/05776; A61G 7/05769
See application file for complete search history.

(56) References Cited

U.S. PATENT DOCUMENTS 4,077,546 A 3/1978 Winkelried
4,915,124 A 4/1990 Sember, III
(Continued)

FOREIGN PATENT DOCUMENTS

KR 200425168 Y1 8/2006

*Primary Examiner* — Valerie L Woodward
(74) *Attorney, Agent, or Firm* — Ashurst Perkins Coie US LLP; Andrew T. Pettit

(57) ABSTRACT

Introduced here are pressure-mitigation systems able to mitigate the pressure applied to a human body by the surface of an object (also referred to as a “structure”). A controller device (or simply “controller”) can be fluidically coupled to a pressure-mitigation device that includes a series of selectively inflatable chambers. When a pressure-mitigation device is placed between a human body and a surface, the controller can continuously, intelligently, and autonomously circulate fluid through the chambers of the pressure-mitigation device. Normally, the controller circulates air through the chambers of the pressure-mitigation device, though the controller could circulate another fluid, such as water or gel, through the chambers of the pressure-mitigation device. The controller may cause the chambers to be selectively inflated, deflated, or any combination thereof.

20 Claims, 26 Drawing Sheets

(51) Int. Cl.

| | |
|---|---|
| ***A61B 5/0205*** | (2006.01) |
| ***A61J 7/04*** | (2006.01) |
| ***A61M 1/00*** | (2006.01) |
| ***G16H 20/13*** | (2018.01) |
| ***G16H 20/30*** | (2018.01) |
| ***G16H 40/60*** | (2018.01) |
| ***G16H 40/63*** | (2018.01) |
| ***G16H 40/67*** | (2018.01) |

(56) References Cited

U.S. PATENT DOCUMENTS

| | | | | |
|---|---|---|---|---|
| 4,941,221 | A | 7/1990 | Kanzler | |
| 4,977,629 | A | 12/1990 | Jones | |
| 5,092,007 | A | 3/1992 | Hasty | |
| 5,282,482 | A | 2/1994 | Wilk | |
| 7,246,389 | B2 | 7/2007 | Taguchi et al. | |
| 9,030,331 | B2 | 5/2015 | Lachenbruch | |
| 9,408,477 | B1 | 8/2016 | Robinson et al. | |
| 10,463,526 | B1 | 11/2019 | Zur | |
| 11,020,543 | B1 | 6/2021 | Piesik | |
| 11,581,099 | B1 * | 2/2023 | Rufo | G16H 20/13 |
| 2002/0104535 | A1 | 8/2002 | Biondo et al. | |
| 2003/0052787 | A1 * | 3/2003 | Zerhusen | G16Z 99/00 340/286.07 |
| 2004/0211004 | A1 | 10/2004 | Thompson | |
| 2007/0258334 | A1 * | 11/2007 | Chiang | A61G 7/015 5/81.1 R |
| 2009/0194115 | A1 | 8/2009 | Squitieri | |
| 2010/0212087 | A1 * | 8/2010 | Leib | A61G 12/00 5/81.1 R |
| 2012/0317714 | A1 | 12/2012 | Matschurek | |
| 2013/0092175 | A1 | 4/2013 | Bhat et al. | |
| 2013/0126637 | A1 | 5/2013 | Hsieh et al. | |
| 2013/0253291 | A1 * | 9/2013 | Dixon | A61B 90/98 600/323 |
| 2014/0007346 | A1 | 1/2014 | Lachenbruch | |
| 2014/0221962 | A1 * | 8/2014 | Ribble | A61B 5/6892 604/503 |
| 2014/0283308 | A1 * | 9/2014 | Chen | A61H 31/008 5/699 |
| 2014/0290670 | A1 | 10/2014 | Squitieri et al. | |
| 2015/0000680 | A1 | 1/2015 | Porter, III | |
| 2015/0089748 | A1 | 4/2015 | Toms et al. | |
| 2015/0128354 | A1 | 5/2015 | Greenstein et al. | |
| 2015/0297779 | A1 | 10/2015 | Conroy et al. | |
| 2015/0335507 | A1 | 11/2015 | Emmons et al. | |
| 2015/0351983 | A1 | 12/2015 | Mcneely et al. | |
| 2016/0022520 | A1 | 1/2016 | Streeter et al. | |
| 2016/0095775 | A1 | 4/2016 | Dzioba et al. | |
| 2016/0296159 | A1 | 10/2016 | Larson et al. | |
| 2017/0007488 | A1 | 1/2017 | Tan et al. | |
| 2017/0370487 | A1 | 12/2017 | Maxfield et al. | |
| 2018/0185205 | A1 | 7/2018 | Squitieri | |
| 2018/0280219 | A1 * | 10/2018 | Garrett | A61G 7/001 |
| 2018/0284274 | A1 | 10/2018 | Lachapelle | |
| 2018/0374577 | A1 | 12/2018 | Krishna | |
| 2019/0105227 | A1 | 4/2019 | Mcneil | |
| 2019/0133857 | A1 | 5/2019 | Kuiper et al. | |
| 2019/0194574 | A1 | 6/2019 | Hanson et al. | |
| 2019/0290469 | A1 | 9/2019 | Squitieri et al. | |
| 2020/0078241 | A1 | 3/2020 | Chang et al. | |
| 2020/0163818 | A1 | 5/2020 | Theunick et al. | |
| 2020/0345539 | A1 | 11/2020 | Mao | |
| 2021/0169719 | A1 * | 6/2021 | Bosley | A61G 7/001 |
| 2021/0204720 | A1 | 7/2021 | Karschnik et al. | |
| 2021/0291009 | A1 | 9/2021 | Paganini et al. | |

* cited by examiner

Figure 13:
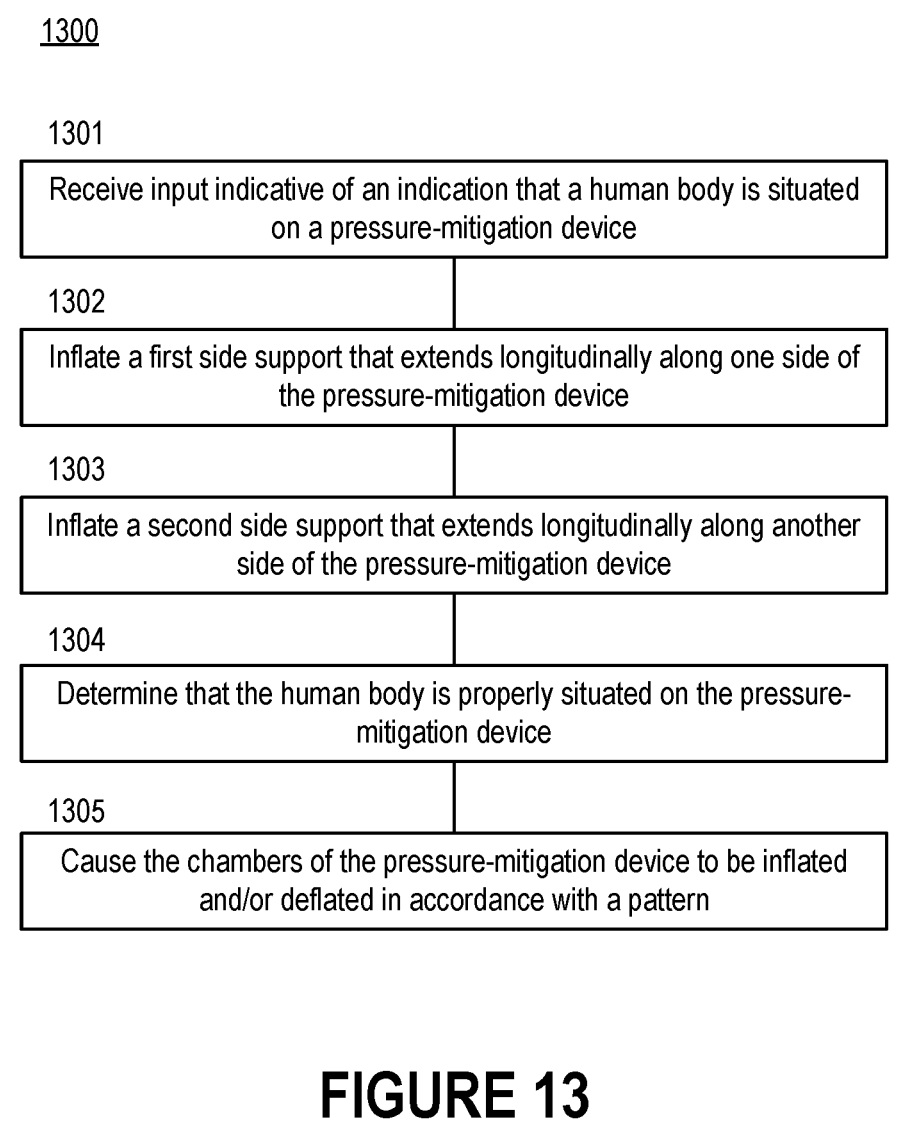

1300

1301

Receive input indicative of an indication that a human body is situated on a pressure-mitigation device

1302

Inflate a first side support that extends longitudinally along one side of the pressure-mitigation device

1303

Inflate a second side support that extends longitudinally along another side of the pressure-mitigation device

1304

Determine that the human body is properly situated on the pressure-mitigation device

1305

Cause the chambers of the pressure-mitigation device to be inflated and/or deflated in accordance with a pattern

Figures 14, 15:
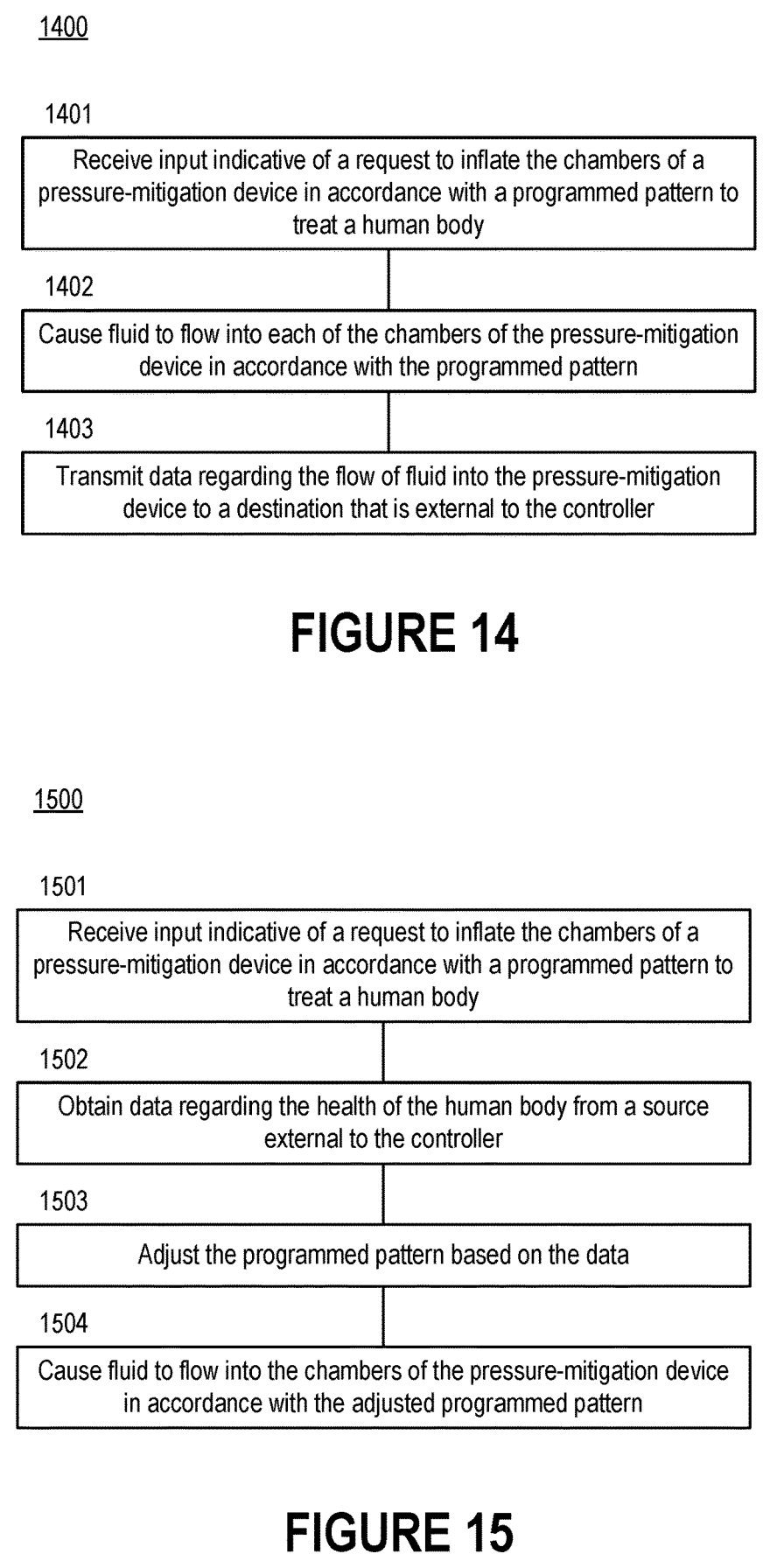

Receive input indicative of a request to inflate the chambers of a pressure-mitigation device in accordance with a programmed pattern to treat a human body

1402

Cause fluid to flow into each of the chambers of the pressure-mitigation device in accordance with the programmed pattern

1403

Transmit data regarding the flow of fluid into the pressure-mitigation device to a destination that is external to the controller

Receive input indicative of a request to inflate the chambers of a pressure-mitigation device in accordance with a programmed pattern to treat a human body

1502

Obtain data regarding the health of the human body from a source external to the controller

1503

Adjust the programmed pattern based on the data

1504

Cause fluid to flow into the chambers of the pressure-mitigation device in accordance with the adjusted programmed pattern

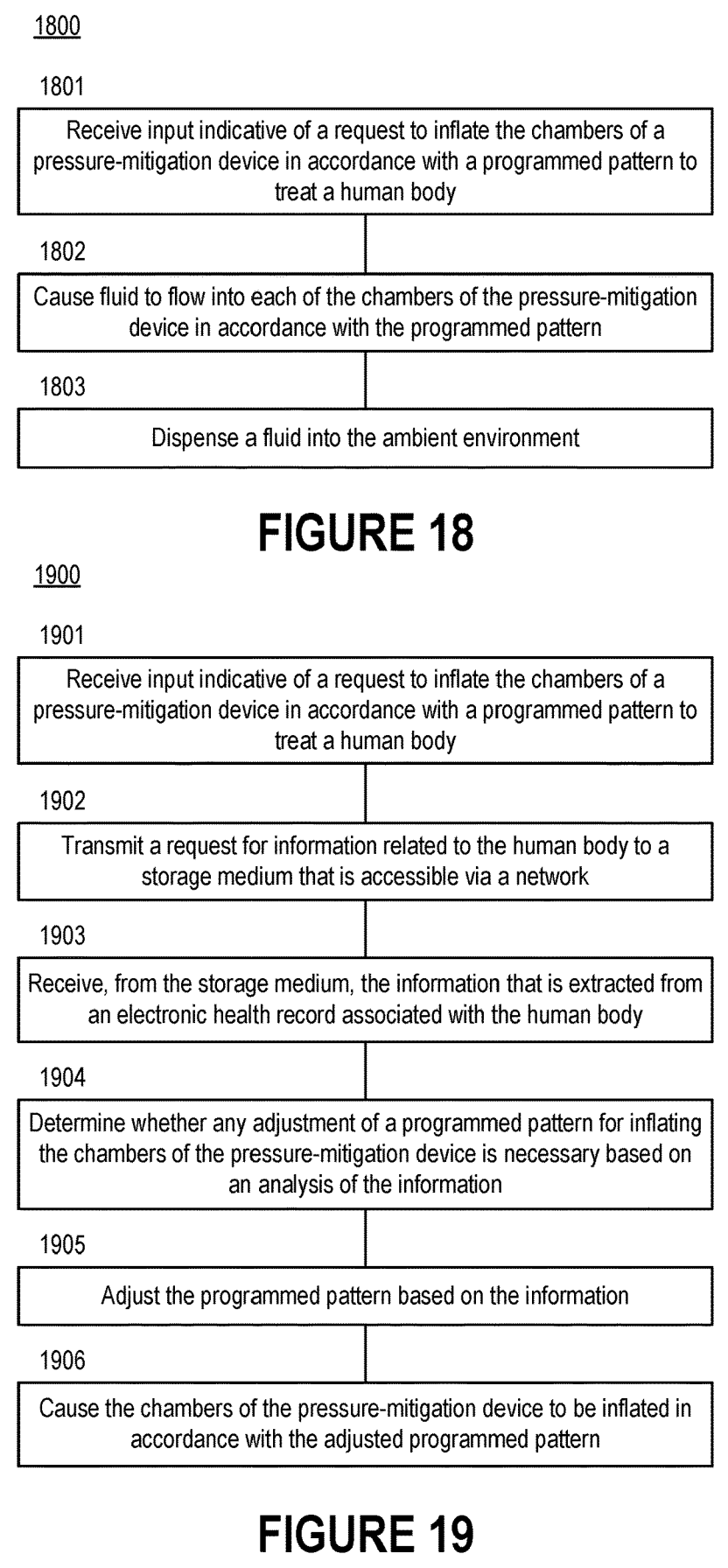

Receive input indicative of a request to inflate the chambers of a pressure-mitigation device in accordance with a programmed pattern to treat a human body

1802

Cause fluid to flow into each of the chambers of the pressure-mitigation device in accordance with the programmed pattern

1803

Dispense a fluid into the ambient environment

Receive input indicative of a request to inflate the chambers of a pressure-mitigation device in accordance with a programmed pattern to treat a human body

1902

Transmit a request for information related to the human body to a storage medium that is accessible via a network

1903

Receive, from the storage medium, the information that is extracted from an electronic health record associated with the human body

1904

Determine whether any adjustment of a programmed pattern for inflating the chambers of the pressure-mitigation device is necessary based on an analysis of the information

1905

Adjust the programmed pattern based on the information

1906

Cause the chambers of the pressure-mitigation device to be inflated in accordance with the adjusted programmed pattern

FIGURE 19

CONTROLLERS FOR MANAGING PRESSURE-MITIGATION DEVICES AND PROMOTING COMPLIANCE WITH COMPLEMENTARY HEALTHCARE REGIMENS

CROSS-REFERENCE TO RELATED APPLICATIONS

This application claims priority to U.S. Provisional Application No. 63/227,779, titled "Pressure-Mitigation Apparatuses Designed for Home and Hospital Settings with Improved Ease of Use" and filed on Jul. 30, 2021, which is incorporated herein by reference in its entirety.

TECHNICAL FIELD

Various embodiments concern pressure-mitigation systems that include pressure-mitigation apparatuses able to mitigate the pressure applied to a human body by the surface of an object and controllers for managing the flow of fluid into the pressure-mitigation apparatuses.

BACKGROUND

Pressure injuries—sometimes referred to as "decubitus ulcers," "pressure ulcers," "pressure sores," or "bedsores"—may occur as a result of steady pressure being applied in one location along the surface of the human body for a prolonged period of time. Regions with bony prominences are especially susceptible to pressure injuries. Pressure injuries are most common in individuals who are completely immobilized (e.g., on an operating table, bed, or chair) or have impaired mobility. These individuals may be older, malnourished, or incontinent, all factors that predispose the human body to formation of pressure injuries.

These individuals are often not ambulatory, so they sit or lie for prolonged periods of time in the same position. Moreover, these individuals may be unable to reposition themselves to alleviate pressure. Consequently, pressure on the skin and underlying soft tissue may eventually result in inadequate blood flow to the area, a condition referred to as "ischemia," thereby resulting in damage to the skin or underlying soft tissue. Pressure injuries can take the form of a superficial injury to the skin or a deeper ulcer that exposes the underlying tissues and places the individual at risk for infection. The resulting infection may worsen, leading to sepsis or even death in some cases.

There are technologies on the market that profess to prevent or treat pressure injuries. While these conventional technologies have many deficiencies, a common theme is the inability to precisely control the spatial relationship between a human body and a support surface (or simply "surface") that applies pressure to the human body. For example, some cushions allegedly lessen the pressure applied to the human body through the inclusion of a malleable material such as foam or gel, while other cushions allegedly lessen the pressure applied to the human body by shifting the body at least partially toward the left and right lateral recumbent positions. Individuals that use these conventional technologies are still prone to developing pressure injuries or suffering from related complications, as these conventional technologies fail to fully address the reasons that pressure injuries initially develop and continue to worsen over time.

BRIEF DESCRIPTION OF THE DRAWINGS

FIG. 13 is a flow diagram of a process for utilizing the side supports of a pressure-mitigation device to center a human body positioned thereon.

FIG. 14 includes a flow diagram of a process for transmitting data related to the flow of fluid from a controller into a pressure-mitigation device to a destination external to the controller.

FIG. 15 includes a flow diagram of a process for adjusting the programmed pattern for inflating the chambers of a pressure-mitigation device based on data received from a source external to the controller.

FIG. 18 includes a flow diagram of a process for controllably dispensing fluid into the ambient environment while a user is being treated with a pressure-mitigation system.

FIG. 19 includes a flow diagram of a process for interfacing with an electronic health record of a user that is to be treated with a pressure-mitigation system.

Figure 1A:
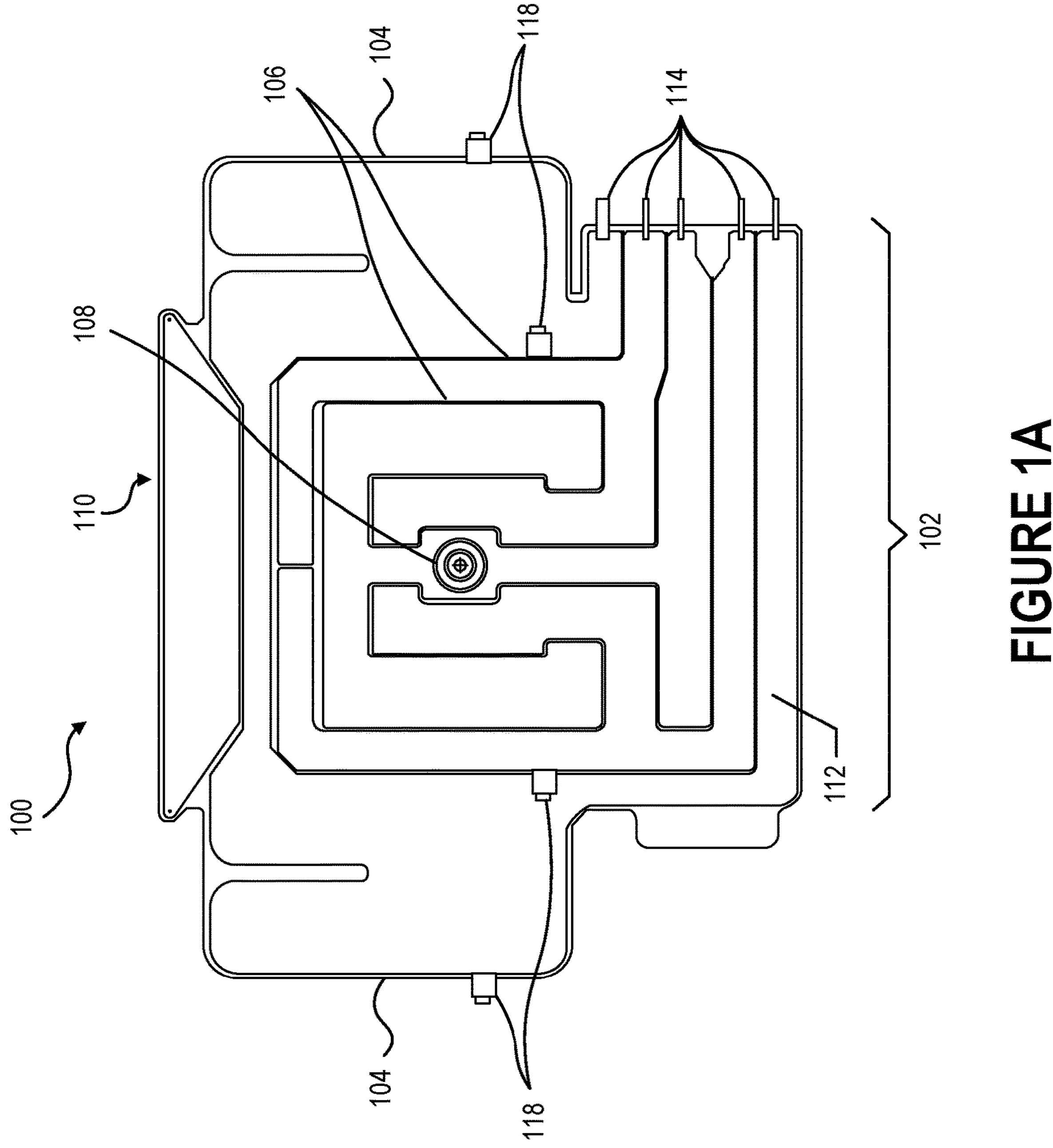
FIGS. 1A-B are top and bottom views, respectively, of a pressure-mitigation device able to relieve the pressure on an anatomical region applied by the surface of an elongated object in accordance with embodiments of the present technology.

Various features of the embodiments described herein will become more apparent to those skilled in the art from a study of the Detailed Description in conjunction with the drawings. While various embodiments are depicted in the drawings for the purpose of illustration, those skilled in the art will recognize that alternative embodiments may be employed without departing from the principles of the present disclosure. Accordingly, the embodiments are amenable to various modifications.

DETAILED DESCRIPTION

The term "pressure injury" refers to a localized region of damage to the skin and/or underlying tissue that results from force being applied thereto that results in contact pressure (or simply "pressure") on the corresponding anatomical region of the human body. Pressure injuries tend to form over bony prominences, such as the skin and soft tissue overlying the sacrum, coccyx, heels, or hips. However, other sites may also be affected. For instance, pressure injuries may form on the elbows, knees, ankles, shoulders, abdomen, back, or cranium. Pressure injuries may develop when pressure is applied to the blood vessels in soft tissue in such a manner that blood flow to the soft tissue is at least partially obstructed (e.g., due to the pressure exceeding the capillary filling pressure), and ischemia occurs at the site when such obstruction occurs for an extended duration. Accordingly, pressure injuries are normally observed on individuals who are mobility impaired, immobilized, or sedentary for prolonged periods of times.

Once pressure injuries have formed, the healing process is normally slow. When pressure is relieved from the site of a pressure injury, the body will rush blood (with proinflammatory mediators) to that region to perfuse the area with blood. The sudden reperfusion of the damaged (and previously ischemic) region has been shown to cause an inflammatory response, brought on by the proinflammatory mediators, that can actually worsen the pressure injury (and prolong recovery). Moreover, in some cases, the proinflammatory mediators may spread through the blood stream beyond the site of the pressure injury to cause a systematic inflammatory response (also referred to as a "secondary inflammatory response"). Secondary inflammatory responses caused by proinflammatory mediators have been shown to exacerbate existing conditions and trigger new conditions (and again, prolong recovery). Recovery can also be prolonged by factors that are frequently associated with individuals who are prone to pressure injuries, such as old age, immobility, preexisting medical conditions (e.g., arteriosclerosis, diabetes, or infection), smoking, and medications (e.g., anti-inflammatory drugs). Inhibiting the formation of pressure injuries (and reducing the prevalence of proinflammatory mediators) can enhance and expedite many treatment processes, especially for those individuals whose mobility is impaired during treatment.

Introduced here, therefore, are pressure-mitigation systems able to mitigate the pressure applied to a human body by the surface of an object (also referred to as a "structure"). A controller device (or simply "controller") can be fluidically coupled to a pressure-mitigation device (also referred to as a "pressure-mitigation apparatus" or a "pressure-mitigation pad") that includes a series of selectively inflatable chambers (also referred to as "cells" or "compartments"). When a pressure-mitigation device is placed between a human body and a surface, the controller can continuously, intelligently, and autonomously circulate fluid through the chambers of the pressure-mitigation device. Normally, the controller circulates air through the chambers of the pressure-mitigation device, though the controller could circulate another fluid, such as water or gel, through the chambers of the pressure-mitigation device. As further discussed below, the controller may cause the chambers to be selectively inflated, deflated, or any combination thereof.

The present disclosure concerns various aspects of these pressure-mitigation systems that allow for more rapid deployment and use in various settings. As further discussed below, these aspects allow for pressure-mitigation systems to not only be more broadly deployed, but also more easily used by individuals without any experience or expertise in rendering healthcare services. For example, some embodiments could be designed for deployment in a home setting, where a person with no training may operate a pressure-mitigation system for herself or on behalf of a friend or family member. As another example, some embodiments could be designed for deployment in a healthcare setting, where a person with meaningful training may operate a pressure-mitigation on behalf of a user (also called a "patient" or "subject"). Examples of healthcare settings include hospitals, clinics, surgery facilities, recovery centers, nursing homes, and the like. Pressure-mitigation systems that are designed for home settings may include, offer, or support features that might otherwise be provided by equipment accessible in a hospital setting. Likewise, pressure-mitigation systems designed for hospital settings may include, offer, or support features that might otherwise be provided by equipment accessible in a home setting.

As mentioned above, the pressure-mitigation device has inflatable chambers whose pressure can be individually varied in a controlled manner. The inflatable chambers can be designed and arranged so as to facilitate alignment of a given anatomical region (e.g., the sacral region) with the pressure-mitigation device. For example, the inflatable chambers may be intertwined around an epicenter in a geometric pattern based on the internal anatomy of the given anatomical region. Specifically, the inflatable chambers may be intertwined such that a collective perimeter is representative of a quadrilateral, such as a square or rectangle. As further discussed below, side supports can extend longitudinally along opposite sides of the pressure-mitigation device along at least a portion of the length of the quadrilateral.

When the inflatable chambers of the pressure-mitigation device are pressurized in accordance with a programmed pattern executed by the controller, a body-surface interaction is produced that emulates the interactions seen in healthy (e.g., mobile) individuals who are able to reposition themselves to periodically adjust the pressure applied by the surface. Note that the pattern may be "programmed" in terms of time, pressure, flow rate, or any combination thereof. Instead of the patient periodically moving herself to adjust the pressure applied by the surface, the pressure-mitigation device shifts the location at which the main point of pressure is applied. Accordingly, the pressure-mitigation device, in conjunction with the controller, can mimic the micro-adjustments that healthy individuals regularly make. This creates a scenario in which an individual can remain partially or entirely motionless for an extended period of time, yet physiologically the net pressure effect on the individual is roughly the same as if the individual had maintained more natural motion (e.g., performed micro-adjustments). Such an approach prevents prolonged tissue compression, which can lead to ischemia and reperfusion injuries that result in lasting tissue damage (e.g., in the form of ulcers) and other adverse systemic health consequences.

By controllably varying the pressure in the series of chambers, the controller can move the main point of pressure applied by the surface to different regions across the human body. For example, the controller may cause the main point of pressure applied by the surface to be moved amongst a plurality of predetermined anatomic locations by sequentially varying the level of inflation of (and pressure in) predetermined subsets of chambers. Such an approach results in pressure gradients being created across the human body. In some embodiments, the controller controls the pressure of chambers located beneath specific anatomic locations for specific durations in order to move one or more points of pressure applied by the underlying surface around the anatomy in a precise manner such that specific portions of the anatomy (e.g., the tissue adjacent to bony prominences) do not experience direct pressure for an extended duration. The relocation of the pressure point(s) avoids vascular compression for sustained periods of time, inhibits ischemia, and reduces the incidence of pressure injuries.

Such an approach to mitigating pressure is useful in various contexts.

Assume, for example, that an individual has been identified as a candidate for treatment after entering a hospital. In such a scenario, a healthcare professional may obtain a portable pressure-mitigation system (or simply "system") comprised of a pressure-mitigation device and a controller. Examples of healthcare professionals include doctors, nurses, therapists, and the like. The healthcare professional can deploy the pressure-mitigation device on a surface on which the individual is to be immobilized, either partially or entirely, and then orient the individual on top of the pressure-mitigation device. Thereafter, the healthcare professional can cause the system to shift a point of pressure applied by the surface to the individual by pressurizing the inflatable chambers of the pressure-mitigation device to varying degrees in accordance with a programmed pattern. For example, the healthcare professional may initiate pressurization of the inflatable chambers by indicating that treatment should begin via the controller.

As another example, assume that an individual has been instructed to utilize a pressure-mitigation device as part of a treatment regimen (e.g., following discharge from a hospital). In such a scenario, the individual may be provided with a system comprised of a pressure-mitigation device and a controller. When the individual reaches her home, she can deploy the pressure-mitigation device on a surface on which she is to be immobilized. For example, the individual may arrange the pressure-mitigation device on a chair or bed as further discussed below. After the individual arranges herself on top of the pressure-mitigation device, she can cause the system to shift a point of pressure applied by the surface to her body by pressurizing the inflatable chambers of the pressure-mitigation device to varying degrees in accordance with a programmed pattern. For example, the individual may interact with the controller in such a manner (e.g., by pressing a mechanical interface component, such as a button or switch) so as to indicate that fluid should begin flowing into the pressure-mitigation device. Those skilled in the art will recognize that a similar process may be performed if the system is provided to, or deployed by, a caretaker of the individual. Note that the term "caretaker," as used herein, is generally used to refer to a person who helps another person to receive treatment, but is not herself a healthcare professional. Examples of caretakers include family members, friends, and aides.

Embodiments may be described with reference to particular anatomical regions, treatment regimens, environments, and the like. However, those skilled in the art will recognize that the features are similarly applicable to other anatomical regions, treatment regimens, and environments. As an example, embodiments may be described in the context of a pressure-mitigation device that is positioned adjacent to an anterior anatomical region of an individual oriented in the prone position. However, aspects of those embodiments may apply to a pressure-mitigation device that is positioned adjacent to a posterior anatomical region of an individual oriented in the supine position.

While embodiments may be described in the context of machine-readable instructions, aspects of the technology can be implemented via hardware, firmware, or software. As an example, a controller may not only execute instructions for determining an appropriate rate at which to permit fluid (e.g., air) to flow into each inflatable chamber of a pressure-mitigation device, but may also be responsible for facilitating communication with other computing devices. The controller may be able to communicate with a mobile device that is associated with the individual, caregiver, or healthcare professional, or the controller may be able to communicate with a computer server of a network-accessible server system, for example, that includes a computer program that manages electronic health records on behalf of one or more healthcare entities.

Terminology

References in the present disclosure to "an embodiment" or "some embodiments" mean that the feature, function, structure, or characteristic being described is included in at least one embodiment. Occurrences of such phrases do not necessarily refer to the same embodiment, nor are they necessarily referring to alternative embodiments that are mutually exclusive of one another.

The term "based on" is to be construed in an inclusive sense rather than an exclusive sense. That is, in the sense of "including but not limited to." Thus, unless otherwise noted, the term "based on" is intended to mean "based at least in part on."

The terms "connected," "coupled," and variants thereof are intended to include any connection or coupling between two or more elements, either direct or indirect. The connection or coupling can be physical, logical, or a combination thereof. For example, elements may be electrically or communicatively coupled to one another despite not sharing a physical connection.

The term "module" may refer broadly to software, firmware, hardware, or combinations thereof. Modules are typically functional components that generate one or more outputs based on one or more inputs. A computer program may include or utilize one or more modules. For example, a computer program may utilize multiple modules that are responsible for completing different tasks, or a computer program may utilize a single module that is responsible for completing all tasks.

When used in reference to a list of multiple items, the word "or" is intended to cover all of the following interpretations: any of the items in the list, all of the items in the list, and any combination of items in the list.

Overview of Pressure-Mitigation Devices

A pressure-mitigation device includes a plurality of chambers into which fluid can flow. Each chamber may be associated with a discrete flow of fluid so that the pressure in the plurality of chambers can be varied as necessary. When placed on the surface of an object on which a human body rests, the pressure-mitigation device can vary the pressure on an anatomical region by controllably inflating chamber(s) and/or deflating chamber(s) to create pressure gradients across the anatomical regions. Several examples of pressure-mitigation devices are described below with respect to FIGS. 1A-4C. Unless otherwise noted, any features described with respect to one embodiment are equally applicable to other embodiments. Some features have only been described with respect to a single embodiment for the purpose of simplifying the present disclosure.

Figure 1B:
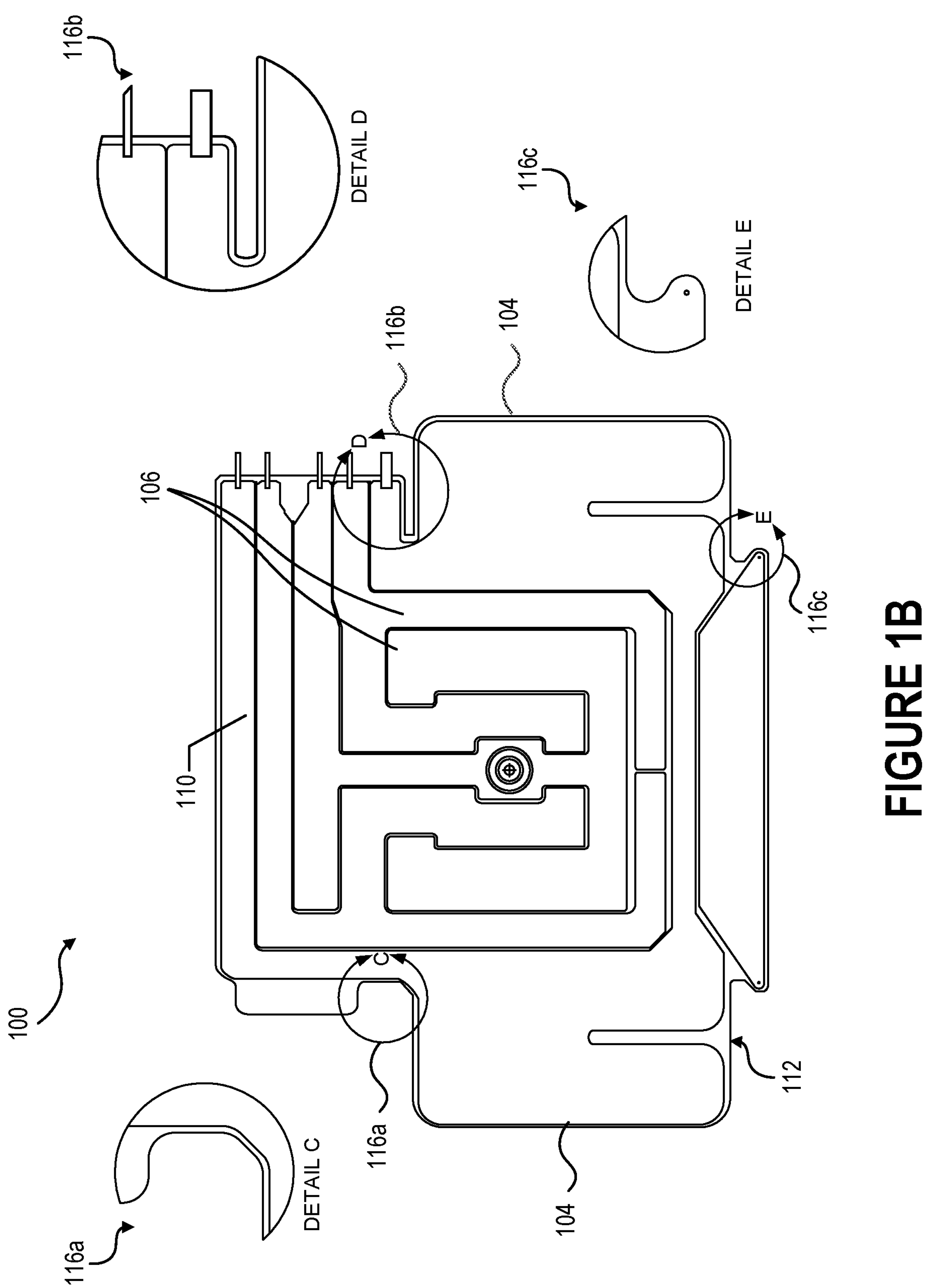

FIGS. 1A-B are top and bottom views, respectively, of a pressure-mitigation device 100 able to relieve the pressure on an anatomical region applied by the surface of an elongated object in accordance with embodiments of the present technology. While the pressure-mitigation device 100 may be described in the context of elongated objects, such as mattresses, stretchers, operating tables, and procedure tables, the pressure-mitigation device 100 could be deployed on non-elongated objects. In some embodiments, the pressure-mitigation device 100 is secured to a surface using an attachment apparatus. In such embodiments, the attachment apparatus may be laid upon the surface, and the pressure-mitigation device 100 may be laid upon the attachment apparatus that facilitates securement of the pressure-mitigation device 100 to the surface. In other embodiments, the pressure-mitigation device 100 is placed in direct contact with the surface without any attachment apparatus therebetween. For example, the pressure-mitigation device 100 may have a tacky substance deposited along at least a portion of its outer surface that allows it to temporarily adhere to the surface. Examples of tacky substances include latex, urethane, and silicone rubber.

As shown in FIG. 1A, the pressure-mitigation device 100 can include a central portion 102 (also referred to as a "contact portion") that is positioned alongside at least one side support 104. Here, a pair of side supports 104 are arranged on opposing sides of the central portion 102. However, some embodiments of the pressure-mitigation device 100 do not include any side supports. For example, the side supports 104 may be omitted when the individual is medically immobilized (e.g., under anesthesia, in a medically induced coma, etc.) and/or physically restrained by an underlying object (e.g., by rails along the side of a bed, armrests along the side of a chair, etc.) or some other structure (e.g., physical restraints, casts, etc.).

The pressure-mitigation device 100 includes a series of chambers 106 whose pressure can be individually varied. In some embodiments, the series of chambers 106 are arranged in a geometric pattern designed to relieve pressure on one or more anatomical regions of a human body. For example, the series of chambers 106 may be intertwined with one another so that, when a human body is positioned on the pressure-mitigation device 100 with the sacral region generally situated near the middle, the lumbar region and/or the gluteal regions can be supported through inflation of the series of chambers 106. As noted above, when placed between the human body and a surface, the pressure-mitigation device 100 can vary the pressure on these anatomical region(s) by controllably inflating and/or deflating chamber(s).

In some embodiments, the series of chambers 106 are arranged such that pressure on a given anatomical region is mitigated when the given anatomical region is oriented over a target region 108 of the geometric pattern. As shown in FIGS. 1A-B, the target region 108 may be representative of a central point of the pressure-mitigation device 100 to appropriately position the anatomy of the human body with respect to the pressure-mitigation device 100. For example, the target region 108 may correspond to the epicenter of the geometric pattern. However, the target region 108 may not necessarily be the central point of the pressure-mitigation device 100, particularly if the series of chambers 106 are positioned in a non-symmetric arrangement. The target region 108 may be visibly marked so that an individual can readily align the target region 108 with a corresponding anatomical region of the human body to be positioned thereon. Thus, the pressure-mitigation device 100 may include a visual element representative of the target region 108 to facilitate alignment with the corresponding anatomical region of the human body. The individual could be a healthcare professional, caregiver, or the patient herself.

The pressure-mitigation device 100 can include a first portion 110 (also referred to as a "first layer" or "bottom layer") designed to face a surface and a second portion 112 (also referred to as a "second layer" or "top layer") designed to face the human body supported by the surface. In some embodiments, the pressure-mitigation device 100 is deployed such that the first portion 110 is directly adjacent to the surface. For example, the first portion 110 may have a tacky substance deposited along at least a portion of its exterior surface that facilitates temporarily adhesion to the support surface. In other embodiments, the pressure-mitigation device 100 is deployed such that the first portion 110 is directly adjacent to an attachment apparatus designed to help secure the pressure-mitigation device 100 to the support surface. The pressure-mitigation device 100 may be constructed of various materials, and the materials used in the construction of each component of the pressure-mitigation device 100 may be chosen based on the nature of the body contact, if any, to be experienced by the component. For example, because the second portion 112 will often be in direct contact with the skin, it may be comprised of a soft fabric or a breathable fabric (e.g., comprised of moisture-wicking materials or quick-drying materials, or having perforations). In some embodiments, an impervious lining (e.g., comprised of polyurethane) is secured to the inside of the second portion 112 to inhibit fluid (e.g., sweat) from entering the series of chambers 106. As another example, if the pressure-mitigation device 100 is designed for deployment beneath a cover (e.g., a bed sheet), then the second portion 112 may be comprised of a flexible, liquid-impervious material, such as polyurethane, polypropylene, silicone, or rubber. The first portion 110 may also be comprised of a flexible, liquid-impervious material.

Generally, the first and second portions 110, 112 are selected and/or designed such that the pressure-mitigation device 100 is readily cleanable. However, the specific materials that are used may vary depending on the environment in which the pressure-mitigation device 100 is to be deployed. Assume, for example, that the pressure-mitigation device 100 is intended to be deployed in a hospital environment. In such a scenario, the first and second portions 110, 112 may be readily cleanable with a cleaning agent (e.g., bleach) or a cleaning procedure (e.g., sterilization) that is known to be used in hospital environments. Because the pressure-mitigation device 100 will remain in the hospital environment under the care of knowledgeable persons, the first and second portions 110, 112 could be comprised of materials that may degrade quickly if not properly cared for. Examples of such materials include high-performance fabric, upholstery, vinyl, and other suitable textiles. If the pressure-mitigation device 100 is instead intended to be deployed in a home environment, the first and second portions 110, 112 may be comprised of materials that can be readily cleaned by persons without extensive experience. For example, the first portion 110 and/or the second portion 112 may be comprised of a vinyl that is easy to clean with commonly available cleaning agents (e.g., bleach, liquid dish soap, all-purpose cleaners). As another example, the first and second portions 110, 112 may be comprised of a rugged fabric that can be washed in a washing machine without meaningful degradation. Regardless of the environment, the first and second portions 110, 112 may contain antimicrobial additives, antifungal additives, flame-retardant additives, and the like. These additives may be embedded in the materials used to create the first and second portions 110, 112, or these additives may be applied to the first and second portions 110, 112, for example, in the form of a coating that is sprayed or laminated along the outer surfaces.

The series of chambers 106 may be formed via interconnections between the first and second portions 110, 112. For example, the first and second portions 110, 112 may be bound directly to one another, or the first and second portions 110, 112 may be bound to one another via one or more intermediary layers. In embodiments where the first and second portions 110, 112 are bound directly to one another without any intermediary layers, the pressure-mitigation device 100 may be substantially flat when the series of chambers 106 are in the deflated state. Said another way, when the series of chambers 106 are in the deflated state, the pressure-mitigation device 100 can be substantially planar without meaningful height or variations in height. Such a design can be beneficial as it ensures that the pressure-mitigation device 100 can remain beneath the human body even when no fluid is flowing into the series of chambers 106. When a conventional cushion is deflated, ridges tend to form where the layers are bound together (e.g., along the periphery). These ridges can be irritating, as each ridge will apply pressure to the human body. However, this concern can be addressed by designing the pressure-mitigation device 100 to be largely flat when the series of chambers 106 are deflated.

In the embodiment illustrated in FIGS. 1A-B, the pressure-mitigation device 100 includes an “M-shaped” chamber intertwined with two “C-shaped” chambers that face one another. Such an arrangement has been shown to effectively mitigate the pressure applied to the sacral region of a human body in the supine position by a support surface when the pressure in these chambers is alternated. The series of chambers 106 may be arranged differently if the pressure-mitigation device 100 is designed for an anatomical region other than the sacral region, or if the pressure-mitigation device 100 is to be used to support a human body in a non-supine position (e.g., a prone position or sitting position). Generally, the geometric pattern of chambers 106 is designed based on the internal anatomy (e.g., the muscles, bones, and vasculature) of the anatomical region on which pressure is to be relieved.

A healthcare professional, caregiver, or the person to be treated using the pressure-mitigation device 100 may be responsible for actively orienting the anatomical region of the human body lengthwise over the target region 108 of the geometric pattern. If the pressure-mitigation device 100 includes one or more side supports 104, the side supports 104 may actively orient or guide the anatomical region of the human body laterally over the target region 108 of the geometric pattern. For example, after situating the human body over the series of chambers 106, a healthcare professional or caregiver may initiate an orientation operation (e.g., by interacting with the controller) in which the side supports 104 are inflated to “push” the human body over the target region 108. Alternatively, the side supports 104 may passively orient or guide the anatomical region of the human body laterally over the target region 108 of the geometric pattern. For example, at least a portion of each side support may be stuffed with cotton, latex, polyurethane foam, gel, or any combination thereof. These “stuffed” side supports can passively orient the human body by defining a channel in which the human body is to be situated.

As further described below with respect to FIGS. 7A-C, a controller can separately control the pressure in each chamber—as well as the side supports 104, if included—by providing a discrete airflow via one or more corresponding valves 114. In some embodiments, the valves 114 are permanently secured to the pressure-mitigation apparatus 100 and designed to interface with tubing that can be readily detached (e.g., for easier transport, storage, etc.). Each valve 114 may be designed to mate with a complementary end of the tubing, for example, that is designed or sized to securely yet removably “grasp” that valve. Here, the pressure-mitigation device 100 includes five valves 114. Three valves are fluidically coupled to the series of chambers 106, and two valves are fluidically coupled to the side supports 104. Other embodiments of the pressure-mitigation apparatus 100 may include more than five valves or less than five valves. For example, the pressure-mitigation device 100 may be designed such that a pair of side supports 104 are pressurized via a single airflow received via a single valve.

In some embodiments, the pressure-mitigation device 100 includes one or more design features 116*a-c* that are designed to facilitate securement of the pressure-mitigation device 100 to the surface of an object and/or an attachment apparatus. As illustrated in FIG. 1B, for example, the pressure-mitigation device 100 may include three design features 116*a-c*, each of which can be aligned with a corresponding structural feature that is accessible along the surface of the object or the attachment apparatus. For example, each design feature 116*a-c* may be designed to at least partially envelope a structural feature that protrudes upward. One example of such a structural feature is a rail that extends along the side of a bed. The design features 116*a*-*c* may also facilitate proper alignment of the pressure-mitigation device 100 with the surface of the object or the attachment apparatus.

One or more release valves 118 (also referred to as "discharge valves" or simply "valves") may be located along the periphery of the pressure-mitigation device 100 to allow for quick discharge of the fluid stored therein. Normally, the release valves 118 are located along the longitudinal sides to ensure that the release valves 118 are not located beneath a human body that is situated on the pressure-mitigation apparatus 100. Generally, it is desirable to locate the release valves 118 so that the release valves 118 are accessible even when the pressure-mitigation device 100 is being used. The release valves 118 may allow discharge of fluid from the side supports 104 and/or the series of chambers 106.

Referring to the side supports 104, fluid may be separately dischargeable therefrom if (i) each side support is fluidically decoupled from the other side support and (ii) each side support has at least one release valve. This design—namely, where the side supports 104 are fluidically decoupled from one another—may be desirable in some scenarios because fluid can quickly be discharged from the side supports 104, which allows the human body situated on the pressure-mitigation device 100 to be accessed (e.g., in the case of a medical emergency). Alternatively, fluid may be collectively dischargeable from the side supports 104 if (i) the side supports 104 are fluidically coupled to each other and (ii) the side supports 104 have at least one release valve. This approach to "dually deflating" the side supports 104 may be taken if the release valve(s) are connected to only one side support, even if both side supports are fluidically coupled to one another.

Accordingly, a first release valve could be located along the periphery of a first side support of the pair of side supports 104. When engaged, the first release valve allows for the release of fluid from the first side support. In embodiments where the first side support is fluidically coupled to the second side support, when the release valve is engaged, fluid is released from the pair of side supports 104. As shown in FIG. 1, a second release valve may be located along the periphery of the second side support in some embodiments. When engaged, the second release valve allows for the release of fluid from the second side support. Thus, a single release valve may be connected to a pair of side supports that are fluidically couped to one another, or a pair of release valves may be connected to a pair of side supports that may or may not be fluidically coupled to one another.

Additionally or alternatively, valves may be connected to some or all of the chambers 106 that collectively form a geometric arrangement. Assume, for example, that the pressure-mitigation device 100 includes three chambers in addition to two side chambers that are fluidically coupled to each other. In such a scenario, valves may be connected to any of the three chambers, as well as any of the two side chambers. Thus, the pressure-mitigation device may include a set of valves, at least some of which allow for the release of fluid from the chambers 106 and at least some of which allow for the release of fluid from the side supports 104. Generally, each valve allows fluid to be rapidly yet controllably released from either a corresponding chamber or a corresponding side support, though a valve could be configured to permit the release of fluid from multiple chambers or multiple side supports.

Regardless of the number of valves, each valve is normally located proximate to the periphery of the pressure-mitigation device 100. Such an approach to locating valves ensures that the valves remain usable even while a human body is situated on the pressure-mitigation device 100.

Each release valve may be mechanically or electrically actuated.

In embodiments where the release valves are mechanically actuatable, each release valve may be actuated by an individual engaging a mechanical button (also referred to as a "strike button" or "release button") that, when pressed, opens a channel through which fluid flows out of the corresponding chamber or corresponding side support into the ambient environment. In embodiments where the fluid is water or gel, the fluid may be directed into a container (e.g., from which the fluid can then be rerouted through the controller as further discussed below).

In embodiments where the release valves are electrically actuatable, the release valves may be actuated in different ways. For example, each release valve may include an actuator configured to controllably engage the valve, and a switch assembly may be located along an exterior surface of the pressure-mitigation device 100, where when engaged, the switch assembly can cause transmission of a signal to the actuator to prompt engagement of the valve. As another example, each release valve may include an actuator configured to controllably engage the valve, and the pressure-mitigation device 100 may include a processor that is configured to receive input indicative of an instruction to release fluid from the corresponding chamber or corresponding side support and then cause transmission of a signal to the actuator, so as to prompt engagement of the valve. The instruction may be provided via the controller or another computing device (e.g., a mobile phone or wearable electronic device) that is communicatively connected to the pressure-mitigation device 100. Thus, the input may be received from the controller that is fluidically connected to the pressure-mitigation device 100 and responsible for managing the flow of fluid into the series of chambers 106 and pair of side supports 104. Alternatively, the input may be received from a computing device that is communicatively connected to the pressure-mitigation device 100, either directly or indirectly (e.g., via the controller).

In some embodiments, all of the release valves included in the pressure-mitigation device 100 may be collectively engageable. Valves may be synchronized via a physical or digital coupling that allows the valves to work in concert with one another. Such a feature allows for the simultaneous release of fluid from each chamber or side support. In some embodiments, subsets of the valves are collectively engageable. Assume, for example, that the pressure-mitigation device 100 includes five release valves, three release valves for the three chambers and two release valves for the two side supports. In such a scenario, the three release valves may be collectively engageable, to allow for the simultaneous release of fluid from the three chambers. Additionally or alternatively, the two release valves may be collectively engageable, to allow for the simultaneous release of fluid from the two side supports.

FIG. 1 shows an embodiment where the release valves are separate from the valves through which fluid flows into the pressure-mitigation device 100. Because the release valves facilitate the discharge of fluid from the pressure-mitigation device 100, the release valves may be referred to as "egress valves" while the valves through which fluid flows into the pressure-mitigation device 100 may be referred to as "ingress valves." In some embodiments, the same valves may allow for the bidirectional flow of fluid. Said another way, a "bidirectional valve" may allow for ingress and egress of fluid depending on its state.

Figure 2A:
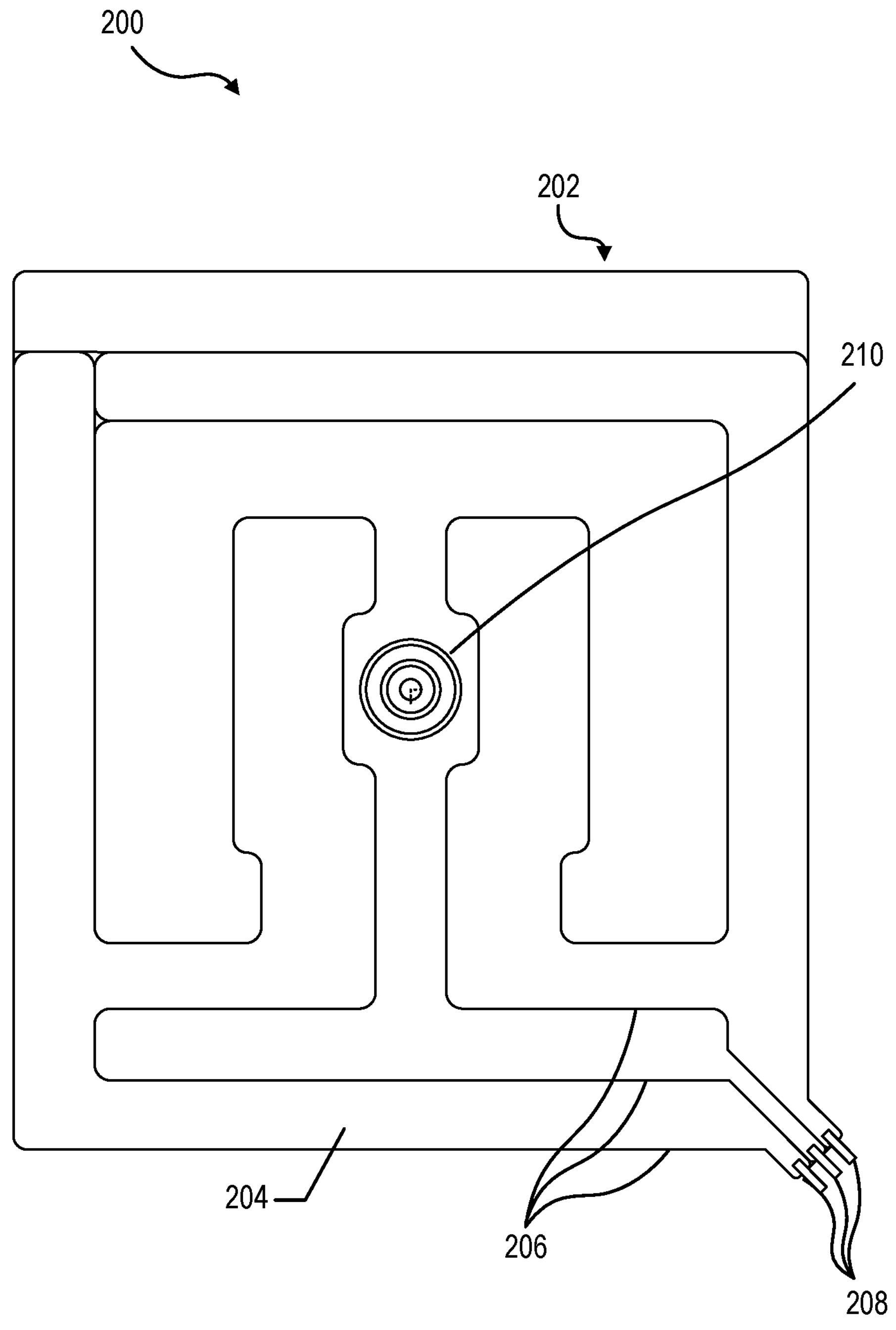
FIGS. 2A-B are top and bottom views, respectively, of a pressure-mitigation device configured in accordance with embodiments of the present technology.
Figure 2B:
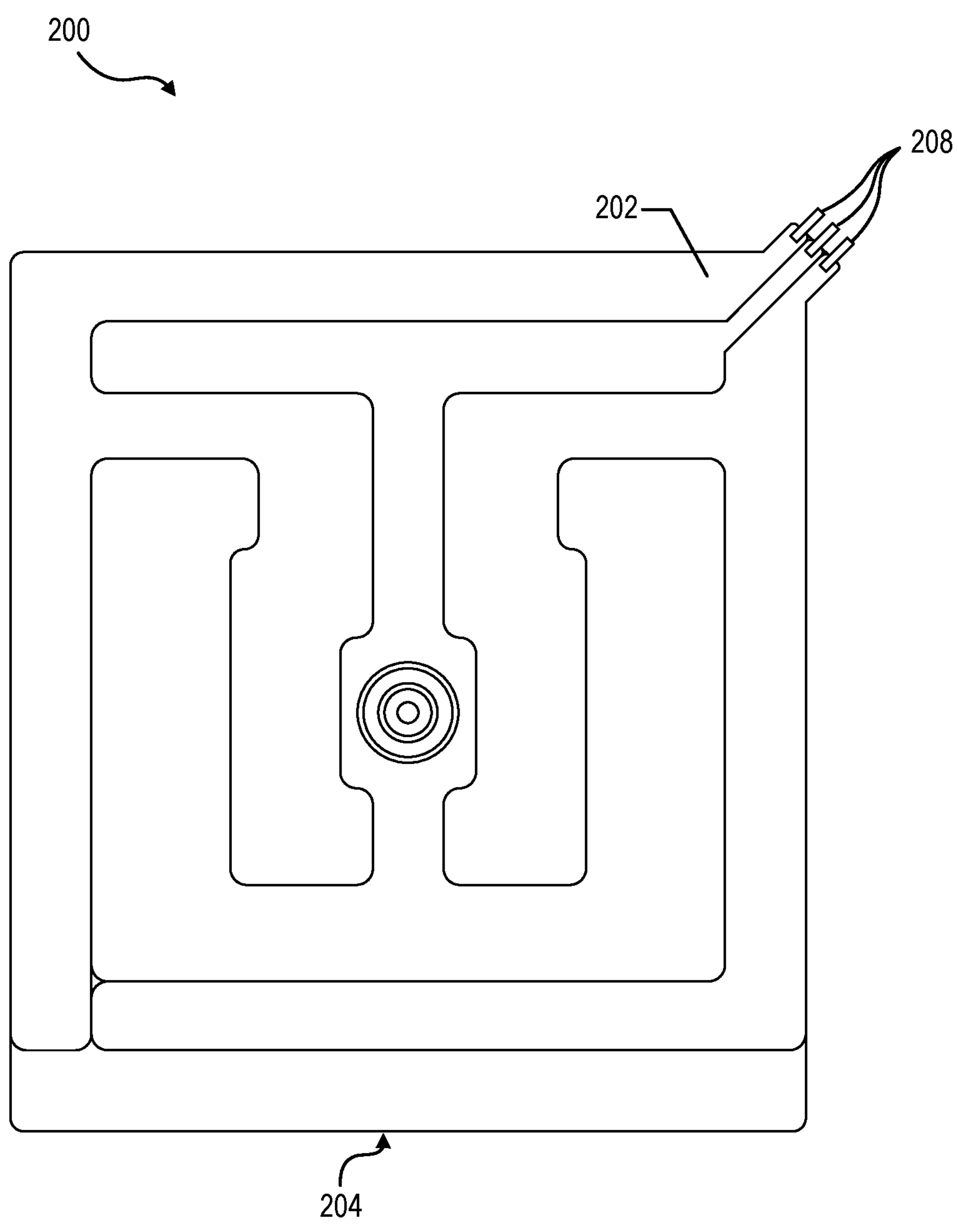

FIGS. 2A-B are top and bottom views, respectively, of a pressure-mitigation device 200 configured in accordance with embodiments of the present technology. The pressure-mitigation device 200 is generally used in conjunction with non-elongated objects that support individuals in a seated or partially erect position. Examples of non-elongated objects include chairs (e.g., office chairs, examination chairs, recliners, and wheelchairs) and the seats included in vehicles and airplanes. Accordingly, the pressure-mitigation device 200 may be positioned atop surfaces that have side supports integrated into the object itself (e.g., the side arms of a recliner or wheelchair). Note, however, that the pressure-mitigation device 200 could likewise be used in conjunction with elongated objects in a manner generally similar to the pressure-mitigation device 100 of FIGS. 1A-B.

In some embodiments, the pressure-mitigation device 200 is secured to a surface using an attachment apparatus. In other embodiments, the attachment apparatus is omitted such that the pressure-mitigation device 200 directly contacts the underlying surface. In such embodiments, the pressure-mitigation device 200 may have a tacky substance deposited along at least a portion of its outer surface that allows it to temporarily adhere to the surface.

The pressure-mitigation device 200 can include various features similar to the features of the pressure-mitigation device 100 described above with respect to FIGS. 1A-B. For example, the pressure-mitigation device 200 may include a first portion 202 (also referred to as a "first layer" or "bottom layer") designed to face the surface, a second portion 204 (also referred to as a "second layer" or "top layer") designed to face the human body supported by the surface, and a plurality of chambers 206 formed via interconnections between the first and second portions 202, 204. In this embodiment, the pressure-mitigation device 200 includes an "M-shaped" chamber intertwined with a backward "J-shaped" chamber and a backward "C-shaped" chamber. Varying the pressure in such an arrangement of chambers 206 has been shown to effectively mitigate the pressure applied by a surface to the gluteal and sacral regions of a human body in a seated position. These chambers may be intertwined to collectively form a square-shaped pattern. Pressure-mitigation devices designed for deployment on the surfaces of non-elongated objects may have substantially quadrilateral-shaped patterns of chambers, while pressure-mitigation devices designed for deployment on the surfaces of elongated objects may have substantially square-shaped patterns of chambers.

As further discussed below, the chambers 206 can be inflated and/or deflated in a predetermined pattern and to predetermined pressure levels. The individual chambers 206 may be inflated to higher pressure levels than the chambers 106 of the pressure-mitigation device 100 described with respect to FIGS. 1A-B because the human body being supported by the pressure-mitigation apparatus 200 is in a seated position, thereby causing more pressure to be applied by the underlying surface than if the human body were in a supine or prone position. Further, unlike the pressure mitigation device 100 of FIGS. 1A-B, the pressure-mitigation device 200 of FIGS. 2A-B does not include side supports. As noted above, side supports may be omitted when the object on which the individual is situated (e.g., seated or reclined) already provides components that will laterally center the human body, as is often the case with non-elongated support surfaces. One example of such a component is the armrests along the side of a chair.

As further described below with respect to FIGS. 7A-C, a controller can control the pressure in each chamber 206 by providing a discrete airflow via one or more corresponding valves 208. Here, the pressure-mitigation apparatus 200 includes three valves 208, and each of the three valves 208 corresponds to a single chamber 206. Other embodiments of the pressure-mitigation apparatus 200 may include fewer than three valves or more than three valves, and each valve can be associated with one or more chambers to control inflation/deflation of those chamber(s). A single valve could be in fluid communication with two or more chambers. Further, a single chamber could be in fluid communication with two or more valves (e.g., one valve for inflation and another valve for deflation).

Figure 3:
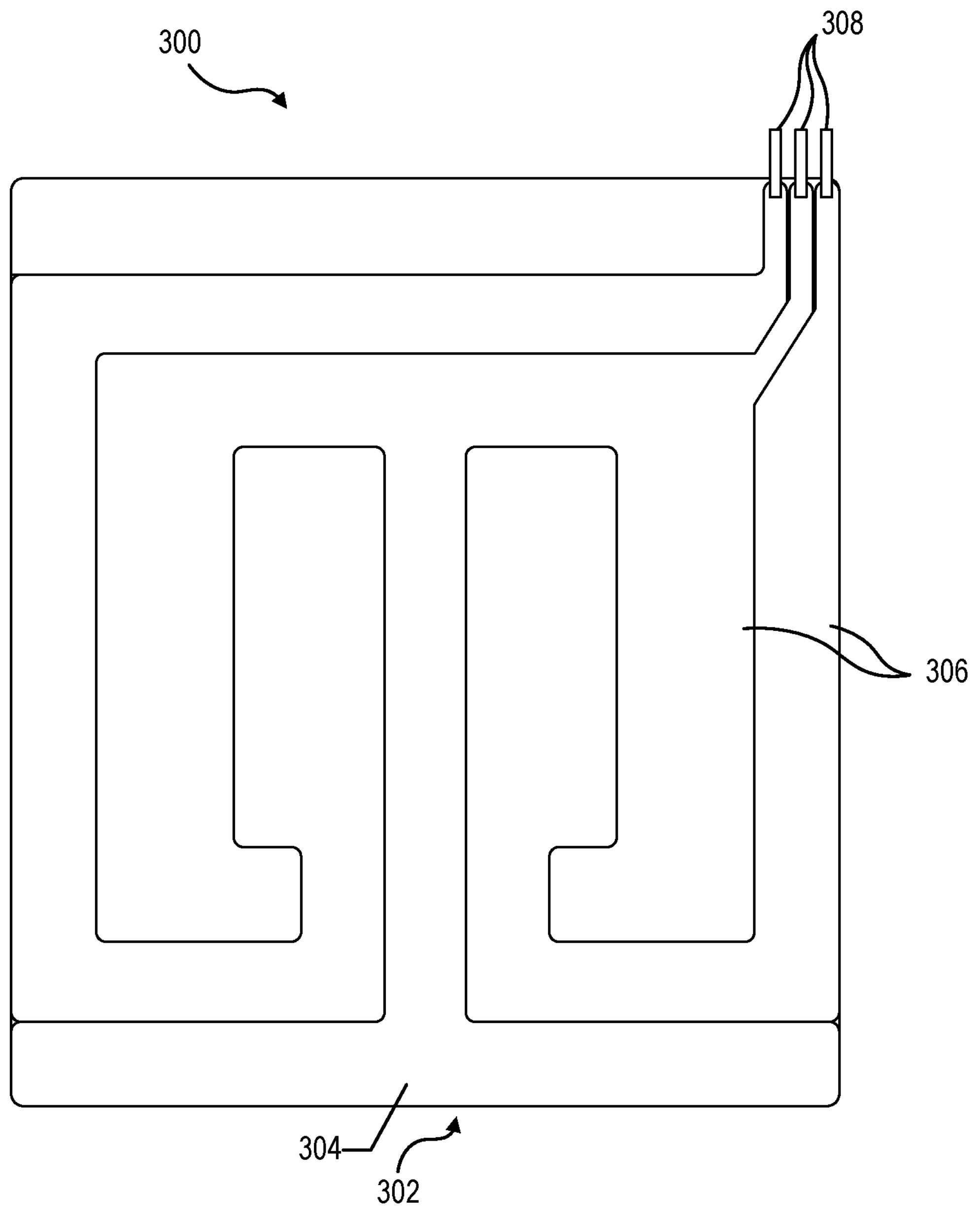
FIG. 3 is a top view of a pressure-mitigation device for relieving pressure on an anatomical region applied by a wheelchair in accordance with embodiments of the present technology.

FIG. 3 is a top view of a pressure-mitigation device 300 for relieving pressure on an anatomical region applied by a wheelchair in accordance with embodiments of the present technology. The pressure-mitigation device 300 can include features similar to the features of the pressure-mitigation device 200 of FIGS. 2A-B and the pressure-mitigation device 100 of FIGS. 1A-B described above. For example, the pressure-mitigation device 300 can include a first portion 302 (also referred to as a "first layer" or "bottom layer") designed to face the seat of the wheelchair, a second portion 304 (also referred to as a "second layer" or "top layer") designed to face the human body supported by the seat of the wheelchair, a series of chambers 306 formed by interconnections between the first and second portions 302, 304, and multiple valves 308 that control the flow of fluid into and/or out of the chambers 306. As can be seen in FIG. 3, the chambers 306 may be arranged similar to those shown in FIGS. 2A-B. Here, however, the pressure-mitigation device 300 is designed such that the valves 308 will be located near the backrest of the wheelchair. Such a design may allow the tubing connected to the valves 308 to be routed through a gap near, beneath, or in the backrest.

In some embodiments the first portion 302 is directly adjacent to the seat of the wheelchair, while in other embodiments the first portion 302 is directly adjacent to an attachment apparatus. As shown in FIG. 3, the pressure-mitigation device 300 may include an "M-shaped" chamber intertwined with a "U-shaped" chamber and a "C-shaped" chamber, which are inflated and deflated in accordance with a predetermined pattern to mitigate the pressure applied to the sacral region of a human body in a sitting position on the seat of a wheelchair. These chambers may be intertwined to collectively form a square-shaped pattern.

Figure 4A:
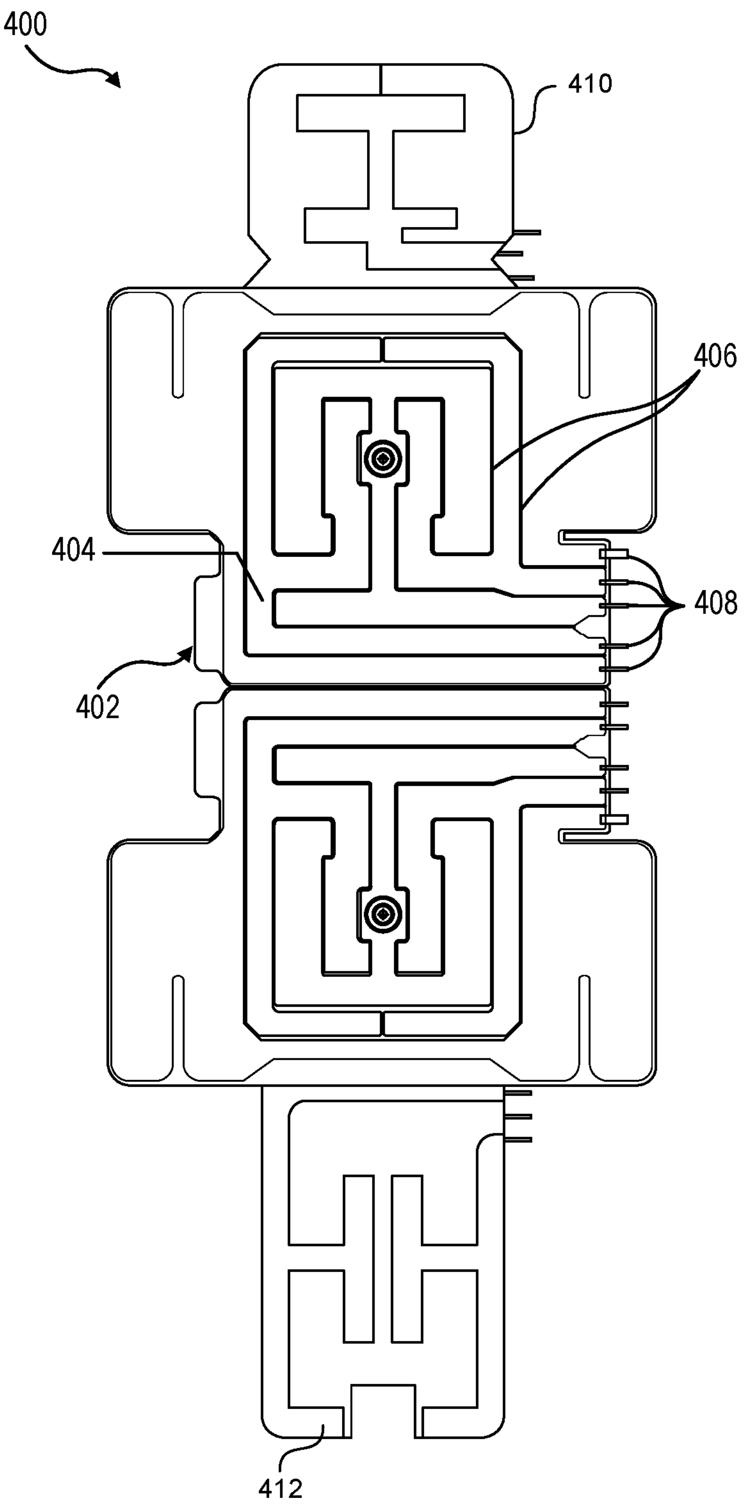
FIG. 4A is a top view of a pressure-mitigation device 400 for relieving pressure on an anatomical region applied by an elongated object in accordance with embodiments of the present technology.

FIG. 4A is a top view of a pressure-mitigation device 400 for relieving pressure on an anatomical region applied by an elongated object in accordance with embodiments of the present technology. As mentioned above, examples of elongated objects include mattresses, stretchers, operating tables, and procedure tables. The pressure-mitigation device 400 can include features similar to the features of the pressure-mitigation device 300 of FIG. 3, the pressure-mitigation device 200 of FIGS. 2A-B, and the pressure-mitigation device 100 of FIGS. 1A-B. For example, the pressure-mitigation device 400 can include a first portion 402 (also referred to as a "first layer" or "bottom layer") designed to face the surface of the elongated object, a second portion 404 (also referred to as a "second layer" or "top layer") designed to face a human body supported by the elongated object, a series of chambers 406 formed by interconnections between the first and second portions 402, 404, and multiple valves 408 that control the flow of fluid into and/or out of the chambers 406. As can be seen in FIG. 4A, the pressure-mitigation device 400 may be designed such that the valves 408 will be accessible along a longitudinal side of the elongated object. Such a design may allow the tubing connected to the valves 408 to be routed alongside the elongated object (e.g., along or through a handrail of a bedframe). Alternatively, the pressure-mitigation device may be designed such that the valves 408 are located near the top or bottom of the pressure-mitigation device 400 so as to allow the tubing to be routed along a latitudinal side of the elongated object.

While the pressure-mitigation device 100 of FIG. 1 is designed to occupy the lumbar, gluteal, and femoral regions while the human body positioned thereon is in the supine position, the pressure-mitigation device 400 of FIG. 4A can be designed to also occupy cervical, thoracic, and leg regions. Thus, the pressure-mitigation device 400 may be able to alleviate pressure applied by the elongated object anywhere along the posterior side of the human body between the skull and ankle.

Embodiments of the pressure-mitigation device 400 could also include (i) a cranial portion 410 (also referred to as a "cranial cushion" or "cranial cup") that is designed to envelop the posterior side of the cranium while the human body is in the supine position and/or (ii) a heel portion 412 (also referred to as a "heel cushion" or "heel cup") that is designed to envelop the posterior end of the foot while the human body is in the supine position. The cranial portion 410 and heel portion 412 may include a different number of chambers than the geometric arrangements designed to occupy the lumbar and femoral regions. Generally, the cranial portion 410 and heel portion 412 only include one or two chambers, though the cranial portion 410 and heel portion 412 could include more than two chambers. In embodiments where the pressure-mitigation device 400 includes cranial and heel portions, the pressure-mitigation device 400 may be referred to as a "full-body pressure-mitigation device." In embodiments where the pressure-mitigation device 400 includes cranial and heel portions, the pressure-mitigation device 400 may have a longitudinal form that is at least six feet in length. In embodiments where the pressure-mitigation device 400 does not include cranial and heel portions, the pressure-mitigation device 400 may have a longitudinal form that is at least four feet in length.

As shown in FIG. 4A, the pressure-mitigation device 400 can include side supports 414 that are able to actively or passively orient the human body with respect to the chambers of the pressure-mitigation device 400. In some embodiments, a single side support extends longitudinally along each opposing side of the pressure-mitigation device 400. In other embodiments, multiple side supports are located along each opposing side of the pressure-mitigation device 400. As an example, along each longitudinal side, the pressure-mitigation device 400 may include a first side support that is intended to be parallel to the thoracic region and a second side support that is intended to be parallel to the leg region. As another example, along each longitudinal side, the pressure-mitigation device 400 may include a first side support that is intended to be parallel to the thoracic and lumbar regions, a second side support that is intended to be parallel to the leg region, and a third side support that is intended to be parallel to the calf region. Accordingly, the pressure-mitigation device 400 may include more than one side support along each side, and each side support may be responsible for orienting a different anatomical region of the human body.

More generally, the pressure-mitigation device 400 includes a first geometric arrangement of a first series of chambers and a second geometric arrangement of a second series of chambers. When controllably inflated, the first series of chambers can relieve the pressure applied to a first anatomical region of a human body by an underlying surface. Similarly, when controllably inflated, the second series of chambers can relieve the pressure applied to a second anatomical region of the human body by the underlying surface. When the pressure-mitigation device 400 has a longitudinal form as shown in FIG. 4A, the first geometric arrangement can be longitudinally adjacent to the second geometric arrangement, so as to accommodate the first anatomical region that is superior to the second anatomical region. As shown in FIG. 4A, the second geometric arrangement may be representative of another instance of the first geometric arrangement that is mirrored across a latitudinal axis that is orthogonal to the longitudinal form of the pressure-mitigation device 400. Alternatively, the second geometric arrangement may be identical to the first geometric arrangement.

Moreover, the pressure-mitigation device may include a third geometric arrangement of a third series of chambers. When controllably inflated, the third series of chambers can relieve the pressure applied to a third anatomical region of the human body by the underlying surface. The third anatomical region may be superior to the anatomical region (e.g., when the third geometric arrangement corresponds to the cranial portion 410), or the third anatomical region may be inferior to the second anatomical region (e.g., when the third geometric arrangement corresponds to the heel portion 412).

As mentioned above, the pressure-mitigation device could include cranial and heel portions in some embodiments. Therefore, the pressure-mitigation device may include a third geometric arrangement of a third series of chambers and a fourth geometric arrangement of a fourth series of chambers. When controllably inflated, the third series of chambers can relieve the pressure applied to a third anatomical region of the human body by the underlying surface. Similarly, when controllably inflated, the fourth series of chambers can relieve the pressure applied to a fourth anatomical region of the human body by the underlying surface. The third anatomical region may be superior to the first anatomical region, while the fourth anatomical region may be inferior to the second anatomical region.

Figure 4B:
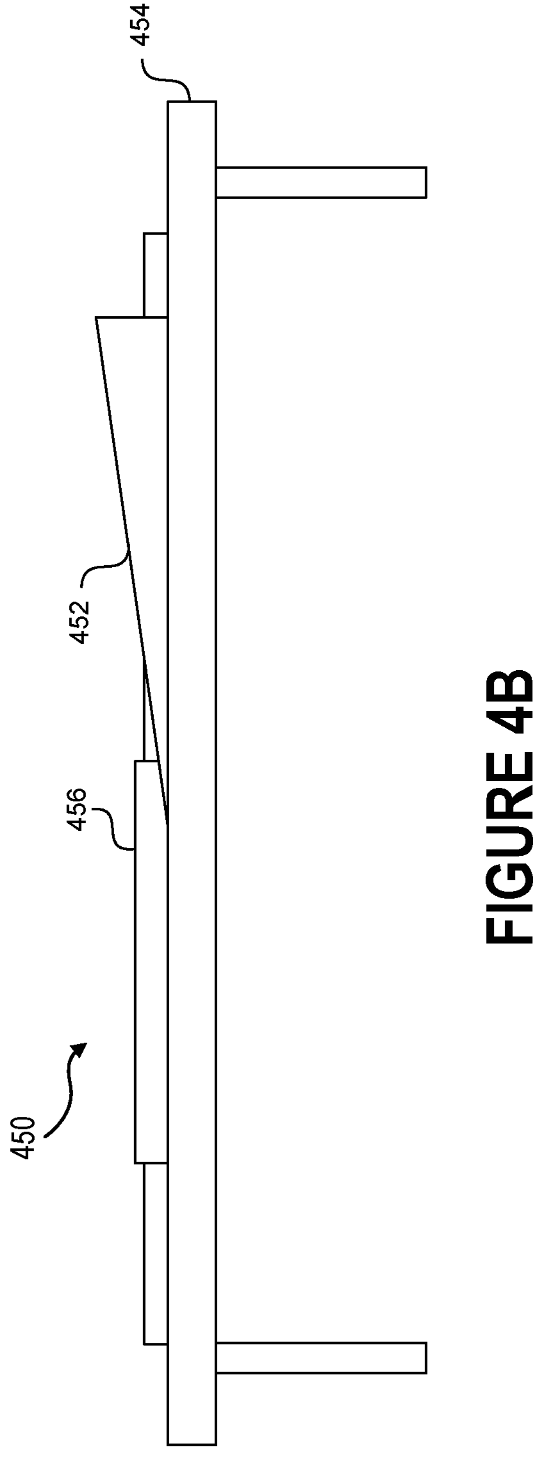
FIG. 4B is a side view of a pressure-mitigation device that is designed to alleviate pressure along one side of the human body by accommodating most, if not all, of that side of the human body.

FIG. 4B is a side view of a pressure-mitigation device 450 that is designed to alleviate pressure along one side of the human body by accommodating most, if not all, of that side of the human body. The pressure-mitigation device 450 of FIG. 4B could be similar to the pressure-mitigation device 400 of FIG. 4A. The pressure-mitigation device 450 of FIG. 4B includes a wedge portion 452, however. The wedge portion 452 may be interconnected along the upper surface of the pressure-mitigation device 450. As shown in FIG. 4B, the wedge portion 452 may be interconnected proximate to the second geometric arrangement of the second series of chambers, such that the second anatomical region (e.g., the gluteal region or femoral region) is elevated above the first anatomical region (e.g., the lumbar region) with respect to the surface.

As shown in FIG. 4B, the wedge portion 452 may be tapered such that the second anatomical region is increasingly separated from the surface as the distance to the first anatomical region increases. Such a feature can not only alter blood flow through the second anatomical region (and anatomical regions inferior to the second anatomical region)

but also naturally prevents migration of the human body toward the end of the pressure-mitigation device 450 that is nearer the second series of chambers.

Moreover, the wedge portion 452 may be continued to orient—either actively or passively—an anatomical region of the human body positioned on the pressure-mitigation device 450 lengthwise over the geometric pattern of chambers included in the pressure-mitigation device 450. For example, the wedge portion 452 could include one or more chambers that can be controllably inflated or deflated to actively orient the anatomical region of the human body over the geometric pattern of chambers. Alternatively, the wedge portion 452 may passively orient the anatomical region of the human body over the geometric pattern of chambers (e.g., by remaining constantly pressurized with fluid or filled with a substance, such as cotton, foam, gel, etc.). Thus, the wedge portion 452 may prevent migration of the human body toward the lower end of the pressure-mitigation device 450 (and the elongated object 454). In some embodiments, the wedge portion 452 is designed to work in conjunction with side supports 456 arranged on opposing sides of the pressure-mitigation device 450 to control the position of the human body placed thereon. The wedge portion 452 may inhibit longitudinal movement of the human body—especially towards the lower end of the pressure-mitigation device 450—while the side supports 456 may inhibit lateral movement of the human body. Together, the wedge portion 452 and side supports 456 can ensure that the pressure-mitigation device 450 is being used as intended by facilitating proper positioning of the human body with respect to the geometric pattern of chambers.

At a high level, the wedge portion 452 is intended to further separate the lower extremities from the surface of the elongated object 454 on which the pressure-mitigation device 450 is deployed. Thus, the wedge portion 452 may be designed to accommodate the lower extremities, such as the femoral, calf, or heel regions. Those skilled in the art will recognize that if the wedge portion 452 is designed to accommodate the heel region, then the pressure-mitigation device 450 may not need a separate heel portion as discussed above with reference to FIG. 4A. However, there may be situations where a heel portion is still desirable, for example, if the wedge portion 452 is detachable from the pressure-mitigation device 450.

As mentioned above, the wedge portion 452 may be able to actively orient the anatomical region of the human body over the geometric pattern of chambers in the pressure-mitigation device 450. For example, the wedge portion 450 may include one or more chambers that can be inflated and/or deflated to predetermined pressure levels. For example, the chamber(s) in the wedge portion 450 could be controllably inflated and/or deflated in accordance with a predetermined pattern that causes the lower extremities to be periodically lifted and lowered to varying degrees. The chamber(s) in the wedge portion 450 may alleviate pressure on the lower extremities much like the chambers in the pressure-mitigation device 450 alleviate pressure on other anatomical regions of the human body, though the chambers in the wedge portion 450 may be arranged in a different geometric pattern than the chambers in the pressure-mitigation device 450.

The chamber(s) included in the wedge portion 452 may form one or more channels for accommodating a portion of the legs of the human body. For example, embodiments of the pressure-mitigation device 450 can include two channels for accommodating both legs of the human body. Alternatively, embodiments of the pressure-mitigation device 450 may be designed to accommodate a single leg of the human body, and therefore may only include a single channel. In such embodiments, the wedge portion 452 may be sufficiently narrow that the other leg—which is not elevated—can remain in a naturally straight position. In some embodiments, the chamber(s) included in the wedge portion 452 can be designed or arranged so that when pressure is varied, force can be controllably applied to, and relieved from, the portion of the leg included in each channel.

Embodiments of the pressure-mitigation device 450 that include, or are connected to, a wedge portion 452 may be helpful in preventing or addressing various conditions. As an example, deep vein thrombosis (DVT) is a serious condition that occurs when a blood clot forms in a vein located deep inside the human body. These blood clots normally form in the thigh region or lower extremities but could also develop in other anatomical regions. One common cause of clotting is inactivity. If a human body does not move for an extended period of time, the blood flow through the legs will slow down, and this may cause a clot to develop. Another common cause of clotting is narrowing or blocking of vessels that obstruct the flow of blood. This damage tends to result from prolonged pressure on the surrounding anatomical region. Both of these causes can be addressed using the wedge portion 452. The wedge portion 452 can controllably vary (e.g., apply and then alleviate) pressure in a manner that is not susceptible to the development of blood clots.

Figure 4C:
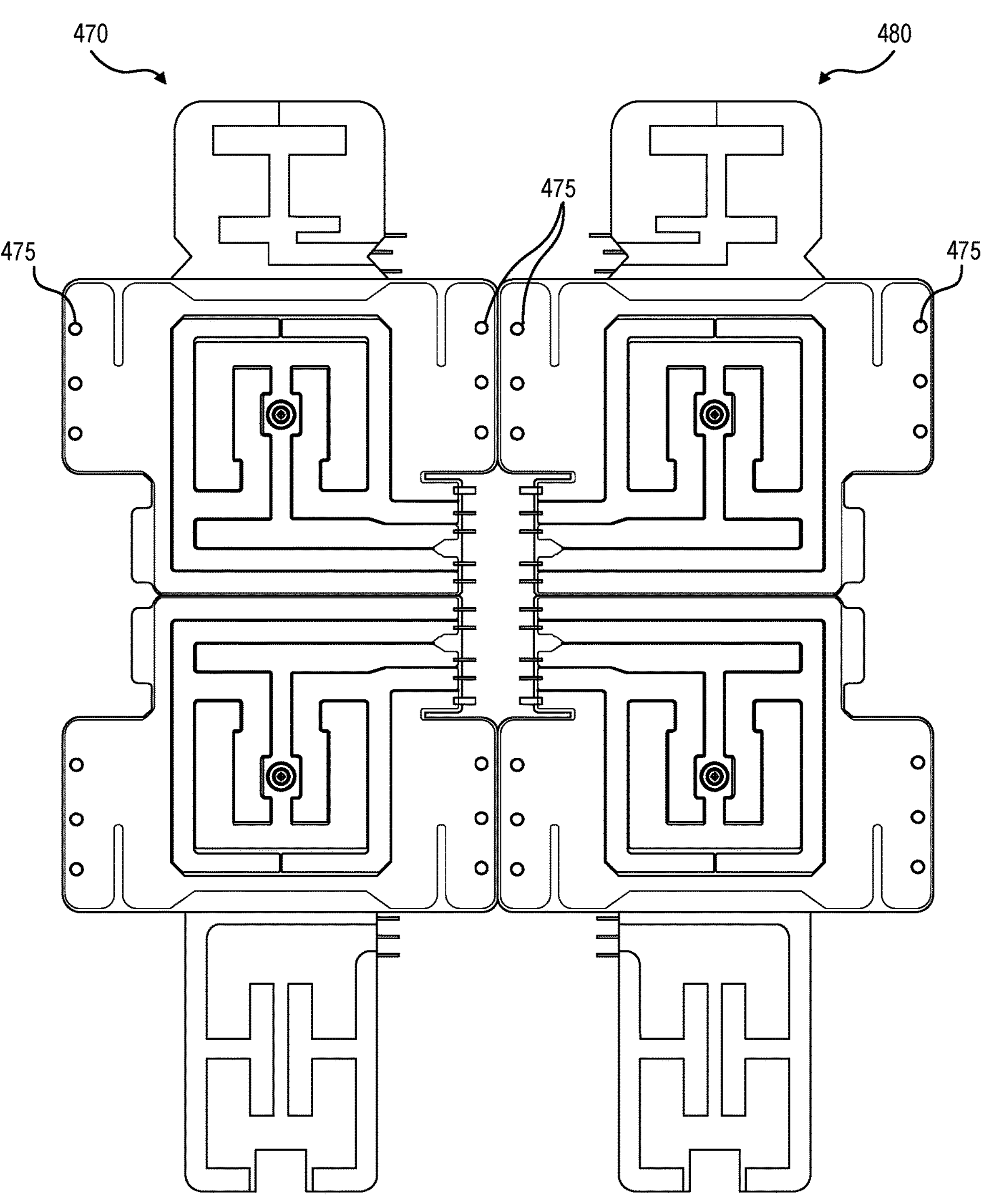
FIG. 4C illustrates how multiple pressure-mitigation devices can be connected to one another.

FIG. 4C illustrates how multiple pressure-mitigation devices 470, 480 can be connected to one another. Each type of pressure-mitigation device described above may be designed to be detachably connectable to the same type of pressure-mitigation device and/or a different type of pressure-mitigation device. For example, a pressure-mitigation device designed for non-elongated objects could be detachably connected alongside another pressure-mitigation device designed for non-elongated objects, or a pressure-mitigation device designed for non-elongated objects could be detachably connected alongside a pressure-mitigation device designed for elongated objects. Similarly, a pressure-mitigation device designed for elongated objects could be detachably connected alongside another pressure-mitigation device designed for elongated objects. Thus, multiple human bodies (e.g., related persons, such as a husband and wife) could be deployed alongside one another (e.g., in a single bed, in adjacent seats of a vehicle, etc.).

Pressure-mitigation devices can be detachably connected to one another using different forms of attachment mechanisms 475. As an example, a pressure-mitigation device may have a longitudinal form that is defined by opposing longitudinal sides, and the pressure-mitigation device may include at least one attachment mechanism along a first longitudinal side of the opposing longitudinal sides and at least one attachment mechanism along a second longitudinal side of the opposing longitudinal sides. The attachment mechanisms could be magnets, where the magnets arranged along the first longitudinal side have opposite polarity of the magnets arranged along the second longitudinal side. Specifically, magnets of one pole (e.g., north) may be located along one longitudinal side, while magnets of the other pole (e.g., south) may be located along the other longitudinal side. When pressure-mitigation devices are placed in proximity to one another, the magnets may naturally be attracted to one another. As another example, a pressure-mitigation device may include one or more mechanical structures, such as zippers, buttons, clasps, and the like, arranged along each longitudinal side. As another example, a pressure-mitigation device may include an adhesive film arranged along each longitudinal side. As another example, a pressure-mitigation device may include strips of hook-and-loop fasteners (e.g., made by VELCRO®) along each longitudinal side.

Assume that a pair of pressure-mitigation devices are to be secured to one another. In some embodiments, the pair of pressure-mitigation devices operate independently despite being detachably connected to one another. Thus, each pressure-mitigation device may be connected to its own controller. In other embodiments, the pair of pressure-mitigation devices operate together as a single unit. Thus, the pair of pressure-mitigation devices may be connected to a single controller that is responsible for controlling fluid flow into the chambers of each pressure-mitigation device. For example, multi-channel tubing that is connected to the controller may split along one end, and one split end may be fluidically coupled to a first pressure-mitigation device while another split end may be fluidically coupled to a second pressure-mitigation device. Such an approach allows the controller to simultaneously control the first and second pressure-mitigation devices.

Overview of Approaches to Mitigating Pressure

Figure 5:
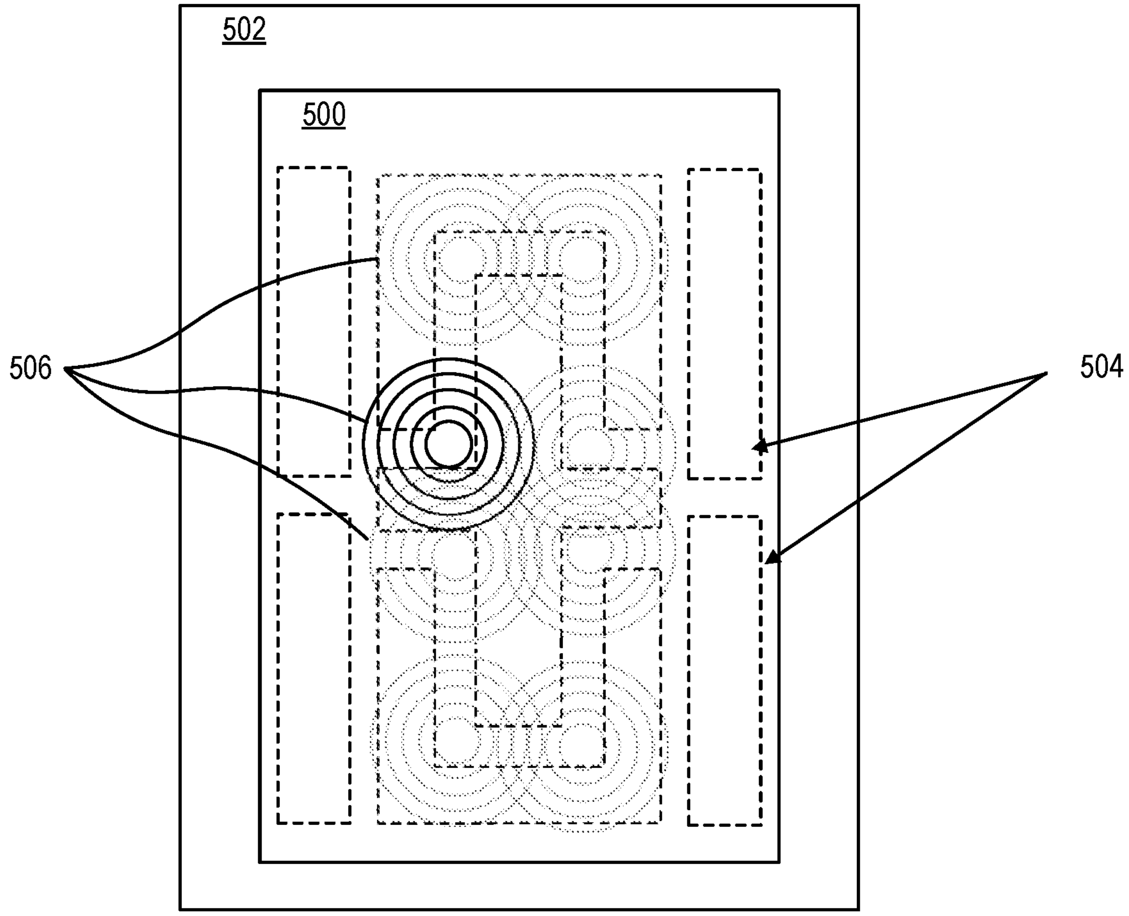
FIG. 5 is a partially schematic top view of a pressure-mitigation device illustrating how a pressure gradient can be created by varying pressure distributions to avoid ischemia in a mobility-impaired patient in accordance with embodiments of the present technology.

FIG. 5 is a partially schematic top view of a pressure-mitigation device 500 illustrating how a pressure gradient can be created by varying pressure distributions to avoid ischemia in a mobility-impaired patient in accordance with embodiments of the present technology. When a human body is supported by a surface 502 for an extended duration, pressure injuries may form in the tissue overlaying bony prominences, such as the skin overlying the sacrum, coccyx, heels, or hips. Generally, these bony prominences represent the locations at which the most pressure is applied by the surface 502 and, therefore, may be referred to as the "main pressure points" along the surface of the human body.

To prevent the formation of pressure injuries, healthy individuals periodically make minor positional adjustments (also known as "micro-adjustments") to shift the location of the main pressure point. However, individuals having impaired mobility often cannot make these micro-adjustments by themselves. Mobility impairment may be due to physical injury (e.g., a traumatic injury or a progressive injury), movement limitations (e.g., within a vehicle, on an aircraft, or in restraints), medical procedures (e.g., those requiring anesthesia), and/or other conditions that limit natural movement. For these mobility-impaired individuals, the pressure-mitigation device 500 can be used to shift the location of the main pressure point(s) on their behalf. That is, the pressure mitigation device 500 can create moving pressure gradients to avoid sustained, localized vascular compression and enhance tissue perfusion.

The pressure-mitigation device 500 can include a series of chambers 504 whose pressure can be individually varied. The chambers 504 may be formed by interconnections between the top and bottom layers of the pressure-mitigation device 500. The top layer may be comprised of a first material (e.g., a permeable, non-irritating material) configured for direct contact with a human body, while the bottom layer may be comprised of a second material (e.g., a non-permeable, gripping material) configured for direct contact with the surface 502. Generally, the first material is permeable to gasses (e.g., air) and/or liquids (e.g., water and sweat) to prevent buildup of fluids that may irritate the skin. Meanwhile, the second material may not be permeable to gasses or liquids to prevent soilage of the underlying object. Accordingly, air discharged into the chambers 504 may be able to slowly escape through the first material (e.g., naturally or via perforations) but not the second material, while liquids may be able to penetrate the first material (e.g., naturally or via perforations) but not the second material. Note, however, that the first material is generally be selected such that the top layer does not actually become saturated with liquid to reduce the likelihood of irritation. Instead, the top layer may allow liquid to pass therethrough into the cavities, from which the liquid can be subsequently discharged (e.g., as part of a cleaning process). The top layer and/or the bottom layer can be comprised of more than one material, such as a coated fabric or a stack of interconnected materials.

The pressure-mitigation device 500 may be designed such that inflation of at least some of the chambers 504 causes air to be continuously exchanged across the surface of the human body. Said another way, simultaneous inflation of at least some of the chambers 504 may provide a desiccating effect to inhibit generation and/or collection of moisture along the skin in a given anatomical region. In some embodiments, the pressure-mitigation device 500 is able to maintain airflow through the use of a porous material. For example, the top layer may be comprised of a biocompatible material through which air can flow (e.g., naturally or via perforations). In other embodiments, the pressure-mitigation device 500 is able to maintain airflow without the use of a porous material. For example, airflows can be created and/or permitted simply through varied pressurization of the chambers 504. This represents a new approach to microclimate management that is enabled by simultaneous inflation and deflation of the chambers 504. At a high level, each void formed beneath a human body due to deflation of at least one chamber can be thought of as a microclimate that cools and desiccates the corresponding portion of the anatomical region. Heat and humidity can lead to injury (e.g., further development of ulcers), so the cooling and desiccating effects may present some injuries due to inhibition of moisture generation/collection along the skin in the anatomical region.

As discussed below with respect to FIG. 20, a pump (also referred to as a "pressure device") can be fluidically coupled to each chamber 504 (e.g., via a corresponding valve), while a controller can control the flow of fluid generated by the pump into each chamber 504 on an individual basis in accordance with a predetermined pattern. The controller can operate the series of chambers 504 in several different ways.

In some embodiments, the chambers 504 have a naturally deflated state, and the controller causes the pump to inflate at least one of the chambers 504 to shift the main pressure point along the anatomy of the human body. For example, the pump may inflate at least one chamber located directly beneath an anatomical region to momentarily apply contact pressure to that anatomical region and relieve contact pressure on the surrounding anatomical regions adjacent to the deflated chamber(s). Alternatively, the controller may cause the pump to inflate two or more chambers adjacent to an anatomical region to create a void beneath the anatomical region to shift the main pressure point at least momentarily away from the anatomical region.

In other embodiments, the chambers 504 have a naturally inflated state, and the controller may cause deflation of at least one of the chambers 504 to shift the main pressure point along the anatomy of the human body. For example, the pump may cause deflation of at least one chamber located directly beneath an anatomical region, thereby forming a void beneath the anatomical region to momentarily relieve the contact pressure on the anatomical region. To deflate a chamber, the controller may simply prevent an airflow generated by the pump from entering the chamber as further discussed below with reference to FIGS. 9-10. Additionally or alternatively, the controller may cause air contained in the chamber to be released (e.g., via a release valve). At least partial deflation may naturally occur in this scenario if air escapes through the valve quicker than air enters the chamber.

Whether configured in a naturally deflated state or a naturally inflated state, the continuous or intermittent alteration of the inflation levels of the individual chambers 504 moves the location of the main pressure point across different portions of the human body. As shown in FIG. 5, for example, inflating and/or deflating the chambers 504 creates temporary contact regions 506 that move across the pressure-mitigation device 500 in a predetermined pattern, and thereby changing the location of the main pressure point(s) on the human body for finite intervals of time. Thus, the pressure-mitigation device 500 can simulate the micro-adjustments made by healthy individuals to relieve stagnant pressure applied by the surface 502.

The series of chambers 504 may be arranged in an anatomy-specific pattern so that when the pressure of one or more chambers is altered, the contact pressure on a specific anatomical region of the human body is relieved (e.g., by shifting the main pressure point elsewhere). As an example, the main pressure point may be moved between eight different locations corresponding to the eight temporary contact regions 506 as shown in FIG. 5. In some embodiments the main pressure point shifts between these locations in a predictable manner (e.g., in a clockwise or counter-clockwise pattern), while in other embodiments the main pressure point shifts between these locations in an unpredictable manner (e.g., in accordance with a random pattern or a semi-random pattern, based on the amount of force applied by the human body to the chambers, or based on the pressure of the chambers). Those skilled in the art will recognize that the number and position of these temporary contact regions 506 may vary based on the size of the pressure-mitigation device 500, the arrangement of chambers 504, the number of chambers 504, the anatomical region supported by the pressure-mitigation device 500, the characteristics of the human body supported by the pressure mitigation device 500, the condition of the human body (e.g., whether the person is completely immobilized, partially immobilized, etc.), or any combination thereof.

As discussed above, the pressure-mitigation device 500 may not include side supports if the condition of a user would not benefit from the positioning assistance provided by the side supports. For example, side supports can be omitted when the user is medically immobilized (e.g., under anesthesia, in a medically induced coma, etc.) and/or physically restrained on the underlying surface 502 (e.g., by rails on the side of a bed, arm rests on the side of a chair, restraints that limit movement, etc.).

Figure 6A:
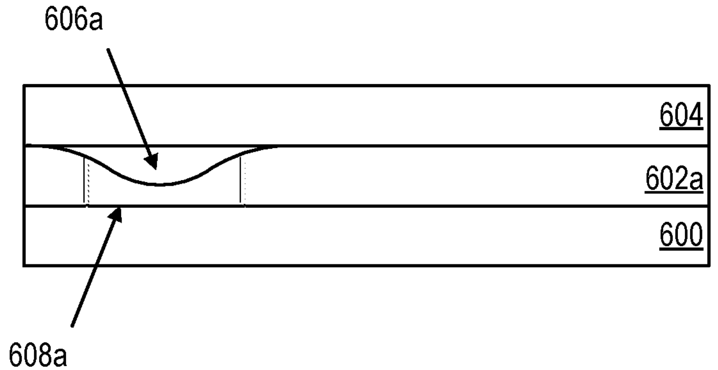
FIG. 6A is a partially schematic side view of a pressure-mitigation device for relieving pressure on a specific anatomical region by deflating one or more chambers in accordance with embodiments of the present technology.

FIG. 6A is a partially schematic side view of a pressure-mitigation device 602*a* for relieving pressure on a specific anatomical region by deflating one or more chambers in accordance with embodiments of the present technology. The pressure-mitigation device 602*a* can be positioned between the surface of an object 600 and a human body 604. Examples of objects 600 include elongated objects, such as mattresses, stretchers, operating tables, and procedure tables, and non-elongated objects, such as chairs (e.g., office chairs, examination chairs, recliners, and wheelchairs) and the seats included in vehicles and airplanes. To relieve the pressure on a specific anatomical region of the human body 604, at least one chamber 608*a* of multiple chambers (collectively referred to as "chambers 608") proximate to the specific anatomical region is at least partially deflated to create a void 606*a* beneath the specific anatomical region. In such embodiments, the remaining chambers 608 may remain inflated. Thus, the pressure-mitigation device 602*a* may sequentially deflate chambers (or arrangements of multiple chambers) to relieve the pressure applied to the human body 604 by the surface of the object 600.

Figure 6B:
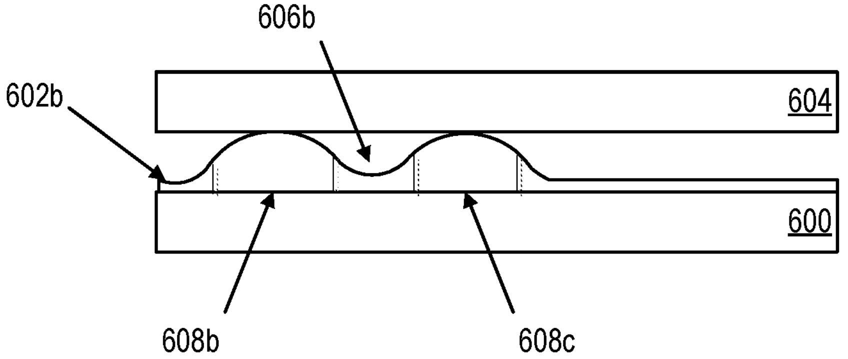
FIG. 6B is a partially schematic side view of a pressure-mitigation device for relieving pressure on a specific anatomical region by inflating one or more chambers in accordance with embodiments of the present technology.

FIG. 6B is a partially schematic side view of a pressure-mitigation device 602*b* for relieving pressure on a specific anatomical region by inflating one or more chambers in accordance with embodiments of the present technology. For example, to relieve the pressure on a specific anatomical region of the human body 604, the pressure-mitigation device 602*b* can inflate two chambers 608*b* and 608*c* disposed directly adjacent to the specific anatomical region to create a void 606*b* beneath the specific anatomical region. In such embodiments, the remaining chambers may remain partially or entirely deflated. Thus, the pressure-mitigation device 602*b* may sequentially inflate a chamber (or arrangements of multiple chambers) to relieve the pressure applied to the human body 604 by the surface of the object 600.

The pressure-mitigation devices 602*a*, 602*b* of FIGS. 6A-B are shown to be in direct contact with the contact surface 600. However, in some embodiments, an attachment apparatus is positioned between the pressure-mitigation devices 602*a*, 602*b* and the object 600. The attachment apparatus may be designed to help secure the pressure-mitigation devices 602*a*, 602*b* and the object 600. For example, the attachment apparatus may be made of a material that is naturally tacky or sticky so as to inhibit movement of the pressure-mitigation devices 602*a*, 602*b* with respect to the object 600. Alternatively, the bottom side of the pressure-mitigation devices 602*a*, 602*b* could be coated with a material, such as a removable adhesive (e.g., an elastomer- or silicone-based sealant or a pressure-sensitive film) or tacky substance (e.g., silicone rubber).

In some embodiments, the pressure-mitigation devices 602*a*, 602*b* of FIGS. 6A-B have the same configuration of chambers 608, and can operate in both a normally inflated state (described with respect to FIG. 6A) and a normally deflated state (described with respect to FIG. 6B) based on the selection of an operator (e.g., the user or some other person, such as a healthcare professional or family member). For example, the operator can use a controller to select a normally deflated mode such that the pressure-mitigation device operates as described with respect to FIG. 6B, and then change the mode of operation to a normally inflated mode such that the pressure-mitigation device operates as described with respect to FIG. 6A. Thus, the pressure-mitigation devices described herein can shift the location of the main pressure point by controllably inflating chambers, controllably deflating chambers, or a combination thereof.

Overview of Controller Devices

Figure 7A:
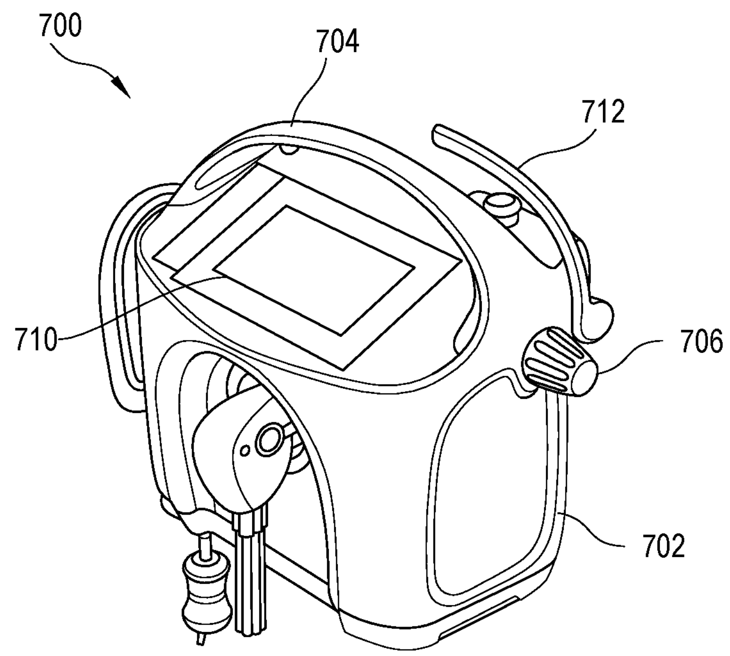
FIGS. 7A-C are isometric, front, and back views, respectively, of a controller device (also referred to as a "controller") that is responsible for controlling inflation and/or deflation of the chambers of a pressure-mitigation device in accordance with embodiments of the present technology.
Figure 7B:
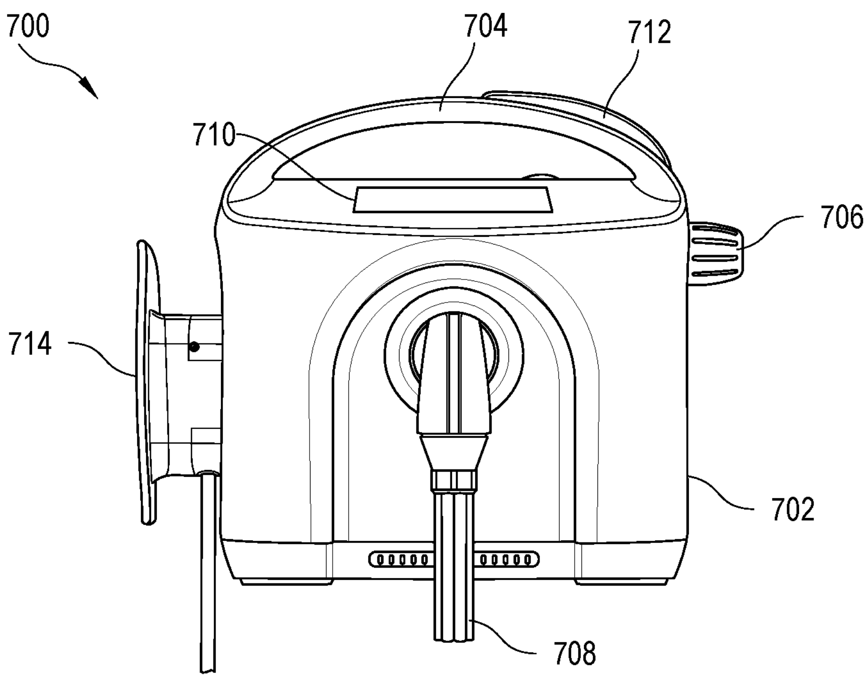
Figure 7C:
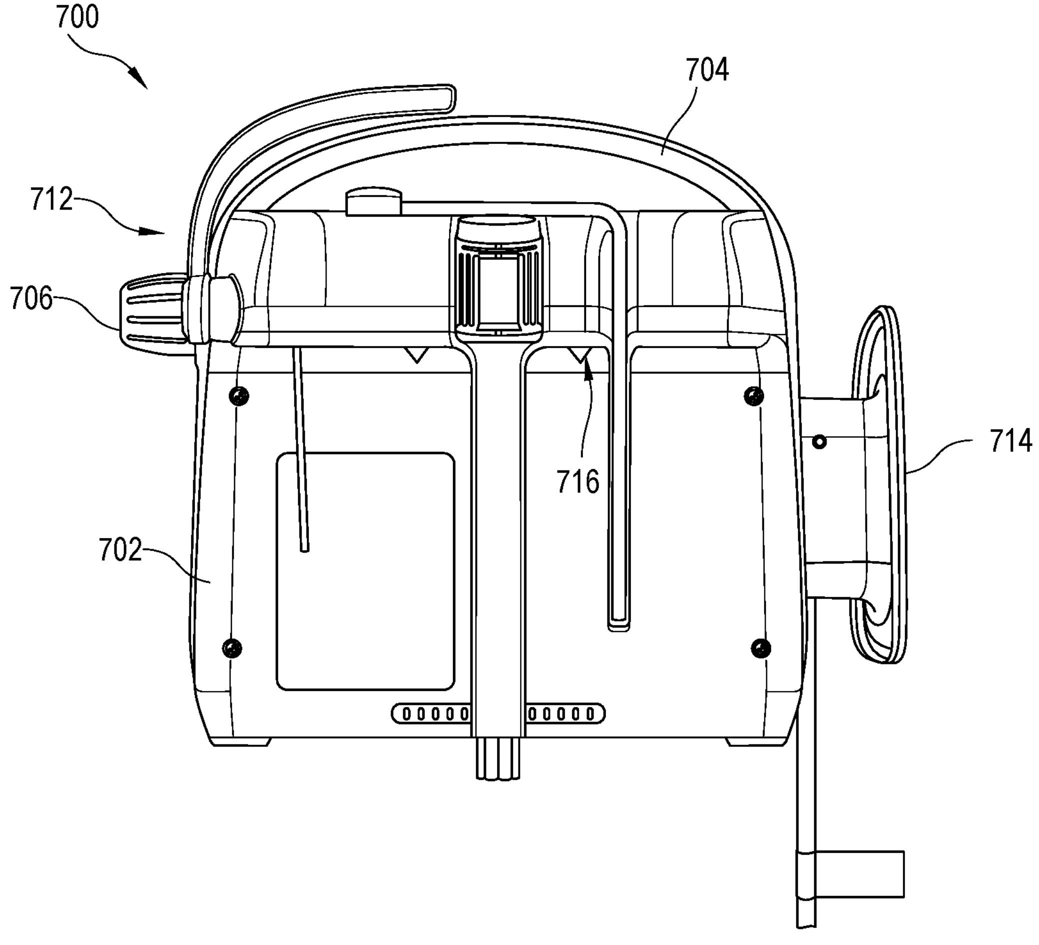

FIGS. 7A-C are isometric, front, and back views, respectively, of a controller device 700 (also referred to as a "controller") that is responsible for controlling inflation and/or deflation of the chambers of a pressure-mitigation device in accordance with embodiments of the present technology. For example, the controller 700 can be coupled to the pressure-mitigation devices 100, 200, 300, 400 described above with respect to FIGS. 1A-4B to control the pressure within the chambers 106, 206, 306, 406. The controller 700 can manage the pressure in each chamber of a pressure-mitigation device by controllably driving one or more pumps. In some embodiments, a single pump is fluidically connected to all the chambers such that the pump is responsible for directing fluid flow to and/or from multiple chambers. In other embodiments, the controller 700 is coupled to two or more pumps, each of which can be fluidically coupled to a single chamber to drive inflation/deflation of that chamber. In other embodiments, the controller 700 is coupled to at least one pump that is fluidically coupled to two or more chambers and/or at least one pump that is fluidically coupled to a single chamber. The pump(s) may reside within the housing of the controller 700 such that the system is easily transportable. Alternatively, the pump(s) may reside in a housing separate from the controller 700.

As shown in FIGS. 7A-C, the controller 700 can include a housing 702 in which internal components (e.g., those described below with respect to FIG. 8) reside and a handle 704 that is connected to the housing 702. In some embodiments the handle 704 is fixedly secured to the housing 702 in a predetermined orientation, while in other embodiments the handle 704 is pivotably secured to the housing 702. For example, the handle 704 may be rotatable about a hinge connected to the housing 702 between multiple positions. The hinge may be one of a pair of hinges connected to the housing 702 along opposing lateral sides. The handle 704 enables the controller 700 to be readily transported, for example, from a storage location to a deployment location (e.g., proximate a human body that is positioned on a surface). Moreover, the handle 704 could be used to releasably attach the controller 700 to a structure. For example, the handle 704 could be hooked on an intravenous (IV) pole (also referred to as an "IV stand" or "infusion stand").

In some embodiments, the controller 700 includes a retention mechanism 714 that is attached to, or integrated within, the housing 702. Cords (e.g., electrical cords), tubes, and/or other elongated structures associated with the system can be wrapped around or otherwise supported by the retention mechanism 714. Thus, the retention mechanism 714 may provide strain relief and retention of an electrical cord (also referred to as a "power cord"). In some embodiments, the retention mechanism 714 includes a flexible flange that can retain the plug of the electrical cord.

As further shown in FIGS. 7A-C, the controller 700 may include a connection mechanism 712 that allows the housing 702 to be securely, yet releasably, attached to a structure. Examples of structures include IV poles, mobile workstations (also referred to as "mobile carts"), bedframes, rails, handles (e.g., of wheelchairs), and tables. The connection mechanism 712 may be used instead of, or in addition to, the handle 704 for mounting the controller 700 to the structure. In the illustrated embodiment, the connection mechanism 712 is a mounting hook that allows for single-hand operation and is adjustable to allow for attachment to mounting surfaces with various thicknesses. In some embodiments, the controller 700 includes an IV pole clamp 716 that eases attachment of the controller 700 to IV poles. The IV pole clamp 716 may be designed to enable quick securement, and the IV pole clamp 616 can be self-centering with the use of a single activation mechanism (e.g., knob or button).

In some embodiments, the housing 702 includes one or more input components 706 for providing instructions to the controller 700. The input component(s) 706 may include knobs (e.g., as shown in FIGS. 7A-C), dials, buttons, levers, and/or other actuation mechanisms. An operator can interact with the input component(s) 706 to alter the airflow provided to the pressure-mitigation device, discharge air from the pressure-mitigation device, or disconnect the controller 700 from the pressure-mitigation device (e.g., by disconnecting the controller 700 from tubing connected between the controller 700 and pressure-mitigation device).

As further discussed below, the controller 700 can be configured to inflate and/or deflate the chambers of a pressure-mitigation device in a predetermined pattern by managing one or more flows of fluid (e.g., air) produced by one or more pumps. In some embodiments the pump(s) reside in the housing 702 of the controller 700, while in other embodiments the controller 700 is fluidically connected to the pump(s). For example, the housing 702 may include a first fluid interface through which fluid is received from the pump(s) and a second fluid interface through which fluid is directed to the pressure-mitigation device. Multi-channel tubing may be connected to either of these fluid interfaces. For example, multi-channel tubing may be connected between the first fluid interface of the controller 700 and multiple pumps. As another example, multi-channel tubing may be connected between the second fluid interface of the controller 700 and multiple valves of the pressure-mitigation device. Here, the controller 700 includes a fluid interface 708 designed to interface with multi-channel tubing. In some embodiments the multi-channel tubing permits unidirectional fluid flow, while in other embodiments the multi-channel tubing permits bidirectional fluid flow. Thus, fluid returning from the pressure-mitigation device (e.g., as part of a discharge process) may travel back to the controller 700 through the second fluid interface. By controlling the exhaust of fluid returning from the pressure-mitigation device, the controller 700 can actively manage the noise created during use.

By monitoring the connection with the fluid interface 708, the controller 700 may be able to detect which type of pressure-mitigation device has been connected. Each type of pressure-mitigation device may include a different type of connector. For example, a pressure-mitigation device designed for elongated objects (e.g., the pressure-mitigation device 100 of FIGS. 1A-B, pressure-mitigation device 400 FIG. 4A, pressure-mitigation device 450 of FIG. 4B) may include a first arrangement of magnets in its connector, while a pressure-mitigation device designed for non-elongated objects (e.g., the pressure-mitigation device 200 of FIGS. 2A-B or pressure-mitigation device 300 of FIG. 3) may include a second arrangement of magnets in its connector. The controller 700 may include one or more sensors arranged near the fluid interface 708 that are able to detect whether magnets are located within a specified proximity. The controller 700 may automatically determine, based on which magnets have been detected by the sensor(s), which type of pressure-mitigation device is connected.

Pressure-mitigation devices may have different geometries, layouts, and/or dimensions suitable for various positions (e.g., supine, prone, sitting), various supporting objects (e.g., wheelchair, bed, recliner, surgical table), and/or various user characteristics (e.g., weight, size, ailment), and the controller 700 can be configured to automatically detect the type of pressure-mitigation device connected thereto. In some embodiments, the automatic detection is performed using other suitable identification mechanisms, such as the controller 700 reading a radio-frequency identification (RFID) tag or barcode on the pressure-mitigation device. Alternatively, the controller 700 may permit an operator to specify the type of pressure-mitigation device connected thereto. For example, the operator may be able to select, using an input component (e.g., input component 706), a type of pressure-mitigation device via a display 710. The controller 700 can be configured to dynamically alter the pattern for inflating and/or deflating chambers based on which type of pressure-mitigation device is connected.

As shown in FIGS. 7A-B, the controller 700 may include a display 710 for displaying information related to the pressure-mitigation device, the pattern of inflations/deflations, the user, etc. For example, the display 710 may present an interface that specifies which type of pressure-mitigation device is connected to the controller 700. As another example, the display 710 may present an interface that specifies the programmed pattern that is presently governing inflation/deflation of the pressure-mitigation device, as well as the current state within the programmed pattern. Other display technologies could also be used to convey information to an operator of the controller 700. In some embodiments, the controller 700 includes a series of lights (e.g., light-emitting diodes) that are representative of different statuses to provide visual alerts to the operator or the user. For example, a status light may provide a green visual indication if the controller 700 is presently providing therapy, a yellow visual indication if the controller 700 has been paused (i.e., is in a pause mode), a red visual indication if the controller 700 has experienced an issue (e.g., non-compliance of patient, patient not detected) or requires maintenance (i.e., is in an alert mode), etc. These visual indications may dim upon the conclusion of a specified period of time or upon determining that the status has changed (e.g., the pause mode is no longer active).

In some embodiments, the controller 700 includes a rapid deflate function that allows an operator to rapidly deflate the pressure-mitigation device. The rapid deflate function may be designed such that the entire pressure-mitigation device is deflated or a portion (e.g., the side supports) of the pressure-mitigation device is deflated. This may be a software-implemented solution that can be activated via the display 710 (e.g., when configured as a touch-enabled interface) and/or input components (e.g., tactile actuators such as buttons, switches, etc.) on the controller 700. This rapid deflation, in particular the deflation of the side supports, is expected to be beneficial to operators when there is a need for quick access to the user, such as to provide cardiopulmonary resuscitation (CPR).

Figure 8:
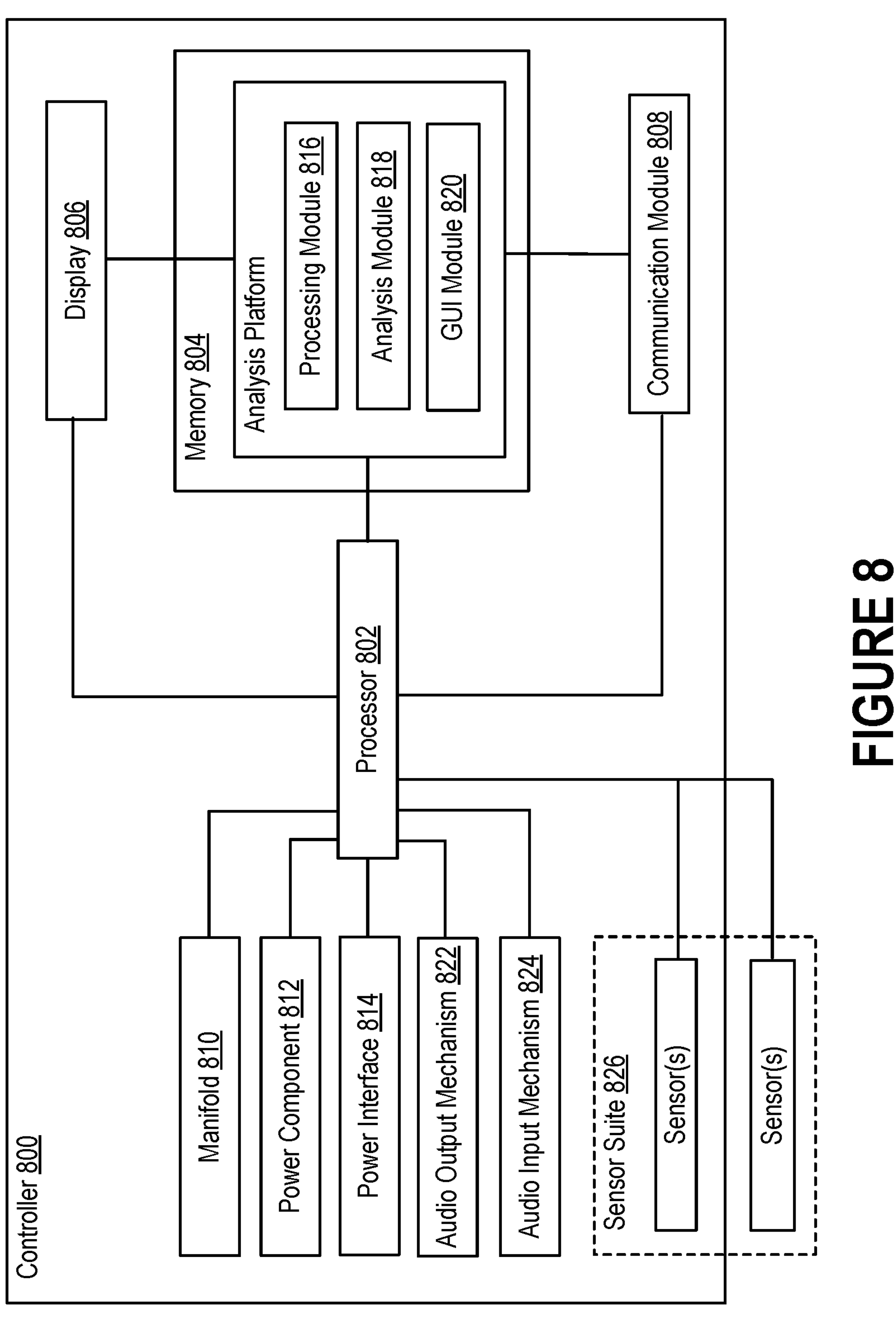
FIG. 8 illustrates an example of a controller in accordance with embodiments of the present technology.

FIG. 8 illustrates an example of a controller 800 in accordance with embodiments of the present technology. As shown in FIG. 8, the controller 800 can include a processor 802, memory 804, display 806, communication module 808, manifold 810, and/or power component 812 that is electrically coupled to a power interface 814. These components may reside within a housing (also referred to as a "structural body"), such as the housing 702 described above with respect to FIGS. 7A-C. In some embodiments, the aspects of the controller 800 are incorporated into other components of a pressure-mitigation system. For example, some components of the controller 800 may be incorporated into a computing device (e.g., a mobile phone or a mobile workstation) that is remotely coupled to a pressure-mitigation device. As another example, some components of the controller 800 may be incorporated into the pressure-mitigation device itself. While "integrated" pressure-mitigation devices are more costly to produce due to the additional components, there can be significant savings in terms of space and logistics, as a separate controller and tubing may not be necessary.

Each of these components is discussed in greater detail below. Those skilled in the art will recognize that different combinations of these components may be present depending on the nature of the controller 800. Other components could also be included depending on the desired capabilities of the controller 800.

For example, the controller 800 could include one or more dispensing mechanisms that are able to selectively dispense fluid from a reservoir. The fluid could be water, in which case dispensation might increase the ambient humidity. Alternatively, the fluid could be scented, thereby allowing the controller 800 to operate as an aromatherapy device. Such a feature may be desirable if the pressure-mitigation device is intended to be used as part of a therapy program. In embodiments where the fluid is scented, the dispensing mechanisms may be referred to as "fragrance output mechanisms that are able to discharge scented fluid (e.g., air or liquid) from corresponding reservoirs, so as to produce an aroma. Each dispensing mechanism can include (i) a pump that is able to selectively dispense the scented fluid from a corresponding reservoir and (ii) a nozzle through which the scented fluid is dispensed. In operation, the processor 802 can transmit signals to the dispensing mechanisms, so as to cause the scented fluid to be dispensed into the ambient environment. In embodiments where the controller 800 includes multiple dispensing mechanism, the processor 802 may transmit multiple signals to the multiple dispensing mechanisms, to indicate to each dispensing mechanism how much scented fluid to dispense. In some embodiments, the pattern for dispensing scented fluid is based on the programmed pattern that governs how to inflate the chambers of the pressure-mitigation device. For example, the programmed pattern may include frames that define when signals are to be transmitted to the dispensing mechanisms. Note that each signal may not only specify the amount of scented fluid to be dispensed, but also the interval of time over which the scented fluid is to be dispensed. The scented fluid can take several different forms. In some embodiments, the scented fluid is a liquid that is dispensed in the form of a spray. In other embodiments, the scented fluid is an aerosol that is enclosed in the reservoir under pressure and dispensed by the corresponding dispensing mechanism as a spray by means of a propellant gas. The controller 800 could include a single reservoir in which scented fluid is stored, or the controller 800 could include multiple reservoirs in which scented fluids are stored. Normally, each reservoir of the multiple reservoir includes a different scented fluid, though this need not be the case. Further, each reservoir may correspond with a dispensing mechanism that is responsible for controlling dispensation of the scented fluid therefrom. In some embodiments, the number of dispensing mechanisms corresponds to the number of reservoirs. In other embodiments, at least one dispensing mechanisms is shared among multiple reservoirs. Thus, the controller 800 may only have a single dispensing mechanism even if there are multiple reservoirs storing different scented fluids. To ensure reusability, the reservoirs may be readily removable from the controller 800. For example, the controller 800 may include a hinged door that when opened, reveals a compartment in which the reservoirs are held.

As another example, the controller 800 could include a fan that is configured to generate an airflow. Often, a fan is included in embodiments where the controller 800 includes dispensing mechanisms for dispensing fluid, either scented or unscented, in order to promote dispersion of the fluid throughout the ambient environment. However, a fan could be included in embodiments where the controller 800 does not include any dispensing mechanisms. In such a scenario, the fan may be positioned and oriented so that the airflow is directed toward the user of the pressure-mitigation device.

As another example, the controller could include circuitry (also called "detecting circuitry" or a "detecting circuit") that is able to detect and then examine electronic signatures emitted by nearby sources. One example of a source is a radio transmitter (also called a "beacon") that is configured to continually or periodically broadcast its identifier to nearby computing device. The signal that is representative of the identifier may be referred to as an "electronic signature" that identifies the beacon, and therefore whatever object the beacon is part of. Specifically, the detecting circuit may monitor for electronic signatures emitted by nearby beacons and, in response to detecting an electronic signature, transmit a signal to the processor 802 to prompt further action. Accordingly, if an item (e.g., a wristband, file, or computing device) that includes a beacon is presented to the controller 800, the controller 800 may be able to detect the electronic signature emitted by the beacon and then take appropriate action. For example, the processor 802 may determine whether to authorize use of the controller 800 based on an analysis of the electronic signature. As another example, the processor 802 may derive information regarding the human body to be treated based on an analysis of the electronic signature and then adjust the programmed pattern—which indicates how to inflate the chambers of the pressure-mitigation device—based on the information derived from the electronic signature. Thus, the controller 800 may determine, based on the electronic signature that conveys information regarding the human body to be treated, how to inflate the chambers of the pressure-mitigation device. Electronic signatures may be transmitted via RFID, Bluetooth®, Wi-Fi®, Near Field Communication (NFC), or another short-range wireless communication protocol. In addition to being used to convey information, electronic signatures may simply be used as a means of identifying a source from which to receive information or a destination to which to transmit information. Assume, for example, that the controller 800 receives input indicative of a request to inflate the chambers of a pressure-mitigation device in accordance with a programmed pattern. In such a scenario, the controller 800 may monitor for electronic signatures that are broadcast by nearby beacons. Upon identifying an electronic signature that is representative of a computing device, the controller 800 may establish a wireless communication channel with the computing device. As further discussed below, the wireless communication channel could be used to receive information from, and transmit information to, the computing device.

As another example, the controller 800 could include an image sensor that is configured to produce digital images based on the light that is reflected by objects in a field of view and collected through a lens. Digital images could be produced continually, or digital images could be produced periodically, for example, in response to determining that an object is located within a certain proximity of the image sensor in its field of view. The processor 802 can be configured to review the digital images to determine whether any include content of interest. For example, the processor 802 may determine that a digital image includes an object that is presented to the image sensor for the purpose of identifying the human body to be treated with the pressure-mitigation apparatus. In such a scenario, the processor 802 may derive information regarding the human body based on an analysis of the digital image. In some cases, the object may include human-readable characters that convey the information. For example, the object may be a paper that includes information such as the user's name, weight, age, and the like. In other cases, the object may include a machine-readable code from which the information is derivable. For example, the processor 802 may be able to examine Quick Response codes (also called "QR codes"), bar codes, and alphanumeric strings that are printed on items such as wristbands, files, and the like. By examining the machine-readable code that is printed on an object associated with a human body, the controller may be able to determine, infer, or derive information regarding the human body. These features allow the controller 800 to act as a "single action" solution for treating the human body since the controller may automatically begin treatment after an electronic signature or machine-readable code has been presented. Accordingly, the controller 800 may not only initiate treatment in response to deriving user-related information from a digital image, but could also adjust the programmed pattern for inflating the chambers of the pressure-mitigation device based on the user-related information.

The processor 802 can have generic characteristics similar to general-purpose processors, or the processor 802 may be an application-specific integrated circuit (ASIC) that provides control functions to the controller 800. As shown in FIG. 8, the processor 802 can be coupled to all components of the controller 800, either directly or indirectly, for communication purposes.

The memory 804 may be comprised of any suitable type of storage medium, such as static random-access memory (SRAM), dynamic random-access memory (DRAM), electrically erasable programmable read-only memory (EEPROM), flash memory, or registers. In addition to storing instructions that can be executed by the processor 802, the memory 804 can also store data generated by the processor 802 (e.g., when executing the analysis platform 216). Note that the memory 204 is merely an abstract representation of a storage environment. The memory 204 could be comprised of actual memory chips or modules.

The display 806 can be any mechanism that is operable to visually convey information to an operator. For example, the display 806 may be a panel that includes LEDs, organic LEDs, liquid crystal elements, or electrophoretic elements as shown in FIGS. 7A-B. Alternatively, the display 806 may simply be a series of lights (e.g., LEDs) that are able to indicate the status of the controller 800. In some embodiments, the display 806 is touch sensitive. Thus, an operator user may be able to provide input to the controller 800 by interacting with the display 806 itself. Additionally or alternatively, the operator may be able to provide input to the controller 800 by interacting with input components, such as knobs, dials, buttons, levers, and/or other actuation mechanisms.

Various types of information can be presented by the display 806. For example, information related to the state of the pressure-mitigation device and/or programmed pattern could be presented on the display 806, so as to indicate progression. As another example, information regarding the human body situated on the pressure-mitigation device could be presented on the display 806. Said another way, information related to the user may be presented on the display 806. The user-related information could be obtained through an analysis of an electronic signature that is detected by the controller 800, or the user-related information could be obtained through an analysis of a digital image that includes an objected presented to an image sensor for the purpose of identifying the human body or conveying the user-related information. Alternatively, the user-related information could be obtained from a source external to the controller 800, in which case the user-related information may initially be received by the communication module 808.

The communication module 808 may be responsible for managing communications between the components of the controller 800, or the communication module 808 may be responsible for managing communications with other computing devices (e.g., a mobile phone associated with the operator, a network-accessible server system accessible to either an entity responsible for manufacturing, providing, or managing pressure-mitigation devices or an entity responsible for prescribing or providing care to the user). The communication module 808 may be wireless communication circuitry that is designed to establish communication channels with other computing devices. Examples of wireless communication circuitry include integrated circuits (also referred to as "chips") configured for Bluetooth, Wi-Fi, NFC, and the like.

Moreover, the communication module 808 may be responsible for providing information for retrieving information from, or uploading information to, the electronic health record that is associated with the human body that is presently being treated. Assume, for example, that the controller 800 receives input indicating that a given person is to be treated using a pressure-mitigation device. In such a situation, the controller 800 may establish a connection with a storage medium that includes the electronic health record of the given person. The connection with the storage medium could be established in response to receiving the input, or the connection with the storage medium could be established in response to the controller 800 being deployed. In some embodiments the controller 800 downloads information from the electronic health record into the memory 804, while in other embodiments the controller 800 simply accesses the information in the electronic health record. This information could be used to determine how to treat the given person. For instance, the controller 800 may determine whether to adjust the programmed pattern for inflating the chambers of the pressure-mitigation device based on this information. As an example, the controller 800 may determine that the rates or pressures at which fluid flows into the chambers should be modified based on the weight and age of the given person. A characteristic of the human body being treated, such as the weight or age, could be specified directly in the information. Alternatively, the controller 800 may infer, compute, or otherwise determine the characteristic based on an analysis of the information. As another example, the controller 800 may determine which pattern to select for inflating the chambers of the pressure-mitigation device, whether to adjust the pattern, etc.

As mentioned above, information could also be transmitted by the communication module 808 to a destination external to the controller 800. For example, the controller 800 could include, or be communicatively connected to, one or more sensors as further discussed below. Data generated by these sensors—or insights gleaned through analysis of the data—could be provided to the communication module 808 for transmission, for example, to a storage medium for uploading into the electronic health record associated with the human body that is being treated.

The controller 800 may be connected to a pressure-mitigation device that includes a series of chambers whose pressure can be individually varied. When the pressure-mitigation device is placed between a human body and the surface of an object, the controller 800 can cause the pressure on an anatomical region of the human body to be varied by controllably inflating and/or deflating chamber(s). Such action can be accomplished by the manifold 810, which controls the flow of fluid to the series of chambers of the pressure-mitigation device. The manifold 810 is further described with respect to FIGS. 9-10.

As further discussed below, transducers mounted in the manifold 810 can generate an electrical signal based on the pressure detected in each chamber of the pressure-mitigation device. Generally, each chamber is associated with a different fluid channel and a different transducer. Accordingly, if the manifold 810 is designed to facilitate the flow of fluid to a pressure-mitigation device with four chambers, the manifold 810 may include four fluid channels and four transducers. In some embodiments, the manifold 810 includes fewer than four fluid channels and/or transducers or more than four fluid channels and/or transducers. Pressure data representative of the values of the electrical signals generated by the transducers can be stored, at least temporarily, in the memory 804. In some embodiments, the pressure data—or insights gleaned through analysis of the pressure data—is transmitted to a destination external to the controller 800 by the communication module 808 for storage or further analysis. Additionally or alternatively, information regarding the flow of fluid into the pressure-mitigation device could be transmitted to the destination. Examples of such information include the elapsed duration of treatment and remaining duration of treatment.

As further discussed below, the manifold 810 may be driven based on a clock signal that is generated by a clock module (not shown). For example, the processor 802 may be configured to generate signals for driving valves in the manifold 810 (or driving chips in communication with the valves) based on a comparison of the clock signal to a programmed pattern that indicates when the chambers of the pressure-mitigation device should be inflated or deflated. The programmed pattern may be one of multiple programmed patterns that are stored in the memory 804.

The clock signal generated by the clock module could also be used in other ways.

As an example, the controller 800 may be configured to generate notifications, for example, that indicate when the human body is to be turned, when medication is due to be administered, etc. Notifications may be generated by an indicating component on a periodic basis based on the clock signal. The term "indicating component" may refer to any component that is able to generate audible, visual, or tactile notifications. Examples of indicating components include the display 806 that is able to produce visual notifications, the audio output mechanism 822 that is able to produce audible notifications, and a haptic element (not shown) that is able to produce tactile notifications. Some embodiments of the controller 800 include more than one indicating component. For example, notifications may be generated by a first indicating component (e.g., the display 806) while notifications are generated by a second indicating component (e.g., the audio output mechanism 822).

An analysis platform may be responsible for examining the pressure data. For convenience, the analysis platform is described as a computer program that resides in the memory 804. However, the analysis platform could be comprised of software, firmware, or hardware that is implemented in, or accessible to, the controller 800. In accordance with embodiments described herein, the analysis platform may include a processing module 816, analysis module 818, and graphical user interface (GUI) module 820. Each of these modules can be an integral part of the analysis platform. Alternatively, these modules can be logically separate from the analysis platform but operate "alongside" it. Together, these modules enable the analysis platform to gain insights not only into whether the pressure-mitigation device connected to the controller 800 is being used properly, but also into the health of the human body situated on the pressure-mitigation device.

The processing module 816 can process pressure data obtained by the analysis platform into a format that is suitable for the other modules. For example, in preparation for analysis by the analysis module 818, the processing module 816 may apply algorithms designed for temporal aligning, artifact removal, and the like. Accordingly, the processing module 816 may be responsible for ensuring that the pressure data is accessible to the other modules of the analysis platform. As further discussed below, the processor 802 may forward at least some of the pressure data, in either its processed or unprocessed form, to the communication module 808 for transmittal to a destination for analysis. In such a scenario, the processing module 816 may apply operations (e.g., filtering, compressing, labelling) to the pressure data before it is forwarded to the communication module 808 for transmission to the destination.

By examining the pressure data in conjunction with flow data representative of the fluid flowing from the controller 800 into the pressure-mitigation device, the analysis module 818 can control how the chambers are inflated and/or deflated. For example, the analysis module 818 may be responsible for separately controlling the set point for fluid flowing into each chamber such that the pressures of the chambers match a predetermined pattern.

By examining the pressure data, the analysis module 818 may also be able to sense movements of the human body under which the pressure-mitigation device is positioned. These movements may be caused by the user, another individual (e.g., a caregiver or an operator of the controller 800), or the underlying surface. The analysis module 818 may apply algorithms to the data representative of these movements (also referred to as "movement data" or "motion data") to identify repetitive movements and/or random movements to better understand the health state of the user. For example, the analysis module 818 may be able to produce a coverage metric indicative of the amount of time that the human body is properly positioned on the pressure-mitigation device. As further discussed below, the controller 800 (or another computing device) may be able to establish whether the pressure-mitigation device has been properly deployed and/or operated based on the coverage metric. As another example, the analysis module 818 may be able to establish the respiration rate, heart rate, or another vital measurement based on the movements of the user. Generally, the movement data is derived from the pressure data. That is, the analysis module 818 may be able to infer movements of the human body by analyzing the pressure of the chambers of the pressure-mitigation device in conjunction with the rate at which fluid is being delivered to those chambers. Consequently, some embodiments of the pressure-mitigation device may not actually include any sensors for measuring movement, such as accelerometers, tilt sensors, or gyroscopes.

The analysis module 818 may respond in several ways after examining the pressure data. For example, the analysis module 818 may generate a notification (e.g., an alert) to be presented by the controller 800 or transmitted to another computing device by the communication module 808. The other computing device may be associated with a healthcare professional, a caregiver, or some other entity (e.g., a researcher or an insurer). As another example, the analysis module 818 may cause the pressure data (or analyses of the pressure data) to be integrated with the electronic health record of the user. Generally, the electronic health record is maintained in a storage medium that is accessible to the communication module 808 across a network.

The GUI module 820 may be responsible for generating interfaces that can be presented on the display 806. Various types of information can be presented on these interfaces. For example, information that is calculated, derived, or otherwise obtained by the analysis module 818 may be presented on an interface for display to the user or operator. As another example, visual feedback may be presented on an interface so as to indicate whether the user is properly situated on the pressure-mitigation device.

The controller 800 may include a power component 812 that is able to provide to the other components residing within the housing, as necessary. Examples of power components include rechargeable lithium-ion (Li-Ion) batteries, rechargeable nickel-metal hydride (NiMH) batteries, rechargeable nickel-cadmium (NiCad) batteries, etc. In some embodiments, the controller 800 does not include a power component, and thus must receive power from an external source. In such embodiments, a cable designed to facilitate the transmission of power (e.g., via a physical connection of electrical contacts) may be connected between the power interface 814 of the controller 800 and the external source. The external source may be, for example, an alternating current (AC) power socket or another computing device. The cable connected to the power interface 814 of the controller 800 may also be able to convey power so as to recharge the power component 812.

Embodiments of the controller 800 can include any subset of the components shown in FIG. 8, as well as additional components not illustrated here.

For example, while the controller 800 is able to receive and transmit data wirelessly via the communication module 808, other embodiments of the controller 800 may include a physical data interface through which data can be transmitted to another computing device. Examples of physical data interfaces include Ethernet ports, Universal Serial Bus (USB) ports, and proprietary ports.

As another example, some embodiments of the controller 800 include an audio output mechanism 822 and/or an audio input mechanism 824. The audio output mechanism 822 may be any apparatus that is able to convert electrical impulses into sound. One example of an audio output mechanism is a loudspeaker (or simply "speaker"). Meanwhile, the audio input mechanism 824 may be any apparatus that is able to convert sound into electrical impulses. One example of an audio input mechanism is a microphone. Together, the audio output and input mechanisms 822, 824 may enable the user or operator to engage in an audible exchange with a person who is not located proximate the controller 800. Assume, for example, that the user has become misaligned with the pressure-mitigation device. In such a scenario, the user may utilize the audio input mechanism 824 to verbally ask for assistance, for example, from another person who is able to verbally confirm that assistance is forthcoming using the audio output mechanism 822. The other person could be a healthcare professional or caretaker of the user. This may be useful in situations where the user is unable to reposition herself on the pressure-mitigation device due to an underlying condition that inhibits or prevents movement.

The audio input mechanism 824 may be able to convert sound in the ambient environment into electrical impulses that can be examined by the processor 802, transmitted by the communication module 808, etc. The audio input mechanism 824 may also be able to generate a signal that is indicative of more nuanced sounds. For example, the audio input mechanism 824 may generate data that is representative of sounds originating from within the human body situated on a pressure-mitigation device. These sounds may be representative of auscultation sounds generated by the circulatory, respiratory, and gastrointestinal systems. This data could be transmitted (e.g., by the communication module 808) to a destination for analysis.

Accordingly, embodiments of the controller 800 may include an audio input mechanism 824 in addition to, or instead of, an audio output mechanism 822. In embodiments where the controller 800 includes an audio output mechanism 822, the processor 802 may transmit a signal to the audio output mechanism 822, so as to cause sound (e.g., in the form of an utterance) to be emitted therefrom. This may be done before treatment has begun (e.g., to ensure the pressure-mitigation apparatus is properly deployed), while treatment is ongoing (e.g., to engage the user), or after treatment is complete (e.g., as a means of incentivizing future treatment). While the utterances emitted from the audio output mechanism 822 may commonly be instructions regarding use of the pressure-mitigation device and controller 800, the utterances could alternatively be questions, for example, to seek feedback from the user.

In some embodiments, the utterances emitted from the audio output mechanism 822 are recorded, and the corresponding signal is stored in the memory 804 or retrieved by the communication module 808 from a source external to the controller 800. In other embodiments, the utterances are part of a conversation. By initiating communication with a computing device, the communication module 808 can facilitate the exchange of signals between the controller 800 and computing device. For example, the communication module 808 may receive, from the computer program, a first signal that is representative of an utterance as recorded by an audio input mechanism of the computing device. In such a scenario, the processor 802 can generate a second signal based on the first signal and then transmit the second signal to the audio output mechanism 822, so as to cause the utterance to be emitted therefrom. Similarly, if the audio input mechanism 824 generates a signal that is representative of an utterance spoken by the user of the pressure-mitigation device or the operator of the controller 800, the processor 802 may transmit the signal (or another signal that is based on the signal) to the communication module 808 for transmission to the computing device. As mentioned above, this exchange of signals may occur in near real time, so as to permit conversation in which the utterances recorded by the audio input mechanism 824 are responsive to the utterances emitted by the audio output mechanism 822, or vice versa.

Other sensors may also be implemented in, or accessible to, the controller 800. For example, sensors may be contained in the housing of the controller 800 and/or embedded within the pressure-mitigation device that is connected to the controller 800. Collectively, these sensors may be referred to as the "sensor suite" 826 of the pressure-mitigation system. At a high level, these sensors generally output a signal that is indicative of either a monitored characteristic of the ambient environment or a monitored characteristic of the human body being treated.

Sensors that monitor a characteristic of the ambient environment may be useful in determining how to operate the controller 800. For example, the sensor suite 826 may include a motion sensor whose output is indicative of motion of the controller 800 or pressure-mitigation device. Examples of motion sensors include multi-axis accelerometers and gyroscopes. As another example, the sensor suite 826 may include a proximity sensor whose output is indicative of proximity of an object located in a field of view. Based on the output, the controller 800 may be able to infer location of the object with respect to the pressure-mitigation device or the controller 800 itself. A proximity sensor may include, for example, (i) an emitter that is able to emit infrared (IR) light away from the controller 800 within the field of view and (ii) a detector that is able to detect IR light reflected by the object toward the proximity sensor (and therefore, the controller 800). These types of proximity sensors are sometimes called laser imaging, detection, and ranging (LiDAR) scanners. Other examples of sensors include an ambient light sensor whose output is indicative of the amount of light in the ambient environment, a temperature sensor whose output is indicative of the temperature of the ambient environment, and a humidity sensor whose output is indicative of the humidity of the ambient environment. The outputs produced by the sensor suite 826 may provide greater insight into the environment in which the controller 800 is deployed (and therefore, the environment in which the human body situated on the pressure-mitigation device is to be treated).

Similarly, sensors that monitor a characteristic of the human body being treated may be useful in determining how to operate the controller 800. Generally, sensors that monitor characteristics of human bodies are more specialized and are designed to generate, obtain, or otherwise produce information related to the health of the human body. For example, the sensor suite 826 may include a vascular scanner. The term "vascular scanner" may be used to refer to an imaging instrument that includes (i) an emitter operable to emit electromagnetic radiation (e.g., in the near infrared range) into an anatomical region situated proximate thereto and (ii) a detector operable to sense electromagnetic radiation reflected by physiological structures inside the anatomical region. Normally, a digital image is created based on the reflected electromagnetic radiation. The processor 802 could compare the digital image against a reference template for the vasculature in the anatomical region and then determine whether to authorize use of the controller based on an outcome of the comparison. Alternatively, the digital image could serve as a reference template for the vasculature in the anatomical region at a corresponding point in time. The vasculature in the anatomical region could be periodically or continually monitored based on outputs produced by a vascular scanner over time. Additionally or alternatively, the sensor suite 826 may include sensors that are able to determine the oxygen level of the blood, measure blood pressure, compute heartrate, etc. In some embodiments, the controller 800 may include a pulse oximeter that is able to infer oxygen saturation in an anatomical region situated proximate thereto from an analysis of peripheral oxygen saturation readings.

In some embodiments, the processor 802 may adjust the programmed pattern that specifies how to inflate the chambers of the pressure-mitigation device based on the outputs, if any, produced by the sensor suite 826. Assume, for example, that the controller 800 includes a sensor able to monitor temperature and/or a sensor able to monitor ambient light. The processor 802 may determine, based on an analysis of the signals output by these sensors, whether to adjust the programmed pattern (e.g., based on a determination that it is daytime versus nighttime). As another example, the controller 800 may determine whether to adjust the programmed pattern based on the output produced by a sensor able to measure the heart rate or blood pressure of the user.

Based on the outputs produced by the sensor suite 826, the controller 800 (or some other computing device) may be able to compute some or all of the main vital signs, namely, body temperature, blood pressure, pulse rate, and breathing rate (also referred to as "respiratory rate"). For example, a given sensor may produce, as output, a signal that is representative of values, in temporal order, that are indicative of a monitored characteristic of the ambient environment or human body to be treated, and the processor 802 may compute, in an ongoing manner, values for a given vital sign based on the signal. The values could be stored in the memory 804, provided to the communication module 808 for transmission to a destination (e.g., a storage medium for storage in the electronic health record), or presented on the display 806.

Moreover, the controller 800 (or some other computing device) may be able to compute metrics that are indicative of the health of the human body, despite not being one of the main vital signs. For example, the outputs generated by the sensor suite 826 could be used to establish whether the human body is performing a given activity (e.g., sleeping or eating). The outputs could be used to not only ascertain the sleep pattern of the human body, but also whether changes in the sleep pattern indicate whether the health state of the human body has improved (e.g., sleep more consistent with longer duration following deployment of the pressure-mitigation device).

Similarly, the controller 800 (or some other computing device) may be able to detect occurrences of medical events by examining the outputs produced by the sensor suite 826, the pressure data generated by the transducers mounted in the manifold 810, the movement data derived from the pressure data, or any combination thereof. For example, the processor 802 may parse any of these data to identify individual values (e.g., those exceeding an upper threshold or falling below a lower threshold) or patterns of values that are indicative of a medical event. Examples of medical events include seizures and myocardial infarctions (also called "heart attacks"), as well as less serious events such as intermittent pauses in breathing (e.g., due to sleep apnea), shortness of breath, heart palpitations, and excessing sweating. Upon discovering an occurrence of a medical event, the processor 802 may cause a notification to be presented by the controller 800 and/or transmit an indication of the medical event to a destination (e.g., a storage medium for storage in the electronic health record).

As mentioned above, sensors could be included in the pressure-mitigation device in addition to, or instead of, the controller 800. Accordingly, a pressure-mitigation device may include a plurality of chambers that are formed by interconnections between a first layer and a second layer, a sensor embedded between the first and second layers, and a processor that is responsible for handling data generated by the sensor. The sensor could be configured to output values indicative of a monitored characteristic of the ambient environment or human body being treated. Meanwhile, the processor may forward these values—in their raw form or a processed form—to an interface for transmission to the controller 800. The interface may be part of a communication module that is communicatively connected to the communication module 808 of the controller 800, or the interface may be part of a data cable interconnected between the pressure-mitigation device and controller 800. The data cable may be part of the multi-channel tubing for conveying fluid that extends between the pressure-mitigation device and controller 800.

Note that the sensors included in the sensor suite 826 need not necessarily be included in the controller 800 or pressure-mitigation device. For example, the controller 800 may be communicatively connected to ancillary sensors that are included in nearby items (e.g., blankets and clothing), attached directly to the human body, etc.

These various components may allow the controller 800 to be readily integrated into a network-connected environment, such as a home or hospital. Thus, the controller 800 may be communicatively coupled to mobile phones, tablet computers, wearable electronic devices (e.g., fitness trackers and watches), or network-connected devices (also referred to as "smart devices"), such as televisions and home assistant devices. Similarly, the controller 800 may be communicatively coupled to medical devices, such as cardiac pacemakers, insulin pumps, glucose monitoring devices, and the like. Accordingly, the controller 800 may receive, at the communication module 808 from a medical device, data related to the health of the user of the pressure-mitigation device. Specifically, the controller 800 may receive a signal that is indicative of measurements of a monitored characteristic of the user. This level of integration can provide several notable benefits over conventional technologies for mitigating pressure.

As an example, the pressure-mitigation system of which the controller 800 is a part may be used to monitor health of a human body in a more holistic sense. As mentioned above, insights into movements of the human body can be surfaced through analysis of pressure data generated by the controller 800 or pressure-mitigation device. Analysis of these movements over an extended period of time (e.g., days, weeks, or months) may lead to the discovery of abnormalities that might otherwise go unnoticed. For example, the controller 800 (or some other computing device) may infer that the human body is suffering from an ailment in response to a determination that its movements over a recent interval of time differ from those that would be expected based on past intervals of time. At a high level, insights gained through analysis of the pressure data can be used not only to define a "health baseline" for the human body, but also to discover when deviations from the health baseline occur.

As another example, the controller 800 may be responsible for providing or supplementing prompts to administer medication in accordance with a regimen. Assume, for example, that a user positioned on a pressure-mitigation device is associated with a regimen that requires a medication be administered regularly in accordance with a dosing schedule. The controller 800 may promote adherence to the regimen by prompting the user or another person (e.g., an operator of the controller 800) to administer the medication. Specifically, the processor 802 may determine whether a dose of medication is due to be administered, for example, by comparing a clock signal generated by a clock module against the dosing schedule. The processor 802 can cause a notification to be generated by an indicating component in response to a determination that a dose of medication is due to be administered. For example, visual notifications could be presented by the display 806, or audible notifications could be presented by the audio output mechanism 822. Additionally or alternatively, the controller 800 could cause digital notifications (also referred to as "electronic notifications") to be presented by a computing device that is communicatively coupled to the controller 800. In some embodiments, the dosing schedule is stored in the memory 804 of the controller 800. In other embodiments, the dosing schedule is stored in the memory of a computing device that is communicatively coupled to the controller 800. For example, the dosing schedule may be maintained by a computer program that is executing on a mobile device associated with the user, and when the computer program determines that a dose of the medication is due to be administered, the computer program may transmit an instruction to the controller 800 to generate a notification. As another example, the communication module 808 may obtain the dosing schedule from the computer program, and the dosing schedule can be stored in the memory 804. Rather than obtain the dosing schedule from a mobile device associated with the user, the controller 800 may alternatively obtain the dosing schedule from another computing device (e.g., a storage medium managed by, or associated with, a healthcare provider responsible for prescribing the medication).

As another example, the controller 800 may be able to facilitate communication with healthcare professionals. Assume, for example, that the controller 800 is deployed in a home environment that healthcare professionals visit infrequently or not at all. In such a scenario, the controller 800 may allow the user to communicate with healthcare professionals who are located outside of the home environment. Thus, the user may be able to communicate, via the audio output and input mechanisms 822, 824, with healthcare professionals who are located in a hospital environment (e.g., at which the user received treatment) or their own home environments.

As another example, the controller 800 may be able to facilitate communication with emergency services. For instance, if the controller 800 determines (e.g., through analysis of pressure data) that a serious medical event has occurred or no movement has occurred for a predetermined amount of time, the controller 800 may prompt the user to respond and, based on the response or lack thereof, determine whether to notify emergency services. Similarly, if the controller 800 receives input from the user indicative of a request for assistance, the controller 800 may initiate communication with emergency services. Thus, the controller 800 may be programmed to perform some action if, for example, it determines (e.g., through analysis of the signal generated by the audio input mechanism 824) that the user has indicated she has fallen or has experienced a medical event.

These benefits allow pressure-mitigation systems to be deployed in situations where frequent visits by healthcare professionals may not be practical or possible. For example, when deployed in a hospital environment, a pressure-mitigation system may allow healthcare professionals to visit patients less frequently. Patients situated on pressure-mitigation devices may not need to be turned to alleviate pressure as often, and healthcare professionals may not need to continually check on patients if pressure-mitigation systems are able to autonomously discover changes in health. As another example, when deployed in a home environment, a pressure-mitigation system may be able to counter a lack of visits from healthcare professionals. If a patient is instructed to situate herself on a pressure-mitigation device while at home, the patient may only need to be visited every few days (e.g., every 3, 5, or 7 days) rather than once per day or multiple times per day. Overall, implementing pressure-mitigation systems can lead to significant cost savings because healthcare professionals are required to make less frequent visits to offsite locations and perform fewer medical procedures at onsite locations, and because patients can be discharged more quickly.

The controller 800 may also be designed to focus on wellness in addition to, or instead of, treatment for (and prevention of) pressure-induced injuries. As an example, embodiments of the controller 800 may be designed to aid in sleep management, for healthy individuals and/or unhealthy individuals. Using the audio output mechanism 822 in combination with the manifold 810, the controller 800 may be able to accomplish tasks such as simulating the presence of another person, for example, by producing vocal sounds, breathing sounds, applying pressure, and the like. Calming sounds—like those made by rain, waves, and birds—could also be emitted through the audio output mechanism 822 in an effort to soothe the user of the pressure-mitigation device.

Figure 9:
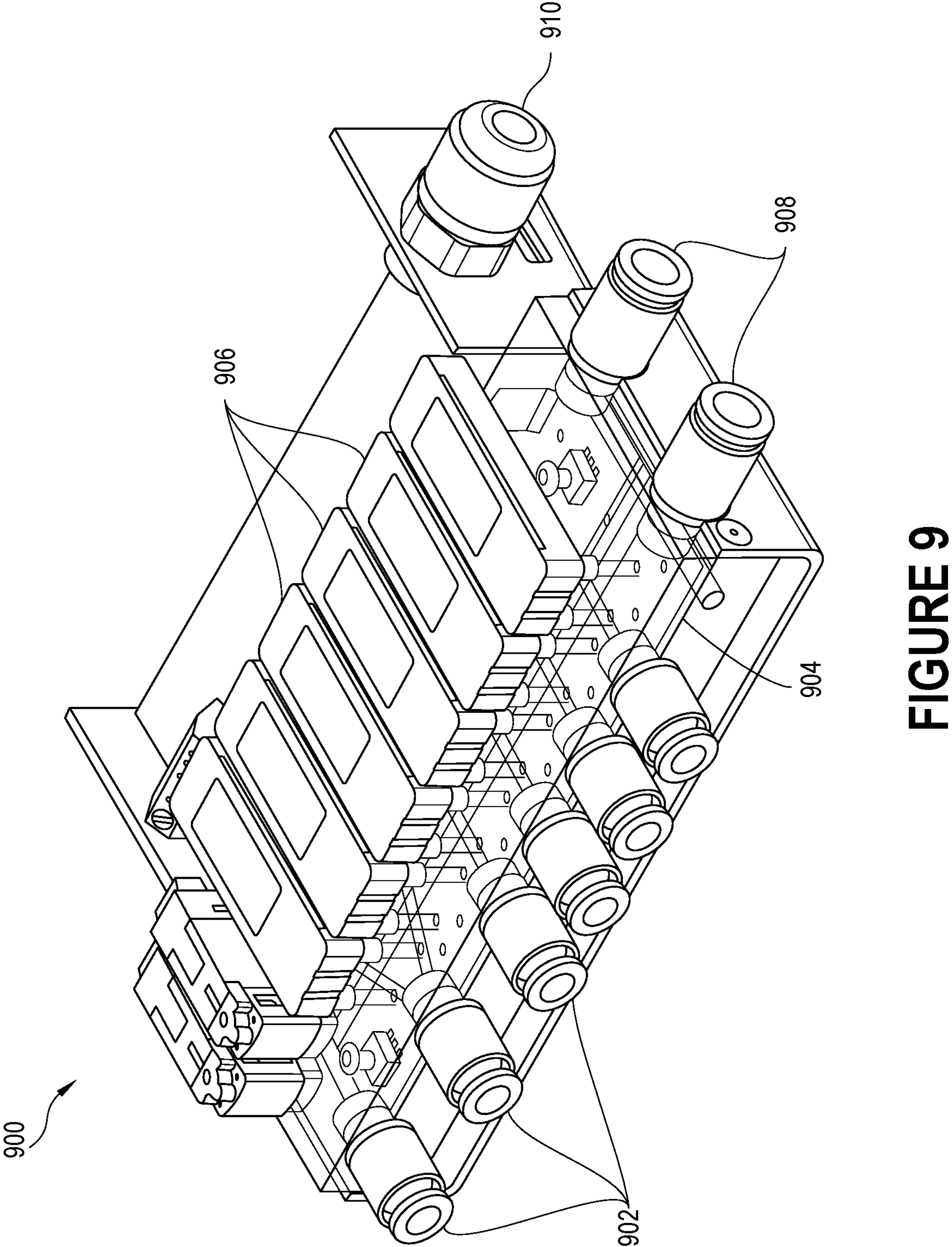
FIG. 9 is an isometric view of a manifold for controlling the flow of fluid (e.g., air) to the chambers of a pressure-mitigation device in accordance with embodiments of the present technology.

FIG. 9 is an isometric view of a manifold 900 for controlling the flow of fluid (e.g., air) to the chambers of a pressure-mitigation device in accordance with embodiments of the present technology. As discussed above, a controller can be configured to inflate and/or deflate the chambers of a pressure-mitigation device to create a pressure gradient that moves the main point of pressure applied by an object across the surface of a human body situated on the pressure-mitigation device. To accomplish this, the manifold 900 can guide fluid to the chambers through a series of valves 902. In some embodiments, each valve 902 corresponds to a separate chamber of the pressure-mitigation device. In some embodiments, at least one valve 902 corresponds to multiple chambers of the pressure-mitigation device. In some embodiments, at least one valve 902 is not used during operation. For example, if the pressure-mitigation device includes four chambers, multi-channel tubing may be connected between the pressure-mitigation device and four valves 902 of the manifold 900. In such embodiments, the other valves may remain sealed during operation.

Generally, the valves 902 are piezoelectric valves designed to switch from one state (e.g., an open state) to another state (e.g., a closed state) in response to an application of voltage. Each piezoelectric valve includes at least one piezoelectric element that acts as an electromechanical transducer. When a voltage is applied to the piezoelectric element, the piezoelectric element is deformed, thereby resulting in mechanical motion (e.g., the opening or closing of a valve). Examples of piezoelectric elements include disc transducers, bender actuators, and piezoelectric stacks.

Piezoelectric valves provide several benefits over other valves, such as linear valves and solenoid-based valves. First, piezoelectric valves do not require holding current to maintain a state. As such, piezoelectric valves generate almost no heat. Second, piezoelectric valves create almost no noise when switching between states, which can be particularly useful in medical settings. Third, piezoelectric valves can be opened and closed in a controlled manner that allows the manifold 900 to precisely approach a desired flow rate without overshoot or undershoot. In contrast, the other valves described above must be in either an open state, in which the valve is completely open, or a closed state, in which the valve is completely closed. Fourth, piezoelectric valves require very little power to operate, so a power component (e.g., power component 812 of FIG. 8) may only need to provide 3-6 watts to the manifold 900 at any given time. While embodiments of the manifold 900 may be described in the context of piezoelectric valves, other types of valves, such as linear valves or solenoid-based valves, could be used instead of, or in addition to, piezoelectric valves.

In some embodiments, the manifold 900 includes one or more transducers 906 and a circuit board 904 that includes one or more chips for managing communication with the valves 902 and the transducer(s) 906. Because these local chip(s) reside within the manifold 900 itself, the valves 902 can be digitally controlled in a precise manner. The local chip(s) may be connected to other components of the controller. For example, the local chip(s) may be connected to other components housed within the controller, such as processors (e.g., processor 802 of FIG. 8) and clock modules. The transducer(s) 906, meanwhile, can generate an electrical signal based on the pressure of each chamber of the pressure-mitigation device. Generally, each chamber is associated with a different valve 902 and a different transducer 906. Here, for example, the manifold includes six valves i02 capable of interfacing with the pressure-mitigation device, and each of these valves may be associated with a corresponding transducer 906. Pressure data representative of the values of the electrical signals generated by the transducer(s) 906 can be provided to other components of the controller for further analysis.

The manifold 900 may also include one or more compressors. In some embodiments each valve 902 of the manifold 900 is fluidically coupled to the same compressor, while in other embodiments each valve 902 of the manifold 900 is fluidically coupled to a different compressor. Each compressor can increase the pressure of fluid by reducing its volume before guiding the fluid to the pressure-mitigation device.

Fluid produced by a pump may initially be received by the manifold 900 through one or more ingress fluid interfaces 908 (or simply "ingress interfaces"). As noted above, in some embodiments, a compressor may then increase pressure of the fluid by reducing its volume. Thereafter, the manifold 900 can controllably guide the fluid into the chambers of a pressure-mitigation device through the valves 902. The flow of fluid into each chamber can be controlled by local chip(s) disposed on the circuit board 904. For example, the local chip(s) can dynamically vary the flow of fluid into each chamber in real time by controllably applying voltages to open/close the valves 902.

In some embodiments, the manifold includes one or more egress fluid interfaces 910 (or simply "egress interfaces"). The egress fluid interface(s) 910 may be designed for high pressure and high flow to permit rapid deflation of the pressure-mitigation device. For example, upon determining that an operator has provided input indicative of a request to deflate the pressure-mitigation device (or a portion thereof), the manifold 900 may allow fluid to travel back though the valve(s) 902 from the pressure-mitigation device and then out through the egress fluid interface(s) 910. Thus, the egress fluid interface(s) 910 may also be referred to as "exhausts" or "outlets." To provide the input, the operator may interact with a mechanical input component (e.g., mechanical input component 706 of FIG. 7A) or a digital input component (e.g., visible on display 710 of FIG. 7A).

Figure 10:
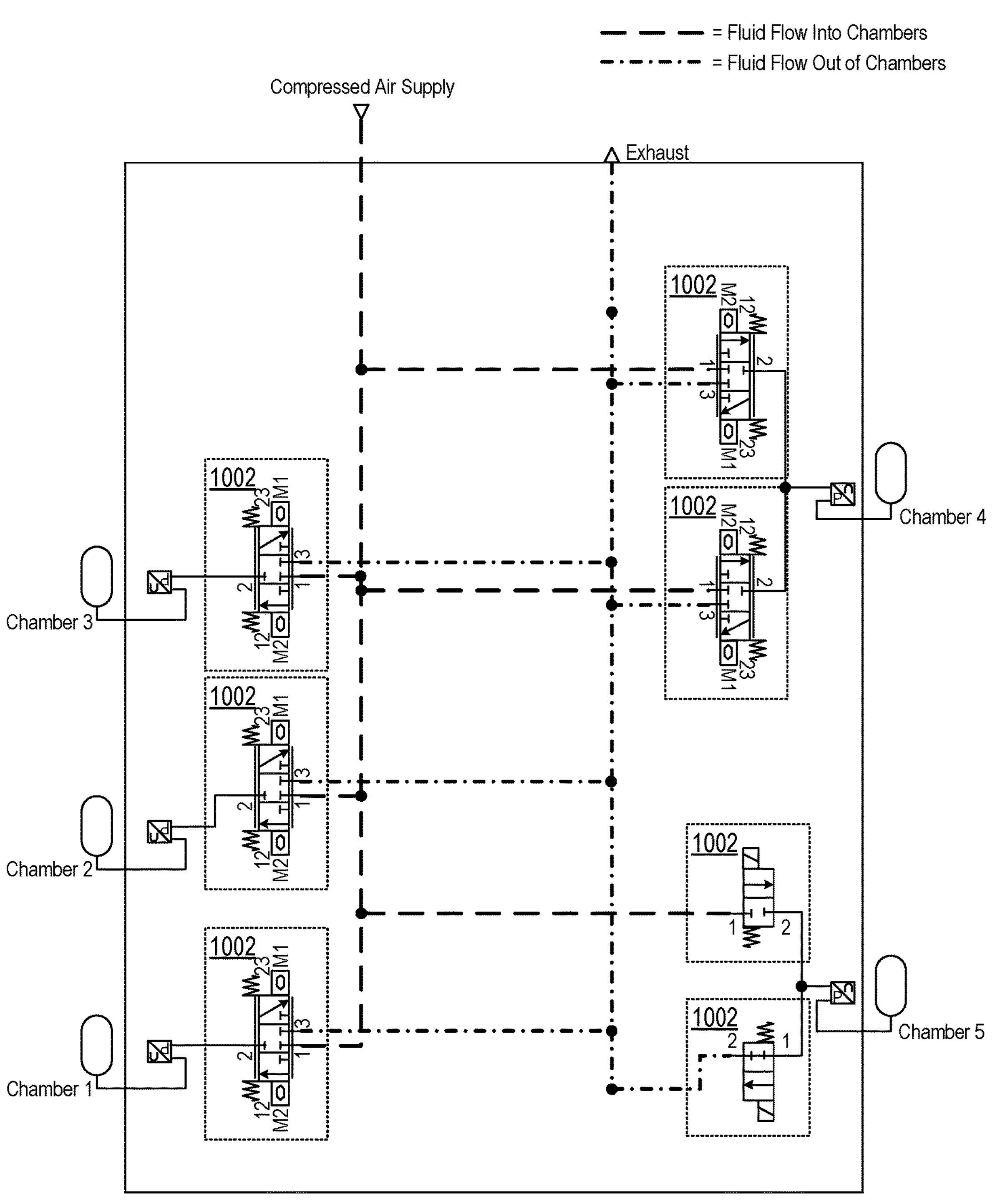
FIG. 10 is a generalized electrical diagram illustrating how the piezoelectric valves of a manifold can separately control the flow of fluid along multiple channels in accordance with embodiments of the present technology.

FIG. 10 is a generalized electrical diagram illustrating how the piezoelectric valves 1002 of a manifold can separately control the flow of fluid along multiple channels in accordance with embodiments of the present technology. In FIG. 10, the manifold includes seven piezoelectric valves 1002. Other embodiments of the manifold may include fewer than seven valves or more than seven valves. Fluid, such as air, can be guided by the manifold through the piezoelectric valves 1002 to the chambers of a pressure-mitigation device. In FIG. 10, the manifold is fluidically connected to a pressure-mitigation device that has five chambers. However, in other embodiments, the manifold may be fluidically connected to a pressure-mitigation device that has fewer than five chambers or more than five chambers.

All of the piezoelectric valves 1002 included in the manifold need not necessarily be identical to one another. Piezoelectric valves may be designed for high pressure and low flow, high pressure and high flow, low pressure and low flow, or low pressure and high flow. In some embodiments all of the piezoelectric valves included in the manifold are the same type, while in other embodiments the manifold includes multiple types of piezoelectric valves. For example, piezoelectric valves corresponding to side supports of the pressure-mitigation device may be designed for high pressure and high flow (e.g., to allow for a quick discharge of fluid stored therein), while piezoelectric valves corresponding to chambers of the pressure-mitigation device may be designed for high pressure and low flow. Moreover, some piezoelectric valves may support bidirectional fluid flow, while other piezoelectric valves may support unidirectional fluid flow. Generally, if the manifold includes unidirectional piezoelectric valves, each chamber in the pressure-mitigation device is associated with a pair of unidirectional piezoelectric valves to allow fluid flow in either direction. Here, for example, Chambers 1-3 are associated with a single bidirectional piezoelectric valve, Chamber 4 is associated with two bidirectional piezoelectric valves, and Chamber 5 is associated with two unidirectional piezoelectric valves.

The chambers of a pressure-mitigation device may be inflated/deflated for a predetermined duration of 15-180 seconds (e.g., 30 seconds, 60 seconds, 90 seconds, 120 seconds, 150 seconds, or any duration therebetween) in accordance with a predetermined pattern. Thus, the status of each chamber may be varied at least every 60 seconds, 90 seconds, 120 seconds, 240 seconds, etc. Generally, the predetermined pattern causes the chambers to be inflated/deflated in a non-identical manner. For example, if the pressure-mitigation device includes four chambers, the first and second chambers may be inflated for 30 seconds, the second and third chambers may be inflated for 45 seconds, the third and fourth chambers may be inflated for 30 seconds, and then the first and fourth chambers may be inflated for 45 seconds. These chambers may be inflated/deflated to a predetermined pressure level from 0-100 millimeters of mercury (mmHg) (e.g., 15 mmHg, 20 mmHg, 30 mmHg, 45 mmHg, 50 mmHg, or any pressure level therebetween). In some embodiments, the inflation pattern administered by the controller inflates/deflates two or more chambers at one time. In these embodiments, the chambers can be inflated/deflated to the same or different pressure levels, and the duration that the chambers are maintained at the pressure levels may be the same or different. For example, in the scenario above where the first and second chambers are inflated, the first chamber may be inflated to a pressure of 15 mm Hg while the second chamber may be inflated to a pressure of 30 mm Hg. In other embodiments, the controller can apply different inflation/deflation patterns to the individual chambers.

Figure 11:
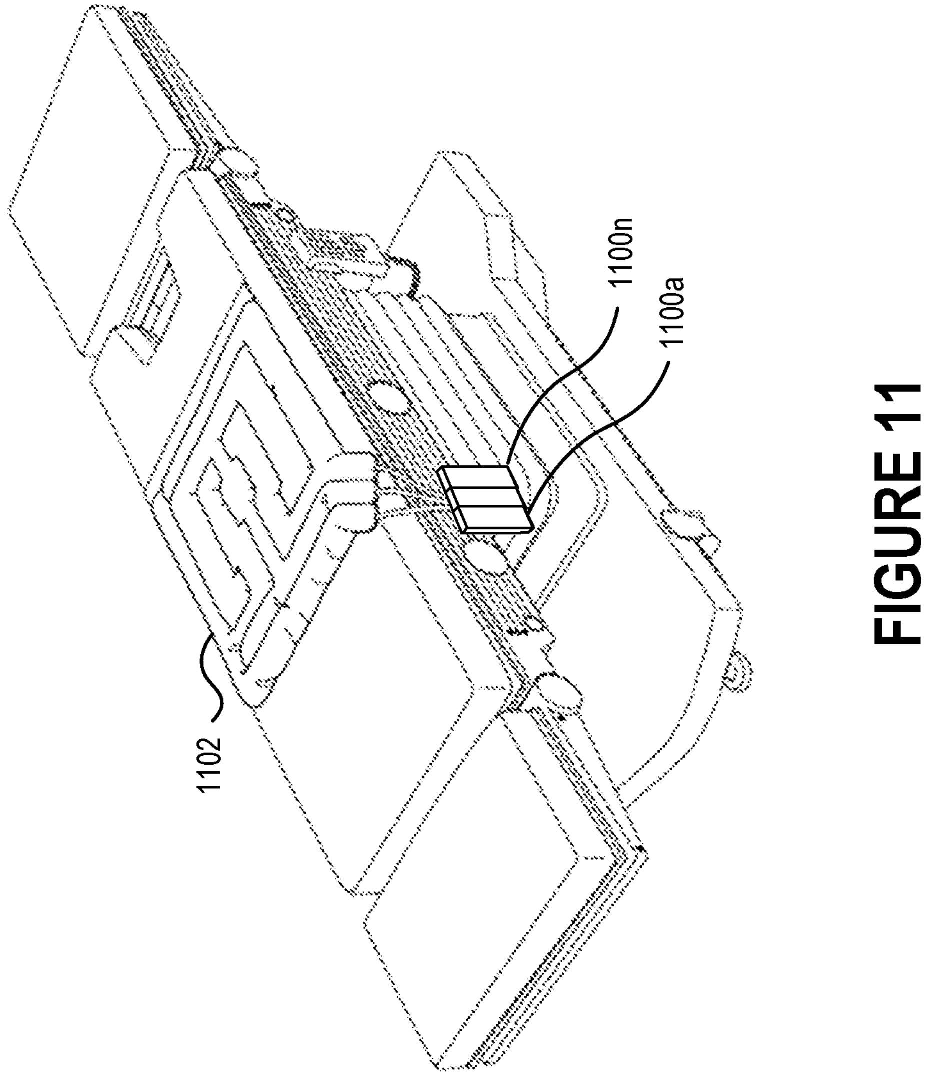
FIG. 11 illustrates how aspects of the controller and pump may be incorporated into modular assemblies.

FIG. 11 illustrates how aspects of the controller and pump may be incorporated into modular assemblies 1100*a*-*n*. In such embodiments, the pump that supplies the flow of fluid that is manipulated to inflate the chambers of a pressure-mitigation device 1102 can be part of the controller. As shown in FIG. 11, these modular assemblies 1100*a*-*n* can be detachably connected to the pressure-mitigation device 1102 as necessary, and then removed when the pressure-mitigation device 1102 is no longer being used.

In some embodiments, the number of modular assemblies needed to controllably inflate a given pressure-mitigation device is based on the number of channels into which fluid can flow. In FIG. 11, for example, the pressure-mitigation device 1102 includes three channels for the three chambers, as the pressure-mitigation device 1102 does not include side supports. Each modular assembly can be designed to support a predetermined number of channels. For example, modular assemblies may be designed to support a single channel, or modular assemblies may be designed to support more than one channel (e.g., two or three channels).

In other embodiments, the number of modular assemblies needed to controllably inflate a given pressure-mitigation device is based on a characteristic of a human body to be situated thereon and/or a characteristic of the surface on which the given pressure-mitigation device is to be deployed. For example, each modular assembly may be "weight rated" for a certain number of pounds, and the number of modular assemblies that are needed may depend on the weight of the human body.

Note that, in some embodiments, these modular assemblies 1100*a-n* can be attached directly to the pressure-mitigation device 1102 without any intervening tubing. In such embodiments, each modular assembly may have one or more attachment mechanisms located around its egress fluid interface, and the pressure-mitigation device 1102 may have one or more attachment mechanisms located around each of its ingress fluid interfaces. Normally, these ingress fluid interfaces are located in easily reachable places. For example, the ingress fluid interfaces may be located around the periphery of the pressure-mitigation device as shown in FIGS. 1A-4A and 11. Thus, the ingress fluid interfaces may be located in "flaps" or "extensions" that extend off the underlying surface on which the human body and pressure-mitigation device are situated. These "flaps" or "extensions" may extend the chambers outside of the geometrical pattern to be oriented beneath the human body.

As an example, assume that the pressure-mitigation device 1102 has multiple ingress fluid interfaces through which fluid is able to flow into corresponding chambers. Each ingress fluid interface may have magnets arranged about its periphery. Each modular assembly may have a complementary arrangement of magnets about the periphery of its egress fluid interface. When a modular assembly is brought within proximity of a given ingress fluid interface of the pressure-mitigation device 1102, the complementary arrangements of magnets can attract one another. Thus, the egress fluid interface of the modular assembly and the ingress fluid interface of the pressure-mitigation device 1102 can be detachably connected to one another without intervening tubing. Other examples of attachment mechanisms include clips, clasps, buttons, latches, patches of hook-and-loop fasteners, adhesives, and the like. Note that while this feature is described in the context of modular assemblies, a non-modular controller (e.g., the controller 700 of FIGS. 7A-C) could also be attached directly to a pressure-mitigation device without any intervening tubing.

Methodologies for Relieving Pressure on a Human Body

Figure 12:
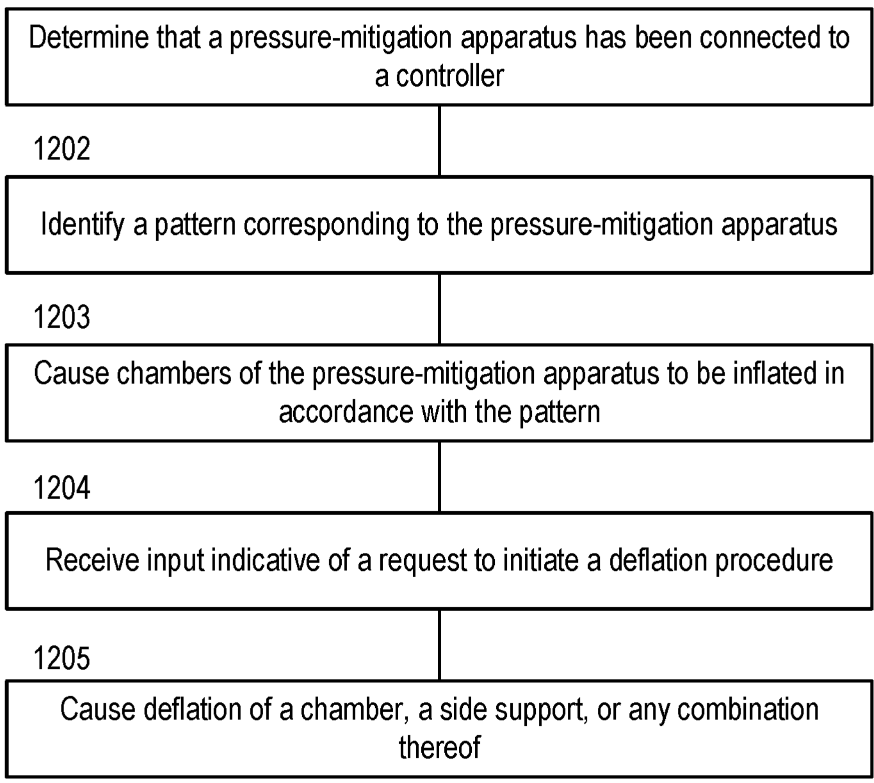
FIG. 12 is a flow diagram of a process for varying the pressure in the chambers of a pressure-mitigation device that is positioned between a human body and a surface in accordance with embodiments of the present technology.

FIG. 12 is a flow diagram of a process 1200 for varying the pressure in the chambers of a pressure-mitigation device that is positioned between a human body and a surface in accordance with embodiments of the present technology. By varying the pressure in the chambers, a controller can move the main point of pressure applied by the surface across the human body. For example, the main point of pressure applied by the support surface to the human body may be moved amongst multiple predetermined locations by sequentially varying the pressure in different predetermined subsets of chambers. Note that the human body could be in nearly any position, with minimal changes to the process 1200. Thus, the pressure-mitigation device may be arranged so that pressure is relieved an anatomical region located along the anterior or posterior side of the human body.

Initially, a controller can determine that a pressure-mitigation device has been connected to the controller (step 1201). The controller may detect which type of pressure-mitigation device has been connected by monitoring the connection between a fluid interface (e.g., the fluid interface 708 of FIG. 7B) and the pressure-mitigation device. Each type of pressure-mitigation device may include a different type of connector. For example, a pressure-mitigation device designed for deployment on elongated objects (e.g., pressure-mitigation apparatus 100 of FIGS. 1A-B) may include a first arrangement of magnets in its connector, and a pressure-mitigation apparatus designed for deployment on non-elongated objects (e.g., the pressure-mitigation apparatus of FIGS. 2A-B) may include a second arrangement of magnets in its connector. The controller may determine which type of pressure-mitigation apparatus has been connected based on which magnets have been detected within a specified proximity. As another example, the pressure-mitigation device designed for deployment on elongated objects may include a beacon capable of emitting a first electronic signature, while the pressure-mitigation device designed for deployment on non-elongated objects may include a beacon capable of emitting a second electronic signature. Examples of beacons include Bluetooth beacons, USB beacons, and infrared beacons. A beacon may be configured to communicate with the controller via a wired communication channel or a wireless communication channel.

The controller can then identify a pattern that is associated with the pressure-mitigation device (step 1202). For example, the controller may examine a library of patterns corresponding to different pressure-mitigation devices to identify the appropriate pattern. The library of patterns may be stored in a local memory (e.g., the memory 804 of FIG. 8) or a remote memory that is accessible to the controller across a network. The controller may modify an existing pattern based on the pressure-mitigation device, the user, the ailment affecting the user, etc. For example, the controller may alter an existing pattern responsive to determining that the pattern includes instructions for more chambers than the pressure-mitigation device includes. As another example, the controller may alter an existing pattern responsive to determining that the weight of the user exceeds a predetermined threshold.

In some embodiments, the pattern is associated with a characteristic of the user in addition to, or instead of, the pressure-mitigation device. For example, the controller may examine a library of patterns corresponding to different ailments or different anatomical regions to identify the appropriate pattern. Thus, the library may include patterns associated with anatomical regions along the anterior side of the human body, patterns associated with anatomical regions along the posterior side of the human body, or patterns associated with different ailments (e.g., ulcers, strokes, etc.).

The controller can then cause the chambers of the pressure-mitigation apparatus to be inflated in accordance with the pattern (step 1203). As discussed above, the controller can cause the pressure on one or more anatomical regions of the human body to be varied by controllably inflating one or more chambers, deflating one or more chambers, or any combination thereof.

Other steps may be performed in some embodiments. As an example, the controller may be configured to regulate inflation of the chambers based on a total duration of use of the pressure-mitigation device. For instance, the controller may increase or decrease the flow of air into the chambers (and therefore, the pressure of those chambers) in a continual, periodic, or ad hoc manner to account for extended applications of pressure on the human body. In some embodiments, the controller determines the total duration of use based on a clock signal generated by a clock module housed in the controller. In other embodiments, the controller determines the total duration of use based on signal(s) generated by some other computing device. For instance, the controller may be able to infer how long the pressure-mitigation device has been used based on the presence of a signal generated by a computing device associated with the patient, such as a mobile phone or wearable electronic device. Said another way, the controller may infer the presence of the patient based on whether his/her computing device is located within a given proximity. For example, the controller may infer that the pressure-mitigation device has been in use so long as the computing device is (1) presently detectable (e.g., via a point-to-point wireless channel, such as Bluetooth or Wi-Fi P2P) and (2) has been detectable for at least a certain amount of time (e.g., more than three minutes, five minutes, etc.).

Those skilled in the art will recognize that the approaches to mitigating the pressure described herein may be useful in various contexts. Several examples are provided below; however, these examples should not be construed as limiting in any sense. Instead, these examples are provided to illustrate the usefulness of mitigating pressure in a few different scenarios.

FIG. 13 is a flow diagram of a process 1300 for utilizing the side supports of a pressure-mitigation device to center a human body positioned thereon. Initially, a controller receives input indicative of an indication that the human body is situated on the pressure-mitigation device (step 1301). For example, the controller may determine that the human body is situated on the pressure-mitigation device based on an output produced by a pressure sensor embedded in, or connected to, the pressure-mitigation device. As another example, the controller may determine that the human body is situated on the pressure-mitigation device responsive to a determination that a person interacted with a tactile, visual, or audible element of the controller.

The controller can then inflate a first side support of a pair of side supports that extend along opposing longitudinal sides of the pressure-mitigation device (step 1302). Thereafter, the controller can inflate a second side support of the pair of side supports (step 1303). In some embodiments, steps 1302 and 1303 are performed a single time so that the human body is laterally centered on the pressure-mitigation device by sequentially inflating the pair of side supports to form a channel. In other embodiments, steps 1302 and 1303 are performed at least twice so that the human body is laterally centered on the pressure-mitigation device by alternately inflating the pair of side supports.

Then, the controller can determine that the human body is properly oriented on the pressure-mitigation device (step 1304). Like step 1301, the controller may determine that the human body has been properly oriented on the pressure-mitigation device based on an output produced by a pressure sensor embedded in, or connected to, the pressure-mitigation device, or the controller may determine that the human body is situated on the pressure-mitigation device responsive to a determination that a person interacted with a tactile, visual, or audible element of the controller.

In response to determining that the human body is properly oriented on the pressure-mitigation device, the controller can cause the chambers of the pressure-mitigation device to be inflated and/or deflated in accordance with a pattern (step 1305), as discussed above with reference to FIG. 12. In some embodiments, the pair of side supports are used to alleviate pressure applied to the human body by the underlying surface by being inflated in accordance with the pattern. In other embodiments, the pair of side supports are only used for orientation purposes. Accordingly, after the human body has been properly oriented on the pressure-mitigation device, the pair of side supports may remain in an inflated state or a deflated state. Whether the pair of side supports are used to relieve pressure may depend on the weight of the human body, among other things. For example, the pair of side supports may only be used to orient the human body if the user is a lightweight patient (e.g., less than 250 pounds), and the pair of side supports may be used to relieve pressure on the human body if the user is a heavyweight patient (e.g., more than 250 pounds).

FIG. 14 includes a flow diagram of a process 1400 for transmitting data related to the flow of fluid from a controller into a pressure-mitigation device to a destination external to the controller. Initially, the controller may receive input indicative of a request to inflate the chambers of the pressure-mitigation device in accordance with a programmed pattern to treat a human body (step 1401). The input may be representative of a discovery of a machine-readable code that is associated with the human body in a digital image that is obtained by the controller, or the input may be representative of a discovery of human-readable characters that convey information regarding the human body in a digital image that is obtained by the controller. As mentioned above, these digital images could be generated by an image sensor included in the controller, or these digital images could be obtained, by a communication module, from a source external to the controller. Alternatively, the input may be representative of a discovery of an electronic signature that conveys information regarding the human body. In some embodiments, the input is simply representative of an interaction with the controller, indicating that treatment is to begin, The controller can then cause fluid to flow into each of the chambers of the pressure-mitigation device in accordance with the programmed pattern (step 1402). Step 1402 of FIG. 14 may be similar to step 1203 of FIG. 12. By controllably inflating the chambers, the controller can shift the force that is applied to the human body by an underlying surface over time.

Moreover, the controller can transmit data regarding the flow of fluid to a destination that is external to the controller (step 1403). For example, the controller may transmit the data to a computing device via a wireless communication channel, for analysis by a computer program executing on the computing device. This data may be representative of pressure data or analyses of pressure data. Meanwhile, the computing device may be associated with the user, a healthcare professional, a caregiver, or some other entity. Assume, for example, that treatment of the user is overseen by healthcare professionals associated with a healthcare provider, such as a hospital, clinic, surgery facility, recovery center, or nursing home. In such a scenario, the controller may provide the data to a computer program associated with the healthcare provider, for further analysis. In some embodiments, data is periodically transmitted to the destination by the controller, such that each "batch" of data provides information regarding the flow of fluid over an interval of time. In other embodiments, data is continually transmitted to the destination by the controller, such that data is communicated to the computer program in near real time as it is generated by the controller.

FIG. 15 includes a flow diagram of a process 1500 for adjusting the programmed pattern for inflating the chambers of a pressure-mitigation device based on data received from a source external to the controller. Initially, the controller may receive input indicative of a request to inflate the chambers of the pressure-mitigation device in accordance with a programmed pattern to treat a human body (step 1501). Step 1501 of FIG. 15 may be similar to step 1401 of FIG. 14.

Thereafter, the controller can obtain data regarding the health of the human body from a source external to the controller (step 1502). For example, the controller may obtain the data from a computing device via a wireless communication channel. The computing device could be associated with a healthcare professional, caregiver, or the user herself. In some embodiments, the computing device is managed by, or accessible to, a healthcare provider responsible for managing treatment of the user. For example, the controller may access or retrieve information from an electronic health record associated with the user as discussed above. In other embodiments, the computing device is a medical device that was used to treat, or is presently treating, the human body.

The controller can then adjust the programmed pattern based on the data (step 1503) and cause fluid to flow into the chambers of the pressure-mitigation device in accordance with the adjusted programmed pattern (step 1504). Such an approach allows the controller to "tune" the programmed pattern to be better suited for the user.

Figure 16:
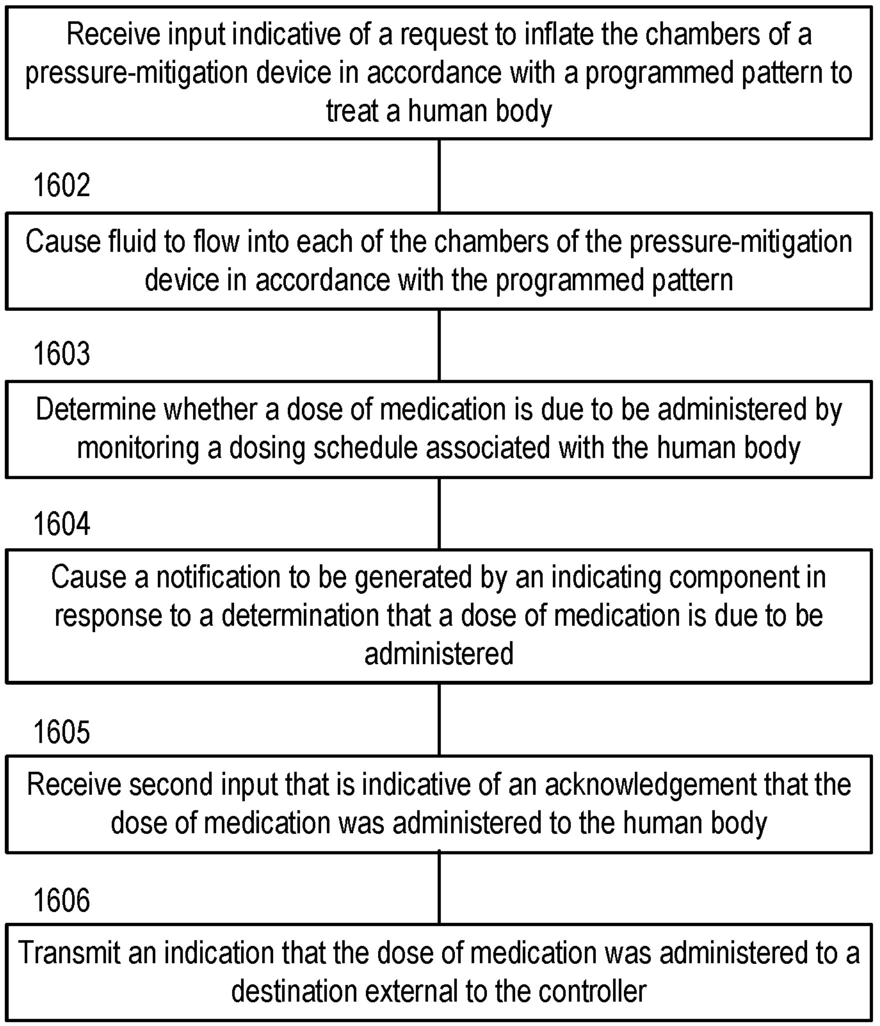
FIG. 16 includes a flow diagram of a process for monitoring a medication regimen while continuing to controllably alleviate the force applied to a user by an underlying surface.

FIG. 16 includes a flow diagram of a process 1600 for monitoring a medication regimen while continuing to controllably alleviate the force applied to a user by an underlying surface. Initially, the controller may receive input indicative of a request to inflate the chambers of the pressure-mitigation device in accordance with a programmed pattern to treat a human body (step 1601). Step 1601 of FIG. 16 may be similar to step 1401 of FIG. 14. The controller can then cause fluid to flow into each of the chambers of the pressure-mitigation device in accordance with the programmed pattern (step 1602). Step 1602 of FIG. 16 may be similar to step 1203 of FIG. 12. By controllably inflating the chambers, the controller can shift the force that is applied to the human body by an underlying surface over time.

While the human body is being treated by the pressure-mitigation device, the controller may also monitor a medication regimen. More specifically, the controller may promote compliance with the medication regimen as part of a holistic approach to improving health. The controller can determine whether a dose of medication is due to be administered by monitoring a dosing schedule associated with the human body (step 1603), so that the medication is administered—by the user or another person—as necessary while treatment is being provided by the pressure-mitigation device. To accomplish this, the controller may continually compare a clock signal generated by a clock module against administration timings that are defined by the dosing schedule. In the event that the clock signal matches an administration timing (or is past an administration timing), the controller can determine that a dose of medication is due to be administered.

When the controller determines that a dose of medication is due to be administered, the controller may cause a notification to be generated by an indicating component (step 1604). In some embodiments, the controller may receive second input that is indicative of an acknowledgement that the dose of medication was administered to the human body (step 1605). For example, the second input may be indicative of an interaction with a mechanical component of the controller, or the second input may be indicative of an utterance, recorded by an audio input mechanism, that the dose of medication was administered. Upon receiving the second input, the controller may transmit an indication that the dose of medication was administered to a destination external to the controller (step 1606). The destination could be a computing device that is (i) accessible to the controller via a network and (ii) has a computer program executing thereon that monitors adherence to the medication regimen. Note that in some embodiments, the dosing schedule may be received from a source that is external to the controller. The source could be the same computing device that serves as the destination of the indication, or the source could be a different computing device than the destination.

Figure 17:
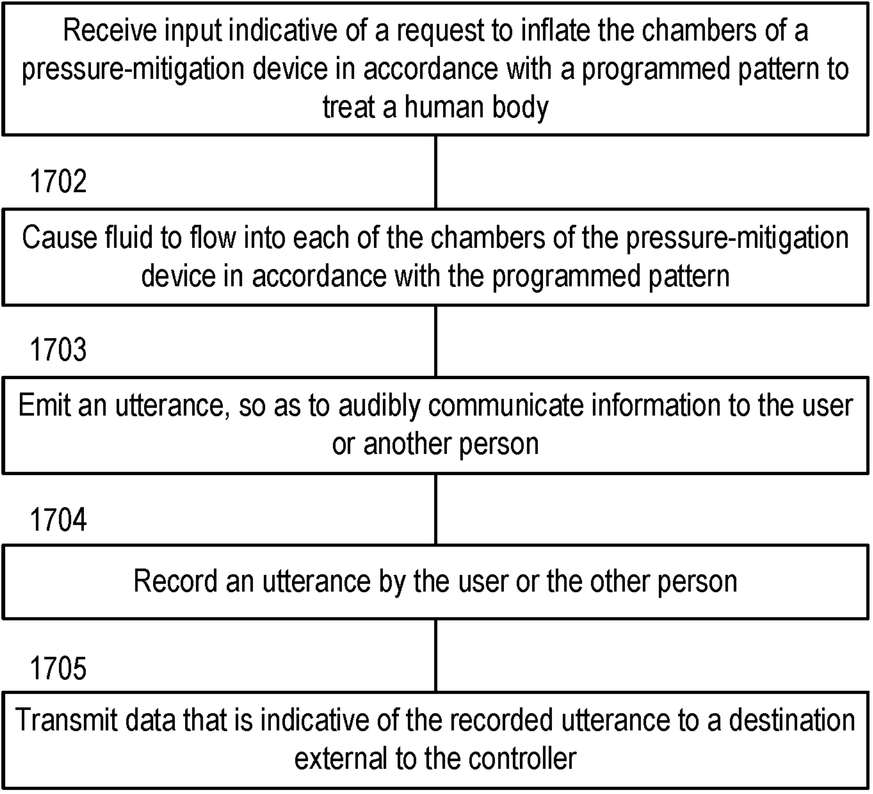
FIG. 17 includes a flow diagram of a process for audibly communicating with a user or an operator of a pressure-mitigation system.

FIG. 17 includes a flow diagram of a process 1700 for audibly communicating with a user or an operator of a pressure-mitigation system. Initially, the controller may receive input indicative of a request to inflate the chambers of the pressure-mitigation device in accordance with a programmed pattern to treat a human body (step 1701). Step 1701 of FIG. 17 may be similar to step 1401 of FIG. 14. The controller can then cause fluid to flow into each of the chambers of the pressure-mitigation device in accordance with the programmed pattern (step 1702). Step 1702 of FIG. 17 may be similar to step 1203 of FIG. 12. By controllably inflating the chambers, the controller can shift the force that is applied to the human body by an underlying surface over time.

Moreover, the controller may emit an utterance, so as to audibly communicate information to the user or another person (step 1703). The utterance could be emitted before treatment begins, in which case the utterance may be representative of an instruction regarding how to deploy or use the pressure-mitigation apparatus or controller. Alternatively, the utterance could be emitted as treatment occurs or after treatment concludes, in which case the utterance may be representative of an inquiry, from a healthcare professional, regarding the health of the human body. For example, a healthcare professional may query the user as to whether treatment has improved any of her symptoms.

Further, the controller may record an utterance by the user or the other person (step 1704). This recorded utterance may be responsive to the emitted utterance, or vice versa. Thereafter, the controller may transmit data that is indicative of the recorded utterance to a destination external to the controller (step 1705). As discussed above, steps 1703-1705 could be performed in near real time, so as to allow for conversation between individuals who are not located near one another.

FIG. 18 includes a flow diagram of a process 1800 for controllably dispensing fluid into the ambient environment while a user is being treated with a pressure-mitigation system. Initially, the controller may receive input indicative of a request to inflate the chambers of the pressure-mitigation device in accordance with a programmed pattern to treat a human body (step 1801). Step 1801 of FIG. 18 may be similar to step 1401 of FIG. 14. The controller can then cause fluid to flow into each of the chambers of the pressure-mitigation device in accordance with the programmed pattern (step 1802). Step 1802 of FIG. 18 may be similar to step 1203 of FIG. 12. By controllably inflating the chambers, the controller can shift the force that is applied to the human body by an underlying surface over time.

Further, the controller may dispense a fluid into the ambient environment (step 1803). Generally, the fluid is dispensed while treatment is being provided by the pressure-mitigation device, though the fluid could be dispensed before treatment begins or after treatment concludes. In some embodiments, the fluid is not scented. For example, the controller may dispense water into the ambient environment to promote humidification, especially if it is determined (e.g., based on an output produced by the sensor suite or feedback received from the user) that humidity is uncomfortably low. In other embodiments, the fluid is scented. In such embodiments, the fluid may be dispensed as part of an aromatherapy program or simply to relax the user.

While fluid could be dispensed in an ad hoc manner, fluid is normally dispensed in accordance with a dispensing schedule. The dispensing schedule could be programmatically associated with the programmed pattern for inflating the chambers of the pressure-mitigation apparatus in the memory of the controller. The dispensing schedule could be programmed into the memory, for example, by the manufacturer prior to distribution, or the dispensing schedule could be received from a source external to the controller. For example, the dispensing schedule could be received from a computing device that is associated with a healthcare professional, a caregiver, or the user herself. Via the computing device, the dispensing schedule may be selected from among various dispensing scheduled corresponding to different scents, intensities, dispensation frequencies, etc.

FIG. 19 includes a flow diagram of a process 1900 for interfacing with an electronic health record of a user that is to be treated with a pressure-mitigation system. Initially, the controller may receive input indicative of a request to inflate the chambers of the pressure-mitigation device in accordance with a programmed pattern to treat a human body (step 1901). Step 1901 of FIG. 19 may be similar to step 1401 of FIG. 14. The controller can then transmit a request for information related to the human body to a storage medium that is accessible via a network (step 1902). The storage medium can include a database of electronic health records that are managed by, or accessible to, a healthcare provider that is responsible for prescribing or monitoring the treatment of the human body by the pressure-mitigation device. The storage medium may be part of a server system that is managed by a cloud computing service, such as Amazon Web Services®, Google Cloud Platform™, or Microsoft Azure®. In such a scenario, the healthcare provider may be able to upload data to, and manipulate data on, the server system. Alternatively, the storage medium may be part of an "on-premises" storage solution that is managed by the healthcare provider.

Thereafter, the controller can receive, from the storage medium, the information that is extracted from an electronic health record associated with the human body (step 1903). In some embodiments the controller retrieves the information from the electronic health record, while in other embodiments the controller simply accesses the information to glean an insight into the health of the user.

The controller can then determine whether any adjustment of a programmed pattern for inflating the chambers of the pressure-mitigation device is necessary based on an analysis of the information (step 1904). For example, the controller may parse the information—or the electronic health record itself—to determine whether the age, weight, or ailment of the user indicates that an adjustment is necessary. In the event that the controller adjusts the programmed pattern (step 1905), the controller can cause the chambers to be inflated in accordance with the adjusted programmed pattern (step 1906).

Note that while the sequences of the steps performed in the processes described herein are exemplary, the steps can be performed in various sequences and combinations. For example, steps could be added to, or removed from, these processes. Similarly, steps could be replaced or reordered. Thus, the descriptions of these processes are intended to be open ended.

Overview of Pressure-Mitigation Systems

Figure 20:
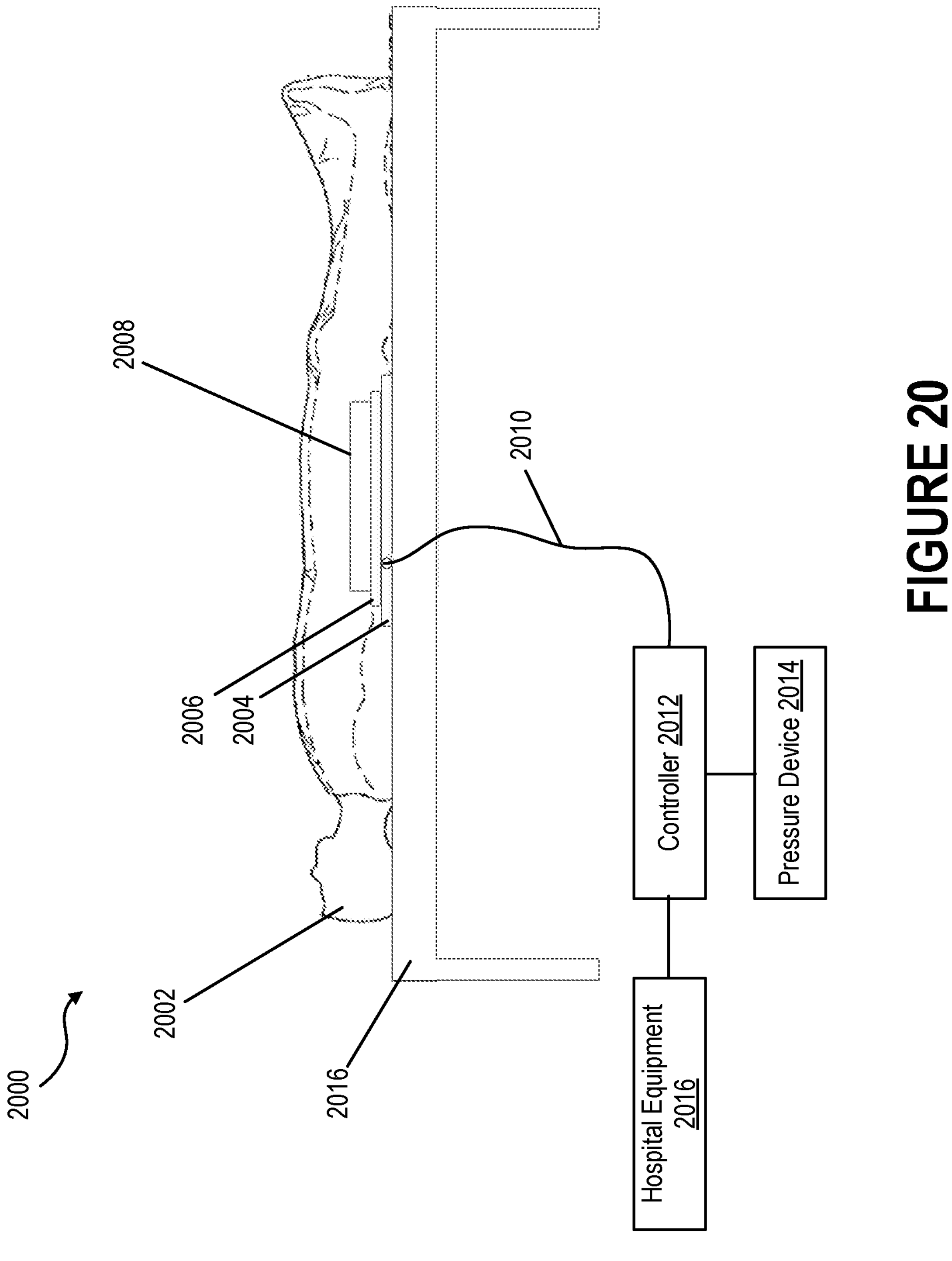
FIG. 20 is a partially schematic side view of a pressure-mitigation system (or simply "system") for orienting a user over a pressure-mitigation device in accordance with embodiments of the present technology.

FIG. 20 is a partially schematic side view of a pressure-mitigation system 2000 (or simply "system") for orienting a user 2002 over a pressure-mitigation device 2006 in accordance with embodiments of the present technology. Here, the system 2000 includes a pressure-mitigation device 2006 that include side supports 2008, an attachment device 2004, a pressure device 2014, and a controller 2012. Other embodiments of the system 2000 may include a subset of these components. For example, the system 2000 may include a pressure-mitigation device 2006, a pressure device 2014, and a controller 2012. The pressure-mitigation device 2006 is discussed in further detail with respect to FIGS. 1A-4C, and the controller 2012 is discussed in further detail with respect to FIGS. 7A-10.

Figure 21A:
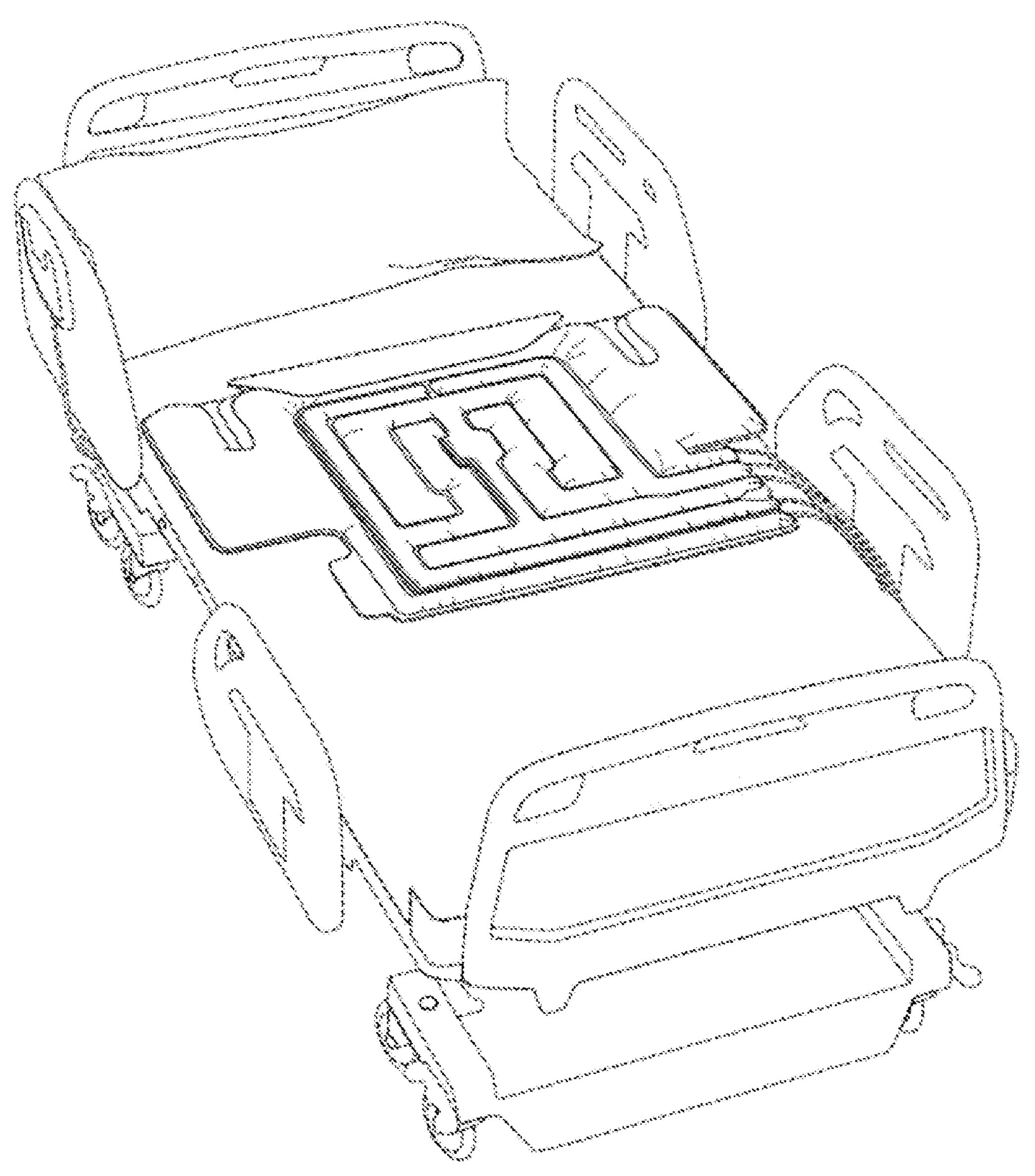
FIG. 21A illustrates an example of a pressure-mitigation device that includes a pair of elevated side supports that has been deployed on the surface of an object (here, a hospital bed).
Figure 21B:
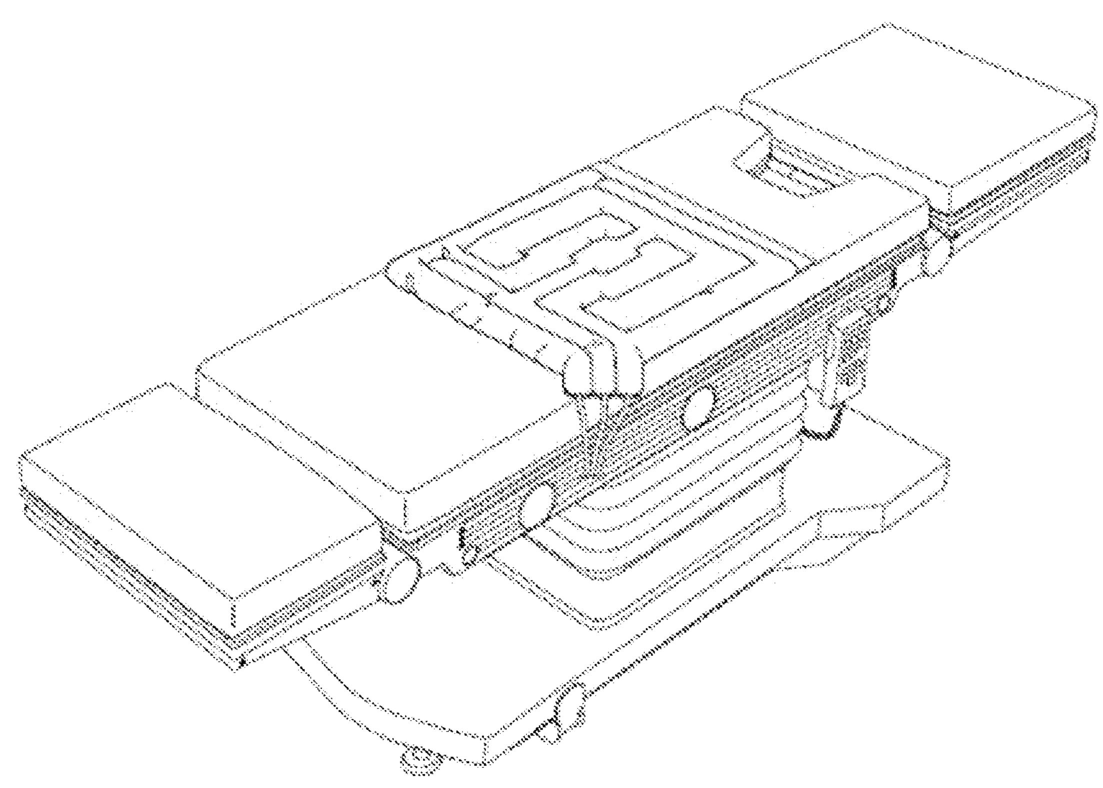
FIG. 21B illustrates an example of a pressure-mitigation device with no elevated side supports that has deployed on the surface of an object (here, an operating table).

In this embodiment, the pressure-mitigation device 2006 includes a pair of elevated side supports 2008 that extend longitudinally along opposing sides of the pressure-mitigation device 2006. FIG. 21A illustrates an example of a pressure-mitigation device that includes a pair of elevated side supports that has been deployed on the surface of an object (here, a hospital bed). However, some embodiments of the pressure-mitigation device 2006 do not include any elevated side supports. For example, side supports may not be necessary if the object on which the user 2002 is positioned includes lateral structures that prevent or inhibit horizontal movement, or if the user 2002 will be completely immobilized (e.g., using anesthesia). FIG. 21B illustrates an example of a pressure-mitigation device with no elevated side supports that has deployed on the surface of an object (here, an operating table). The pressure-mitigation device 2006 includes a series of chambers interconnected on a base material that may be arranged in a geometric pattern designed to mitigate the pressure applied to an anatomical region by the surface of the object 22222016.

The elevated side supports 2008 can be configured to actively orient the anatomical region of the user 2002 over the series of chambers. For example, the elevated side supports 2008 may be responsible for actively orienting the anatomical region widthwise over the epicenter of the geometric pattern. As shown in FIG. 20, the anatomical region may be the sacral region. However, the anatomical region could be any region of the human body that is susceptible to pressure. The elevated side supports 2008 may be configured to be ergonomically comfortable. For example, the elevated side supports 2008 may include a recess designed to accommodate the forearm that permits pressure to be offloaded from the elbow. The elevated side supports 2008 may be significantly larger in size than the chambers of the pressure-mitigation device 2006. Accordingly, the elevated side supports 2008 may create a barrier that restricts lateral movement of the user 2002. In some embodiments, the elevated side supports are approximately 2-3 inches taller in height as compared to the average height of an inflated chamber. Because the elevated side supports 2006 straddle the user 2002, the elevated side supports 2008 can act as barriers for maintaining the position of the user 2002 on top of the pressure-mitigation device 2006. As discussed above, the elevated side supports 2008 may be omitted in some embodiments. For example, the elevated side supports 2008 may be omitted if the user 2002 suffers from impaired mobility due to physical injury, structural components that limit movement, anesthesia, or some other condition that limits natural movement.

In some embodiments, the inner side walls of the elevated side supports 2008 form, following inflation, a firm surface at a steep angle of orientation with respect to the pressure-mitigation device 2006. For example, the inner side walls may be on a plane of approximately 115 degrees, plus or minus 24 degrees, from the plane of the pressure-mitigation device 2006. These steep inner side walls can form a channel that naturally positions the user 2002 over the chambers of the pressure-mitigation device 2006. Thus, inflation of the elevated side supports 2008 may actively force the user 2002 into the appropriate position for mitigating pressure by orienting the body in the correct location with respect to the chambers of the pressure-mitigation device 2006.

After the initial inflation cycle has been completed, the pressure of each elevated side support 2008 may be lessened to increase comfort and prevent excessive force against the lateral sides of the user 2002. Oftentimes, a healthcare professional will be present during the initial inflation cycle to ensure that the elevated side supports 2008 properly position the user 2002 over the pressure-mitigation device 2006, though that need not necessarily be the case (e.g., if the pressure-mitigation device 2006 is deployed in a home environment).

The controller 2012 can be configured to regulate the pressure of each chamber in the pressure-mitigation device 2006 (and the elevated side supports 2008, if included) via one or more flows of air generated by a pressure device 2014. One example of a pressure device is an air pump. These flow(s) of air can be guided from the controller 2012 to the pressure-mitigation device 2006 via tubing 2010. For example, the chambers may be controlled in a specific pattern to preserve blood flow and reduce pressure applied to the user 2002 when inflated (i.e., pressurized) and deflated (i.e., depressurized) in a coordinated fashion by the controller 2012. As shown in FIG. 20, the tubing 2010 may be connected between the pressure-mitigation device 2006 and the controller 2012. Accordingly, the pressure-mitigation device 2006 may be fluidically coupled to a first end of tubing (e.g., single-channel tubing or multi-channel tubing) while the controller 2012 may be fluidically coupled to a second end of the tubing. While the pressure device 2012 is normally housed within the controller 2012, these components could be connected via tubing. Thus, the pressure device 2014 could be fluidically coupled to a first end of tubing (e.g., single-channel tubing or multi-channel tubing) while the controller 2006 may be fluidically coupled to a second end of the tubing. As mentioned above, the multi-channel tubing 2010 may not be needed in some embodiments. For example, the controller 2012 could be directly attached to the pressure-mitigation device 2006, thereby eliminating the need for tubing between the controller 2012 and pressure-mitigation device 2006.

As discussed above, some embodiments of the system 2000 include a communication module configured to facilitate wireless communication with nearby computing devices. For example, the controller 2012 may include a communication module able to wirelessly communicate with hospital equipment 22222016 involved in treatment of the user 2002. Examples of hospital equipment include ECMO machines, mechanical ventilators, mobile workstations, monitors, and the like. The controller 2012 may be able to pressurize the inflatable chambers of the pressure-mitigation device 2006 based on information obtained from the hospital equipment. For instance, the controller 2012 may alter a programmed pattern for pressurizing the inflatable chambers based on the current status of the hospital equipment 2006, whether the hospital equipment 2006 indicates that there is a problem, etc. As an example, the controller 2012 may receive, via the communication module, input from a mechanical ventilator that a procedure (e.g., suctioning, spraying of medication, bronchoscopy) will be performed. In such a scenario, the controller 2012 may cause all inflatable chambers of the pressure-mitigation device 2006 to be pressurized (i.e., inflated) or depressurized (i.e., deflated) so that the procedure is easier to perform. Thus, the controller 2012 may discontinue treatment in accordance with the programmed pattern responsive to determining that it is not safe, appropriate, or desirable to continue treatment.

Processing System

Figure 22:
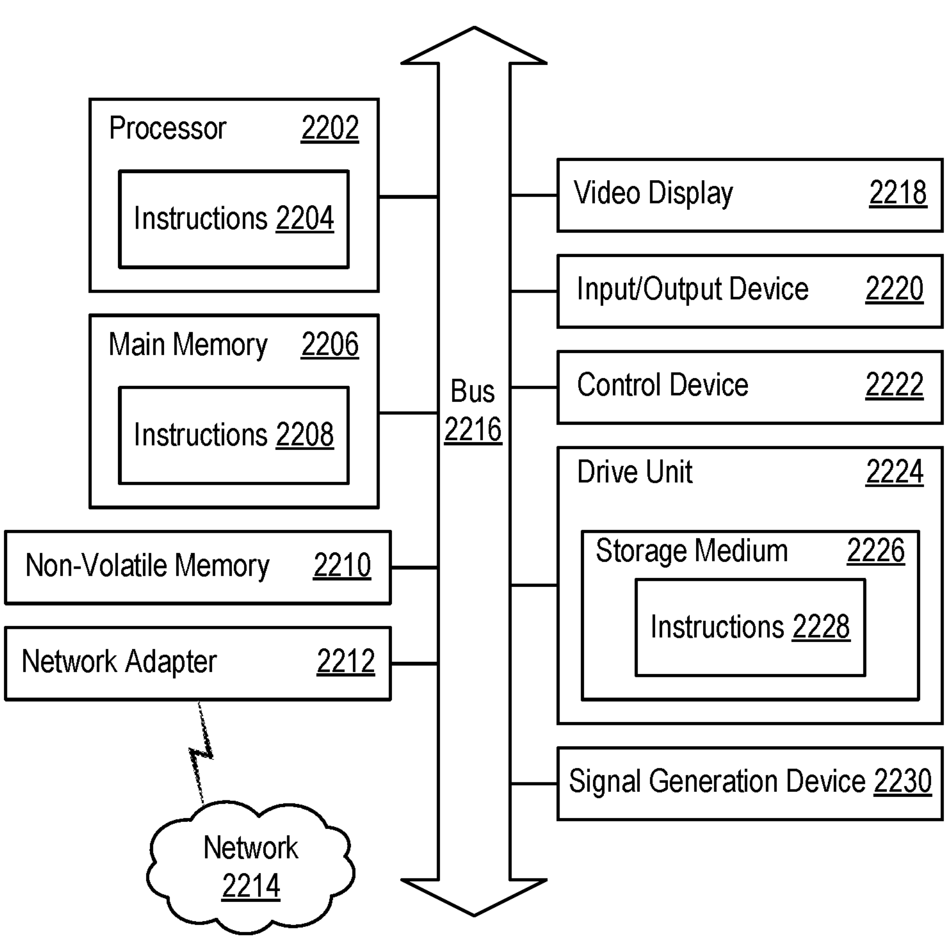
FIG. 22 is a block diagram illustrating an example of a processing system in which at least some operations described herein can be implemented.

FIG. 22 is a block diagram illustrating an example of a processing system 2200 in which at least some operations described herein can be implemented. For example, components of the processing system 2200 may be hosted on a controller (e.g., controller 2012 of FIG. 20) responsible for controlling the flow of fluid to a pressure-mitigation device (e.g., pressure-mitigation apparatus 2006 of FIG. 20). As another example, components of the processing system 2200 may be hosted on a computing device that is communicatively coupled to the controller.

The processing system 2200 may include a processor 2202, main memory 2206, non-volatile memory 2210, network adapter 2212 (e.g., a network interface), video display 2218, input/output device 2220, control device 2222 (e.g., a keyboard, pointing device, or mechanical input such as a button), drive unit 2224 that includes a storage medium 2226, or signal generation device 2230 that are communicatively connected to a bus 222216. The bus 222216 is illustrated as an abstraction that represents one or more physical buses and/or point-to-point connections that are connected by appropriate bridges, adapters, or controllers. The bus 222216, therefore, can include a system bus, Peripheral Component Interconnect (PCI) bus, PCI-Express bus, HyperTransport bus, Industry Standard Architecture (ISA) bus, Small Computer System Interface (SCSI) bus, Universal Serial Bus (USB), Inter-Integrated Circuit ($I^2C$) bus, or bus compliant with Institute of Electrical and Electronics Engineers (IEEE) Standard 1394.

The processing system 2200 may share a similar computer processor architecture as that of a computer server, router, desktop computer, tablet computer, mobile phone, video game console, wearable electronic device (e.g., a watch or fitness tracker), network-connected ("smart") device (e.g., a television or home assistant device), augmented or virtual reality system (e.g., a head-mounted display), or another computing device capable of executing a set of instructions (sequential or otherwise) that specify action(s) to be taken by the processing system 2200.

While the main memory 2206, non-volatile memory 2210, and storage medium 2224 are shown to be a single medium, the terms "storage medium" and "machine-readable medium" should be taken to include a single medium or multiple media that stores one or more sets of instructions 2226. The terms "storage medium" and "machine-readable medium" should also be taken to include any medium that is capable of storing, encoding, or carrying a set of instructions for execution by the processing system 2200.

In general, the routines executed to implement the embodiments of the present disclosure may be implemented as part of an operating system or a specific application, component, program, object, module, or sequence of instructions (collectively referred to as "computer programs"). The computer programs typically comprise one or more instructions (e.g., instructions 2204, 2208, 2228) set at various times in various memories and storage devices in a computing device. When read and executed by the processor 2202, the instructions cause the processing system 2200 to perform operations to execute various aspects of the present disclosure.

While embodiments have been described in the context of fully functioning computing devices, those skilled in the art will appreciate that the various embodiments are capable of being distributed as a program product in a variety of forms. The present disclosure applies regardless of the particular type of machine- or computer-readable medium used to actually cause the distribution. Further examples of machine- and computer-readable media include recordable-type media such as volatile and non-volatile memory devices 2210, removable disks, hard disk drives, optical disks (e.g., Compact Disk Read-Only Memory (CD-ROMS) and Digital Versatile Disks (DVDs)), cloud-based storage, and transmission-type media such as digital and analog communication links.

The network adapter 2212 enables the processing system 2200 to mediate data in a network 2214 with an entity that is external to the processing system 2200 through any communication protocol supported by the processing system 2200 and the external entity. The network adapter 2212 can include a network adaptor card, a wireless network interface card, a switch, a protocol converter, a gateway, a bridge, a hub, a receiver, a repeater, or a transceiver that includes a chip (e.g., enabling communication over Bluetooth or Wi-Fi).

The techniques introduced here can be implemented using software, firmware, hardware, or a combination of such forms. For example, aspects of the present disclosure may be implemented using special-purpose hardwired (i.e., non-programmable) circuitry in the form of ASICs, programmable logic devices (PLDs), field-programmable gate arrays (FPGAs), and the like.

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A controller comprising:

a structural body that includes an egress interface that is fluidly coupled to a pressure-mitigation apparatus configured to be situated between a human body and a surface, wherein the pressure-mitigation apparatus includes a plurality of chambers;

a clock module that is operable to generate a clock signal;

an indicating component that is operable to produce visual notifications, audible notifications, or tactile notifications;

a processor; and a memory that includes (i) an inflation schedule that specifies pressures to which the plurality of chambers of the pressure-mitigation apparatus are to be inflated and durations for which the pressures are to be maintained, (ii) a dosing schedule that specifies times at which a medication is to be administered to the human body, and (iii) instructions that, when executed by the processor, cause the processor to:

compare, in a continuous manner, the clock signal to (a) the inflation schedule, such that the plurality of chambers are inflated to the pressures specified by the inflation schedule and for the durations specified by the inflation schedule based on the clock signal, thereby shifting force applied by the surface to the human body to different positions over time, and (b) the dosing schedule, such that determinations as to whether a dose of medication is due to be administered are made based on the clock signal, such that the inflation schedule and the dosing schedule are synchronously monitored using the clock signal, and cause a notification to be generated by the indicating component in response to a determination that a dose of medication is due to be administered.

2. The controller of claim 1, wherein the indicating component is a display mechanism that is able to produce visual notifications.

3. The controller of claim 1, wherein the indicating component is an audio output mechanism that is able to produce audible notifications.

4. The controller of claim 1, wherein the indicating component is a haptic element that is able to produce tactile notifications.

5. The controller of claim 1, further comprising:

a communication module configured to— initiate communication with a computer program executing on a computing device that is accessible via a network, and obtain the dosing schedule from the computer program.

6. The controller of claim 5, wherein the computing device is a mobile phone that is configured to be associated with the human body.

7. The controller of claim 5, wherein the computing device is a computer server that is part of a server system, and wherein the computer program is managed by a healthcare entity responsible for prescribing the medication.

8. The controller of claim 1, further comprising:

an ingress interface that is fluidically coupled to a pump that supplies a flow of fluid that is manipulated by the controller to inflate the plurality of chambers in accordance with the inflation schedule.

9. The controller of claim 1, further comprising:

a pump that supplies a flow of fluid that is manipulated to inflate the plurality of chambers in accordance with the inflation schedule.

10. A method performed by a controller that is fluidly connected to a pressure-mitigation device that alleviates force on an anatomical region of a human body, the method comprising:

receiving input indicative of a request to inflate chambers of the pressure-mitigation device in accordance with a programmed pattern that specifies pressures to which the chambers of the pressure-mitigation device are to be inflated and durations for which the pressures are to be maintained;

comparing, in a continuous manner, a clock signal to the programmed pattern and a dosing schedule that is stored in a memory of the controller;

causing, based on said comparing of the clock signal to the programmed pattern, fluid to flow into each of the chambers at varying rates in accordance with the programmed pattern, thereby shifting the force applied by an underlying surface to the anatomical region of the human body over time; and determining, based on said comparing of the clock signal to the dosing schedule, whether a dose of medication is due to be administered, so that the medication is administered as necessary while treatment is being provided by the pressure-mitigation device.

11. The method of claim 10, further comprising:

causing a notification to be generated by an indicating component in response to a determination that a dose of medication is due to be administered.

12. The method of claim 11, wherein the notification is generated by the indicating component on a periodic basis based the comparison of the clock signal to the dosing schedule.

13. The method of claim 10, further comprising:

in response to a determination that a dose of medication is due to be administered, causing a first notification to be generated by a first indicating component, and causing a second notification to be generated by a second indicating component.

14. The method of claim 13, wherein the first indicating component is an audio output mechanism that is able to produce audible notifications, and wherein the second indicating component is a display mechanism that is able to produce visual notifications.

15. The method of claim 10, further comprising:

receiving second input indicative of an acknowledgement that a dose of medication was administered to the human body.

16. The method of claim 15, wherein the second input is indicative of an interaction with a mechanical component of the controller.

17. The method of claim 15, further comprising:

transmitting data indicating that the dose of medication was administered to a destination external to the controller.

18. The method of claim 17, wherein the destination is a computer program executing on a computing device that is communicatively connected to the controller.

19. The method of claim 10, further comprising:

receiving the dosing schedule from a source external to the controller and accessible to the controller via a network.

20. The method of claim 10, wherein the programmed pattern is configured to simulate microadjustments made by healthy individuals by shifting the force between at least three locations across the anatomical region of the human body.

* * * * *